(12) United States Patent
Bleck

(10) Patent No.: US 7,378,273 B2
(45) Date of Patent: *May 27, 2008

(54) EXPRESSION VECTORS

(75) Inventor: Gregory T. Bleck, Baraboo, WI (US)

(73) Assignee: Gala Design, Inc., Middleton, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/947,881

(22) Filed: Sep. 23, 2004

(65) Prior Publication Data

US 2005/0060762 A1    Mar. 17, 2005

Related U.S. Application Data

(63) Continuation of application No. 09/897,006, filed on Jun. 29, 2001, now abandoned.

(60) Provisional application No. 60/215,851, filed on Jul. 3, 2000.

(51) Int. Cl.
*C12N 5/00* (2006.01)
*C07H 21/04* (2006.01)
*A01N 63/00* (2006.01)
*C12P 21/06* (2006.01)

(52) U.S. Cl. .................. 435/320.1; 435/325; 435/69.1; 536/24.1; 424/93.2

(58) Field of Classification Search ............. 435/69.1, 435/320.1, 325, 91.4; 424/93.2
See application file for complete search history.

(56) References Cited

U.S. PATENT DOCUMENTS

| | | | |
|---|---|---|---|
| 4,560,655 A | 12/1985 | Baker | 435/241 |
| 4,657,866 A | 4/1987 | Kumar | 435/240 |
| 4,677,066 A | 6/1987 | Takahashi et al. | 435/172.2 |
| 4,767,704 A | 8/1988 | Cleveland et al. | 435/68 |
| 4,816,567 A | 3/1989 | Cabilly et al. | 530/387 |
| 4,927,762 A | 5/1990 | Darfler | 435/240.31 |
| 4,937,190 A | 6/1990 | Palmenberg et al. | 435/69.1 |
| 4,946,778 A | 8/1990 | Ladner et al. | 435/69.6 |
| 5,122,469 A | 6/1992 | Mather et al. | 435/240.2 |
| 5,149,645 A | 9/1992 | Hoekema et al. | 435/172.3 |
| 5,168,062 A | 12/1992 | Stinski | 435/240.2 |
| 5,173,414 A | 12/1992 | Lebkowski et al. | 435/172.3 |
| 5,215,904 A | 6/1993 | Gould et al. | 435/172.3 |
| 5,225,347 A | 7/1993 | Goldberg et al. | 435/320.1 |
| 5,385,839 A | 1/1995 | Stinski | 435/240.2 |
| 5,508,184 A | 4/1996 | Negrutiu et al. | 435/172.3 |
| 5,512,421 A | 4/1996 | Burns et al. | 435/320.1 |
| 5,512,443 A | 4/1996 | Schlom et al. | 435/7.23 |
| 5,591,624 A | 1/1997 | Barber et al. | 435/240.2 |
| 5,618,682 A | 4/1997 | Scheirer | 435/8 |
| 5,627,058 A | 5/1997 | Ruley et al. | 435/172.3 |
| 5,670,113 A | 9/1997 | Akong et al. | 422/63 |
| 5,674,713 A | 10/1997 | McElroy et al. | 435/69.7 |
| 5,686,120 A | 11/1997 | Mertz et al. | 435/320.1 |
| 5,686,279 A | 11/1997 | Finer et al. | 435/172.3 |
| 5,716,832 A | 2/1998 | Barber et al. | 435/172.3 |
| 5,719,055 A | 2/1998 | Cooper | 435/320.1 |
| 5,721,121 A | 2/1998 | Etcheverry et al. | 435/69.7 |
| 5,807,689 A | 9/1998 | Daggett et al. | 435/78 |
| 5,817,491 A | 10/1998 | Yee et al. | 435/172.3 |
| 5,834,256 A | 11/1998 | Finer et al. | 435/91.33 |
| 5,843,742 A | 12/1998 | Natsoulis et al. | 435/172.3 |
| 5,850,000 A | 12/1998 | Bleck et al. | 800/2 |
| 5,858,740 A | 1/1999 | Finer et al. | 435/172.3 |
| 5,866,400 A | 2/1999 | Palsson et al. | 435/235.1 |
| 5,874,540 A | 2/1999 | Hansen et al. | 530/387.3 |
| 5,876,946 A | 3/1999 | Burbaum et al. | 435/7.1 |
| 5,892,019 A | 4/1999 | Schlom et al. | 536/23.53 |
| 5,914,267 A | 6/1999 | Mertz et al. | 435/320.1 |
| 5,922,601 A | 7/1999 | Baetscher et al. | 435/456 |
| 5,948,675 A | 9/1999 | Klatzmann et al. | 435/320.1 |
| 5,952,212 A | 9/1999 | Moller et al. | 435/194 |
| 5,955,592 A | 9/1999 | Ullrich et al. | 536/23.2 |
| 5,958,719 A | 9/1999 | Ullrich et al. | 435/21 |
| 5,958,775 A | 9/1999 | Wickstrom et al. | 435/455 |

(Continued)

FOREIGN PATENT DOCUMENTS

EP    117058    8/1984

(Continued)

OTHER PUBLICATIONS

Lee and Johnson, Pre-mRNA Processing Enhancer (PPE) Element Increase the Expression of an Intronless Thymidylate Synthase Gene But Does Not Affect Intron-Dependent S Phase Regualtion, J. Cellular Biochemistry, 1998, vol. 69, pp. 104-116.*
Bender et al, Expression of the Human B-Globin Gene after Retroviral Transfer into Murine Erythroleukemia Cells and Human BFU-E Cells, MCB, 1988, vol. 8, No. 4, pp. 1725-1735.*
Mielke et al., Biochem. 35:2239-52 [1996].
Schroder and Friedl, Biotech. Bioeng. 53(6):547-59 [1997].
Weidle et al., Gene 66:193-203 [1988].
McBurney et al., Somatic Cell Molec. Genet. 20:529-40 [1994].
Allen et al., Plant Cell 5:603-13 [1993].

(Continued)

*Primary Examiner*—Maria Marvich
(74) *Attorney, Agent, or Firm*—Casimir Jones, S.C.

(57) ABSTRACT

The present invention provides novel regulatory elements and vectors for the expression of one or more proteins in a host cell. The present invention also provides methods for expressing one or more proteins, such as antibodies, in a host cell. These methods utilize the novel regulatory elements and vectors of the present invention for the expression of proteins in a host cell. The host cells are used for producing various protein products, including but not limited to pharmaceutical proteins, antibodies, variants of proteins for use in screening assays, and for direct use in high throughput screening.

4 Claims, 33 Drawing Sheets

U.S. PATENT DOCUMENTS

| | | | | |
|---|---|---|---|---|
| 5,965,443 | A | 10/1999 | Reznikoff et al. | 435/473 |
| 5,968,785 | A | 10/1999 | Devine et al. | 435/91.41 |
| 5,976,796 | A | 11/1999 | Szalay et al. | 435/6 |
| 5,976,852 | A | 11/1999 | Cheng et al. | 435/196 |
| 5,976,853 | A | 11/1999 | Guthridge et al. | 435/196 |
| 5,981,251 | A | 11/1999 | Ullrich et al. | 435/196 |
| 5,993,813 | A | 11/1999 | Mezes et al. | 424/133.1 |
| 5,994,074 | A | 11/1999 | Beach et al. | 435/6 |
| 5,994,136 | A | 11/1999 | Naldini et al. | 435/455 |
| 6,004,791 | A | 12/1999 | Aoki et al. | 435/194 |
| 6,013,455 | A | 1/2000 | Bandman et al. | 435/6 |
| 6,013,464 | A | 1/2000 | Abo et al. | 435/15 |
| 6,013,516 | A | 1/2000 | Verma et al. | 435/325 |
| 6,015,807 | A | 1/2000 | Engel et al. | 514/183 |
| 6,020,306 | A | 2/2000 | Boyd et al. | 514/2 |
| 6,025,192 | A | 2/2000 | Beach et al. | 435/320.1 |
| 6,027,722 | A | 2/2000 | Hodgson | 424/93.21 |
| 6,027,875 | A | 2/2000 | Weinberger | 435/6 |
| 6,030,788 | A | 2/2000 | Gerhold | 435/6 |
| 6,030,822 | A | 2/2000 | Lechner et al. | 435/194 |
| 6,034,228 | A | 3/2000 | Norris et al. | 536/23.1 |
| 6,051,427 | A | 4/2000 | Finer et al. | 435/369 |
| 6,061,427 | A | 5/2000 | Ryoo | 379/1 |
| 6,074,859 | A | 6/2000 | Hirokawa et al. | 435/189 |
| 6,080,912 | A | 6/2000 | Bremel et al. | 800/23 |
| 6,136,597 | A | 10/2000 | Hope et al. | 435/325 |
| 6,187,287 | B1 | 2/2001 | Leung et al. | 424/9.1 |
| 6,255,071 | B1 | 7/2001 | Beach et al. | 435/69.1 |
| 6,291,740 | B1 | 9/2001 | Bremel et al. | 800/23 |
| 6,319,707 | B1 | 11/2001 | Adam et al. | 435/320.1 |
| 6,331,415 | B1 | 12/2001 | Cabilly et al. | 435/69.6 |
| 6,333,195 | B1 | 12/2001 | Respess et al. | 435/456 |
| 6,368,862 | B1 | 4/2002 | Palmer et al. | 435/455 |
| 6,410,316 | B1 | 6/2002 | Sheridan et al. | 435/320.1 |
| 2001/0018203 | A1 | 8/2001 | Iba et al. | |
| 2001/0043921 | A1 | 11/2001 | Gunzburg et al. | |
| 2002/0034393 | A1 | 3/2002 | Mitrophanous et al. | |

FOREIGN PATENT DOCUMENTS

| | | |
|---|---|---|
| WO | WO 87/00195 | 1/1987 |
| WO | WO 90/03430 | 4/1990 |
| WO | WO 92/01070 | 1/1992 |
| WO | WO 93/02108 | 2/1993 |
| WO | WO 93/03143 | 2/1993 |
| WO | WO 93/03769 | 3/1993 |
| WO | WO 94/05786 | 3/1994 |
| WO | WO 94/24870 | 11/1994 |
| WO | WO 96/11013 | 4/1996 |
| WO | WO99/14310 | 3/1999 |
| WO | WO 99/43795 | 9/1999 |

OTHER PUBLICATIONS

Mehtali et al., Gene 91:179-84 [1990].
Kricker et al., Proc. Natl. Acad. Sci. 89:1075-79 [1992].
Dorer and Henikoff, Cell 77:993-1002 [1994].
Anderson and Young, Quantitative Filter Hybridization, in *Nucleic Acid Hybridization* [1985].
Sambrook, J. et al., *Molecular Cloning: A Laboratory Manual*, 2nd ed., Cold Spring Harbor Laboratory Press, New York (1989) pp. 16.9-16.15.
Maniatis et al., Science 236:1237 [1987].
Voss et al., Trends Biochem. Sci., 11:287 [1986].
Dijkema et al., EMBO J. 4:761 [1985].
Uetsuki et al., J. Biol. Chem., 264:5791 [1989].
Kim et al., Gene 91:217 [1990].
Mizushima and Nagata, Nuc. Acids. Res., 18:5322 [1990].
Gorman et al., Proc. Natl. Acad. Sci. USA 79:6777 [1982].
Boshart et al., Cell 41:521 [1985].
Sambrook et al., *Molecular Cloning: A Laboratory Manual*, 2nd ed., Cold Spring Harbor Laboratory Press, New York [1989], pp. 16.7-16.8.
Zwizinski et al., J. Biol. Chem. 255(16): 7973-77 [1980].
Gray et al., Gene 39(2): 247-54 [1985].
Martial et al., Science 205: 602-607 [1979].
Shelling and Smith, Gene Therapy 1:165-169 [1994].
Zhou et al., J. Exp. Med. 179:1867-1875 [1994].
Han et al., Proc. Natl. Acad. Sci. USA 88:4313-4317 [1991].
Uhlmann et al., Chem. Rev. 90:543-584 [1990].
Helene et al., Biochim. Biophys. Acta. 1049:99-125 [1990].
Agarwal et al., Proc. Natl. Acad. Sci. USA 85:7079-7083 [1989].
Heikkila et al., Nature 328:445-449 [1987].
Cech et al. (1992) J. Biol. Chem. 267:17479-17482.
Kotin, Human Gene Therapy 5:793-801 [1994].
Berns, K.I. "Parvoviridae and their Replication" in Fundamental Virology, 2nd Edition, (B.N. Fields and D.M. Knipe, eds.).
Ullrich and Schlessinger, Cell 61:203-212 [1990].
Neer, 1995, Cell 80:249-257 [1995].
Sternweis and Smrcka, Trends in Biochem. Sci. 17:502-506 [1992].
Carbonneau, H. and Tonks, Annu. Rev. Cell Biol. 8:463-93 [1992].
Cole et al., in *Monoclonal Antibodies and Cancer Therapy*, Alan R. Liss, Inc., pp. 77-96 [1985].
Krueger et al., Proc. Natl. Acad. Sci. USA 89:7417-7421 [1992].
Köhler and Milstein, Nature 256:495-497 [1975].
Kozbor et al. Immunol. Today 4:72 [1983].
Cole et al., in *Monoclonal Antibodies and Cancer Therapy*, Alan R. Liss, Inc., pp. 77-96 [1985].
Huse et al., Science 246:1275-1281 [1989].
deWet et al., Mol. Cell. Biol. 7:725 [1987].
Graham et al., J. Gen Virol., 36:59 [1977].
Mather, Biol. Reprod. 23:243-251 [1980].
Mather et al., Annals N.Y. Acad. Sci., 383:44-68 [1982].
Evans et al., *Handbook of Plant Cell Culture*, 1: 124-176, MacMillan Publishing Co., New York [1983].
Binding, *Plant Protoplasts*, p. 21-37, CRC Press, Boca Raton [1985].
Potrykus and Shillito, *Methods in Enzymology*, vol. 118, Plant Molecular Biology, A. and H. Weissbach eds., Academic Press, Orlando [1986].
Hoess et al., Nucleic Acids Res. 14:2287-2300 [1986].
O'Gorman et al., Science 251:1351-55 [1991].
van Deursen et al., Proc. Natl. Acad. Sci. USA 92:7376-80 [1995.
Miller and Baltimore Mol. Cell. Biol. 6:2895 [1986].
Markowitz et al., J. Virol. 62:1120 [1988]).
Miller et al., Mol. Cell. Biol. 10:4239 [1990].
Miller and Rosman, BioTechniques 7: 980 [1980].
Miller, Nature 357: 455 [1990].
Adams et al., Proc. Natl. Acad. Sci. USA 89:8981 [1992].
Mastromarino et al., J. Gen. Virol. 68:2359 [1977].
Burns et al. Proc. Natl. Acad. Sci. USA 90:8033 [1993].
Roe et al., EMBO J. 12:2099 [1993].
Naldini et al., Science 272:263 [1996].
Carter, B.J., Current Opinion in Biotechnology 3:533-539 [1992].
de la Cruz et al., J. Bact. 175: 6932-38 [1993].
Craig, Curr. Topics Microbiol. Immunol. 204: 27-48 [1996].
Morisato and Kleckner, Cell 51:101-111 [1987].
Cleveland et al., J. Immunol. Methods 56:221-234 [1983], *Animal Cell Culture: A Practical Approach 2nd Ed.*, Rickwood, D. and Hames, B. D., eds. Oxford University Press, New York [1992].
Wilson et al., Cell, 37:767 [1984].
Schroeder and Neagle, J. Biomol. Screening 1:75-80 [1996].
Denyer et al., Drug Discov. Today 3:323-32 [1998].
Gonzales et al., Drug. Discov. Today 4:431-39 [1999].
Graham and Van der Eb, Virol. 52:456 [1973].
Goff et al., J. Virol. 38:239 [1981].
Quade, Virol. 98:461 [1979].
Yee et al., Meth. Cell Biol. 43:99 [1994].
Chen and Okayama (Mol. Cell. Biol., 7:2745, 1987.
Shillito, et al., Plant Cell Reports, 2, 244-247 (1983).
Brun et al., Intervirol, 38:274 (1995).
Masters et al., Virol. 171:285 (1990).

Mebatsion et al., J. Virol. 69:1444 (1995).
Scheper et al., Biochem. 76: 801-809 [1994].
Meyer et al., J. Virol. 69: 2819-2824 [1995].
Jang et al., 1988, J. Virol. 62: 2636-2643 [1998].
Haller et al., J. Virol. 66: 5075-5086 [1995].
Lebkowski et al., Molec. Cell. Biol. 8:3988-3996 [1988].
Vincent et al. Vaccines 90 [1990].
Carter, Current Opinion in Biotechnology 3:533-539 [1992].
Muzyczka, Current Topics in Microbiol. and Immunol. 158:97-129 [1992].
Rogers et al., Strategies 13:97-99 (2000).
Felts et al., Strategies 13:15-18 (2000).
Felts et al., Strategies 12:74-77 (1999).
Poul et al., Immunotechnology, Elsevier Science Publishers BV, NL 1:189-196 (1995).
Zufferey et al., J. of Virology 73:2886-2892 (1999).
Wang et al., Gene 182:145-150 (1996).
Vaillancourt et al., Strategies 13:50-53 (2000).
Han et al., PNAS 88:4313-4317 (1991).

\* cited by examiner

Figure 4
SEQ ID NO:1
Hybrid Human-Bovine Alpha-Lactalbumin Promoter

```
1     GATCAGTCCTGGGTGGTCATTGAAAGGACTGATGCTGAAGTTGAAGCTCC
51    AATACTTTGGCCACCTGATGCGAAGAACTGACTCATGTGATAAGACCCTG
101   ATACTGGGAAAGATTGAAGGCAGGAGGAGAAGGGATGACAGAGGATGGAA
151   GAGTTGGATGGAATCACCAACTCGATGGACATGAGTTTGAGCAAGCTTCC
201   AGGAGTTGGTAATGGGCAGGGAAGCCTGGCGTGCTGCAGTCCATGGGGTT
251   GCAAAGAGTTGGACACTACTGAGTGACTGAACTGAACTGATAGTGTAATC
301   CATGGTACAGAATATAGGATAAAAAAGAGGAAGAGTTTGCCCTGATTCTG
351   AAGAGTTGTAGGATATAAAAGTTTAGAATACCTTTAGTTTGGAAGTCTTA
401   AATTATTTACTTAGGATGGGTACCCACTGCAATATAAGAAATCAGGCTTT
451   AGAGACTGATGTAGAGAGAATGAGCCCTGGCATACCAGAAGCTAACAGCT
501   ATTGGTTATAGCTGTTATAACCAATATATAACCAATATATTGGTTATATA
551   GCATGAAGCTTGATGCCAGCAATTTGAAGGAACCATTTAGAACTAGTATC
601   CTAAACTCTACATGTTCCAGGACACTGATCTTAAAGCTCAGGTTCAGAAT
651   CTTGTTTTATAGGCTCTAGGTGTATATTGTGGGGCTTCCCTGGTGGCTCA
701   GATGGTAAAGTGTCTGCCTGCAATGTGGGTGATCTGGGTTCGATCCCTGG
751   CTTGGGAAGATCCCCTGGAGAAGGAAATGGCAACCCACTCTAGTACTCTT
801   ACCTGGAAAATTCCATGGACAGAGGAGCCTTGTAAGCTACAGTCCATGGG
851   ATTGCAAAGAGTTGAACACAACTGAGCAACTAAGCACAGCACAGTACAGT
900   ATACACCTGTGAGGTGAAGTGAAGTGAAGGTTCAATGCAGGGTCTCCTGC
951   ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACACTTTTCAAGTTCTCCATTTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGTTCTGGGCCTTGTTACATGGC
1551  TGGATTGGTTGGACAAGTGCCAGCTCTGATCCTGGGACTGTGGCATGTGA
1601  TGACATACACCCCCTCTCCACATTCTGCATGTCTCTAGGGGGGAAGGGGG
1651  AAGCTCGGTATAGAACCTTTATTGTATTTTCTGATTGCCTCACTTTCTTAT
1701  ATTGCCCCCATGCCCTTCTTTGTTCCTCAAGTAACCAGAGACAGTGCTTC
1751  CCAGAACCAACCCTACAAGAAACAAAGGGCTAAACAAAGCCAAATGGGAA
1801  GCAGGATCATGGTTTGAACTCTTTCTGGCCAGAGAACAATACCTGCTATG
1851  GACTAGATACTGGGAGAGGGAAAGGAAAAGTAGGGTGAATTATGGAAGGA
1901  AGCTGGCAGGCTCAGCGTTTCTGTCTTGGCATGACCAGTCTCTCTTCATT
1951  CTCTTCCTAGATGTAGGGCTTGGTACCAGAGCCCCTGAGGCTTTCTGCAT
2001  GAATATAAATATATGAAACTGAGTGATGCTTCCATTTCAGGTTCTTGGGG
2051  GCGCCGAATTCGAGCTCGGTACCCGGGGATCTCGAGGGGGGGCCCGGTAC
2101  C
```

1 - 1525    Bovine alpha lactalbumin 5' flanking region (-2000 to -550 from the bovine alpha-lactalbumin transcription start point)
1526 - 2056  Human alpha-lactalbumin 5' flanking region (-600 to +15 from the human alpha-lactalbumin transcription start point)
2057 - 2101  Multiple cloning site Figure 5
SEQ ID NO:2
Mutated PPE Sequence

```
1    GATTACTTACTGGCAGGTGCTGGGGGCTTCCGAGACAATCGCGAACATCT
51   ACACCACACAACACCGCCTCGACCAGGGTGAGATATCGGCCGGGGACGCG
101  GCGGTGGTAATTACAAGCGAGGATCCGATTACTTACTGGCAGGTGCTGGG
151  GGCTTCCGAGACAATCGCGAACATCTACACCACACAACACCGCCTCGACC
201  AGGGTGAGATATCGGCCGGGGACGCGGCGGTGGTAATTACAAGCG
```

| | |
|---|---|
| 1 - 119 | Mutated PPE |
| 120 -126 | Linker |
| 127 - 245 | Mutated PPE |

Figure 6
SEQ ID NO:3
IRES-Signal Peptide Sequence

```
1    GGAATTCGCCCCTCTCCCTCCCCCCCCCTAACGTTACTGGCCGAAGCCG
51   CTTGGAATAAGGCCGGTGTGCGTTTGTCTATATGTTATTTTCCACCATAT
101  TGCCGTCTTTTGGCAATGTGAGGGCCCGGAAACCTGGCCCTGTCTTCTTG
151  ACGAGCATTCCTAGGGGTCTTTCCCCTCTCGCCAAAGGAATGCAAGGTCT
201  GTTGAATGTCGTGAAGGAAGCAGTTCCTCTGGAAGCTTCTTGAAGACAAA
251  CAACGTCTGTAGCGACCCTTTGCAGGCAGCGGAACCCCCCACCTGGCGAC
301  AGGTGCCTCTGCGGCCAAAAGCCACGTGTATAAGATACACCTGCAAAGGC
351  GGCACAACCCCAGTGCCACGTTGTGAGTTGGATAGTTGTGGAAAGAGTCA
401  AATGGCTCTCCTCAAGCGTATTCAACAAGGGGCTGAAGGATGCCCAGAAG
451  GTACCCCATTGTATGGGATCTGATCTGGGGCCTCGGTGCACATGCTTTAC
501  ATGTGTTTAGTCGAGGTTAAAAAAACGTCTAGGCCCCCCGAACCACGGGG
551  ACGTGGTTTTCCTTTGAAAAACACGATGATAATATGGCCTCCTTTGTCTC
601  TCTGCTCCTGGTAGGCATCCTATTCCATGCCACCCAGGCCGGCGCCATGG
651  GATATCTAGATCTCGAGCTCGCGAAGCTT
```

| | |
|---|---|
| 1 - 583 | IRES |
| 584 - 640 | Modified bovine alpha-lactalbumin signal peptide coding region |
| 641 - 680 | Multiple cloning site |

Figure 7a
SEQ ID NO:4
CMV MN14 Vector

```
   1  CGGATCCGGCCATTAGCCATATTATTCATTGGTTATATAGCATAAATCAA
  51  TATTGGCTATTGGCCATTGCATACGTTGTATCCATATCATAATATGTACA
 101  TTTATATTGGCTCATGTCCAACATTACCGCCATGTTGACATTGATTATTG
 151  ACTAGTTATTAATAGTAATCAATTACGGGGTCATTAGTTCATAGCCCATA
 201  TATGGAGTTCCGCGTTACATAACTTACGGTAAATGGCCCGCCTGGCTGAC
 251  CGCCCAACGACCCCCGCCCATTGACGTCAATAATGACGTATGTTCCCATA
 301  GTAACGCCAATAGGGACTTTCCATTGACGTCAATGGGTGGAGTATTTACG
 351  GTAAACTGCCCACTTGGCAGTACATCAAGTGTATCATATGCCAAGTACGC
 401  CCCCTATTGACGTCAATGACGGTAAATGGCCCGCCTGGCATTATGCCCAG
 451  TACATGACCTTATGGGACTTTCCTACTTGGCAGTACATCTACGTATTAGT
 501  CATCGCTATTACCATGGTGATGCGGTTTTGGCAGTACATCAATGGGCGTG
 551  GATAGCGGTTTGACTCACGGGGATTTCCAAGTCTCCACCCCATTGACGTC
 601  AATGGGAGTTTGTTTTGGCACCAAAATCAACGGGACTTTCCAAAATGTCG
 651  TAACAACTCCGCCCCATTGACGCAAATGGGCGGTAGGCATGTACGGTGGG
 701  AGGTCTATATAAGCAGAGCTCGTTTAGTGAACCGTCAGATCGCCTGGAGA
 751  CGCCATCCACGCTGTTTTGACCTCCATAGAAGACACCGGGACCGATCCAG
 801  CCTCCGCGGCCCCAAGCTTCTCGACGGATCCCCGGGAATTCAGGACCTCA
 851  CCATGGGATGGAGCTGTATCATCCTCTTCTTGGTAGCAACAGCTACAGGT
 901  GTCCACTCCGAGGTCCAACTGGTGGAGAGCGGTGGAGGTGTTGTGCAACC
 951  TGGCCGGTCCCTGCGCCTGTCCTGCTCCGCATCTGGCTTCGATTTCACCA
1001  CATATTGGATGAGTTGGGTGAGACAGGCACCTGGAAAAGGTCTTGAGTGG
1051  ATTGGAGAAATTCATCCAGATAGCAGTACGATTAACTATGCGCCGTCTCT
1101  AAAGGATAGATTTACAATATCGCGAGACAACGCCAAGAACACATTGTTCC
1151  TGCAAATGGACAGCCTGAGACCCGAAGACACCGGGGTCTATTTTGTGCA
1201  AGCCTTTACTTCGGCTTCCCCTGGTTTGCTTATTGGGGCCAAGGGACCCC
1251  GGTCACCGTCTCCTCAGCCTCCACCAAGGGCCCATCGGTCTTCCCCCTGG
1301  CACCCTCCTCCAAGAGCACCTCTGGGGGCACAGCGGCCCTGGGCTGCCTG
1351  GTCAAGGACTACTTCCCCGAACCGGTGACGGTGTCGTGGAACTCAGGCGC
1401  CCTGACCAGCGGCGTGCACACCTTCCCGGCTGTCCTACAGTCCTCAGGAC
1451  TCTACTCCCTCAGCAGCGTGGTGACCGTGCCCTCCAGCAGCTTGGGCACC
1501  CAGACCTACATCTGCAACGTGAATCACAAGCCCAGCAACACCAAGGTGGA
1551  CAAGAGAGTTGAGCCCAAATCTTGTGACAAAACTCACACATGCCCACCGT
1601  GCCCAGCACCTGAACTCCTGGGGGGACCGTCAGTCTTCCTCTTCCCCCCA
1651  AAACCCAAGGACACCCTCATGATCTCCCGGACCCCTGAGGTCACATGCGT
1701  GGTGGTGGACGTGAGCCACGAAGACCCTGAGGTCAAGTTCAACTGGTACG
1751  TGGACGGCGTGGAGGTGCATAATGCCAAGACAAAGCCGCGGGAGGAGCAG
1801  TACAACAGCACGTACCGTGTGGTCAGCGTCCTCACCGTCCTGCACCAGGA
1851  CTGGCTGAATGGCAAGGAGTACAAGTGCAAGGTCTCCAACAAAGCCCTCC
1901  CAGCCCCCATCGAGAAAACCATCTCCAAAGCCAAAGGGCAGCCCCGAGAA
1951  CCACAGGTGTACACCCTGCCCCCATCCCGGGAGGAGATGACCAAGAACCA
2001  GGTCAGCCTGACCTGCCTGGTCAAAGGCTTCTATCCCAGCGACATCGCCG
2051  TGGAGTGGGAGAGCAATGGGCAGCCGGAGAACAACTACAAGACCACGCCT
2101  CCCGTGCTGGACTCCGACGGCTCCTTCTTCCTCTATAGCAAGCTCACCGT
2151  GGACAAGAGCAGGTGGCAGCAGGGGAACGTCTTCTCATGCTCCGTGATGC
2201  ACGAGGCTCTGCACAACCACTACACGCAGAAGAGCCTCTCCCTGTCTCCC
2251  GGGAAATGAAAGCCGAATTCGCCCCTCTCCCTCCCCCCCCCCTAACGTTA
2301  CTGGCCGAAGCCGCTTGGAATAAGGCCGGTGTGCGTTTGTCTATATGTTA
2351  TTTTCCACCATATTGCCGTCTTTTGGCAATGTGAGGGCCCGGAAACCTGG
2401  CCCTGTCTTCTTGACGAGCATTCCTAGGGGTCTTTCCCCTCTCGCCAAAG
2451  GAATGCAAGGTCTGTTGAATGTCGTGAAGGAAGCAGTTCCTCTGGAAGCT
2501  TCTTGAAGACAAACAACGTCTGTAGCGACCCTTTGCAGGCAGCGGAACCC
2551  CCCACCTGGCGACAGGTGCCTCTGCGGCCAAAAGCCACGTGTATAAGATA
2601  CACCTGCAAAGGCGGCACAACCCCAGTGCCACGTTGTGAGTTGGATAGTT
2651  GTGGAAAGAGTCAAATGGCTCTCCTCAAGCGTATTCAACAAGGGGCTGAA
2701  GGATGCCCAGAAGGTACCCCATTGTATGGGATCTGATCTGGGGCCTCGGT
2751  GCACATGCTTTACATGTGTTTAGTCGAGGTTAAAAAAACGTCTAGGCCCC
2801  CCGAACCACGGGGACGTGGTTTTCCTTTGAAAAACACGATGATAATATGG
```

Figure 7b

```
2851  CCTCCTTTGTCTCTCTGCTCCTGGTAGGCATCCTATTCCATGCCACCCAG
2901  GCCGACATCCAGCTGACCCAGAGCCCAAGCAGCCTGAGCGCCAGCGTGGG
2951  TGACAGAGTGACCATCACCTGTAAGGCCAGTCAGGATGTGGGTACTTCTG
3001  TAGCCTGGTACCAGCAGAAGCCAGGTAAGGCTCCAAAGCTGCTGATCTAC
3051  TGGACATCCACCCGGCACACTGGTGTGCCAAGCAGATTCAGCGGTAGCGG
3101  TAGCGGTACCGACTTCACCTTCACCATCAGCAGCCTCCAGCCAGAGGACA
3151  TCGCCACCTACTACTGCCAGCAATATAGCCTCTATCGGTCGTTCGGCCAA
3201  GGGACCAAGGTGGAAATCAAACGAACTGTGGCTGCACCATCTGTCTTCAT
3251  CTTCCCGCCATCTGATGAGCAGTTGAAATCTGGAACTGCCTCTGTTGTGT
3301  GCCTGCTGAATAACTTCTATCCCAGAGAGGCCAAAGTACAGTGGAAGGTG
3351  GATAACGCCCTCCAATCGGGTAACTCCCAGGAGAGTGTCACAGAGCAGGA
3401  CAGCAAGGACAGCACCTACAGCCTCAGCAGCACCCTGACGCTGAGCAAAG
3451  CAGACTACGAGAAACACAAAGTCTACGCCTGCGAAGTCACCCATCAGGGC
3501  CTGAGCTCGCCCGTCACAAAGAGCTTCAACAGGGGAGAGTGTTAGAGATC
3551  TAGGCCTCCTAGGTCGACATCGATAAAATAAAAGATTTTATTTAGTCTCC
3601  AGAAAAGGGGGGAATGAAAGACCCCACCTGTAGGTTTGGCAAGCTAGCT
3651  TAAGTAACGCCATTTTGCAAGGCATGGAAAATACATAACTGAGAATAGA
3701  GAAGTTCAGATCAAGGTCAGGAACAGATGGAACAGCTGAATATGGGCCAA
3751  ACAGGATATCTGTGGTAAGCAGTTCCTGCCCCGGCTCAGGGCCAAGAACA
3801  GATGGAACAGCTGAATATGGGCCAAACAGGATATCTGTGGTAAGCAGTTC
3851  CTGCCCCGGCTCAGGGCCAAGAACAGATGGTCCCCAGATGCGGTCCAGCC
3901  CTCAGCAGTTTCTAGAGAACCATCAGATGTTTCCAGGGTGCCCCAAGGAC
3951  CTGAAATGACCCTGTGCCTTATTTGAACTAACCAATCAGTTCGCTTCTCG
4001  CTTCTGTTCGCGCGCTTCTGCTCCCCGAGCTCAATAAAAGAGCCCACAAC
4051  CCCTCACTCGGGGCGCCAGTCCTCCGATTGACTGAGTCGCCCGGGTACCC
4101  GTGTATCCAATAAACCCTCTTGCAGTTGCATCCGACTTGTGGTCTCGCTG
4151  TTCCTTGGGAGGGTCTCCTCTGAGTGATTGACTACCCGTCAGCGGGGGTC
4201  TTTCATT
```

| | |
|---|---|
| 1 - 812 | CMV promoter/enhancer |
| 853-855 | MN14 antibody heavy chain gene signal peptide start codon |
| 2257 - 2259 | MN14 antibody heavy chain gene start codon |
| 2271 - 2846 | EMCV IRES |
| 2847 - 2849 | Bovine alpha-lactalbumin signal peptide start codon |
| 2904 - 2906 | First codon mature MN14 antibody light chain gene |
| 3543 - 3544 | MN14 antibody light chain gene stop codon |
| 3614 - 4207 | MoMuLV 3' LTR |

Figure 8a
SEQ ID NO:5
CMV LL2 Vector

```
   1 GGATCCGGCCATTAGCCATATTATTCATTGGTTATATAGCATAAATCAAT
  51 ATTGGCTATTGGCCATTGCATACGTTGTATCCATATCATAATATGTACAT
 101 TTATATTGGCTCATGTCCAACATTACCGCCATGTTGACATTGATTATTGA
 151 CTAGTTATTAATAGTAATCAATTACGGGGTCATTAGTTCATAGCCCATAT
 201 ATGGAGTTCCGCGTTACATAACTTACGGTAAATGGCCCGCCTGGCTGACC
 251 GCCCAACGACCCCCGCCCATTGACGTCAATAATGACGTATGTTCCCATAG
 301 TAACGCCAATAGGGACTTTCCATTGACGTCAATGGGTGGAGTATTTACGG
 351 TAAACTGCCCACTTGGCAGTACATCAAGTGTATCATATGCCAAGTACGCC
 401 CCCTATTGACGTCAATGACGGTAAATGGCCCGCCTGGCATTATGCCCAGT
 451 ACATGACCTTATGGGACTTTCCTACTTGGCAGTACATCTACGTATTAGTC
 501 ATCGCTATTACCATGGTGATGCGGTTTTGGCAGTACATCAATGGGCGTGG
 551 ATAGCGGTTTGACTCACGGGGATTTCCAAGTCTCCACCCCATTGACGTCA
 601 ATGGGAGTTTGTTTTGGCACCAAAATCAACGGGACTTTCCAAAATGTCGT
 651 AACAACTCCGCCCCATTGACGCAAATGGGCGGTAGGCATGTACGGTGGGA
 701 GGTCTATATAAGCAGAGCTCGTTTAGTGAACCGTCAGATCGCCTGGAGAC
 751 GCCATCCACGCTGTTTTGACCTCCATAGAAGACACCGGGACCGATCCAGC
 801 CTCCGCGGCCCCAAGCTTCTCGACGGATCCCGGGAATTCAGGACCTCAC
 851 CATGGGATGGAGCTGTATCATCCTCTTCTTGGTAGCAACAGCTACAGGTG
 901 TCCACTCCCAGGTCCAGCTGGTCCAATCAGGGGCTGAAGTCAAGAAACCT
 951 GGGTCATCAGTGAAGGTCTCCTGCAAGGCTTCTGGCTACACCTTTACTAG
1001 CTACTGGCTGCACTGGGTCAGGCAGGCACCTGGACAGGGTCTGGAATGGA
1051 TTGGATACATTAATCCTAGGAATGATTATACTGAGTACAATCAGAACTTC
1101 AAGGACAAGGCCACAATAACTGCAGACGAATCCACCAATACAGCCTACAT
1151 GGAGCTGAGCAGCCTGAGGTCTGAGGACACGGCATTTTATTTTTGTGCAA
1201 GAAGGGATATTACTACGTTCTACTGGGGCCAAGGCACCACGGTCACCGTC
1251 TCCTCAGCCTCCACCAAGGGCCCATCGGTCTTCCCCCTGGCACCCTCCTC
1301 CAAGAGCACCTCTGGGGGCACAGCGGCCCTGGGCTGCCTGGTCAAGGACT
1351 ACTTCCCCGAACCGGTGACGGTGTCGTGGAACTCAGGCGCCCTGACCAGC
1401 GGCGTGCACACCTTCCCGGCTGTCCTACAGTCCTCAGGACTCTACTCCCT
1451 CAGCAGCGTGGTGACCGTGCCCTCCAGCAGCTTGGGCACCCAGACCTACA
1501 TCTGCAACGTGAATCACAAGCCCAGCAACACCAAGGTGGACAAGAGAGTT
1551 GAGCCCAAATCTTGTGACAAAACTCACACATGCCCACCGTGCCCAGCACC
1601 TGAACTCCTGGGGGGACCGTCAGTCTTCCTCTTCCCCCCAAAACCCAAGG
1651 ACACCCTCATGATCTCCCGGACCCCTGAGGTCACATGCGTGGTGGTGGAC
1701 GTGAGCCACGAAGACCCTGAGGTCAAGTTCAACTGGTACGTGGACGGCGT
1751 GGAGGTGCATAATGCCAAGACAAAGCCGCGGGAGGAGCAGTACAACAGCA
1801 CGTACCGTGTGGTCAGCGTCCTCACCGTCCTGCACCAGGACTGGCTGAAT
1851 GGCAAGGAGTACAAGTGCAAGGTCTCCAACAAAGCCCTCCCAGCCCCCAT
1901 CGAGAAAACCATCTCCAAAGCCAAAGGGCAGCCCCGAGAACCACAGGTGT
1951 ACACCCTGCCCCCATCCCGGGAGGAGATGACCAAGAACCAGGTCAGCCTG
2001 ACCTGCCTGGTCAAAGGCTTCTATCCCAGCGACATCGCCGTGGAGTGGGA
2051 GAGCAATGGGCAGCCGGAGAACAACTACAAGACCACGCCTCCCGTGCTGG
2101 ACTCCGACGGCTCCTTCTTCCTCTATAGCAAGCTCACCGTGGACAAGAGC
2151 AGGTGGCAGCAGGGGAACGTCTTCTCATGCTCCGTGATGCACGAGGCTCT
2201 GCACAACCACTACACGCAGAAGAGCCTCTCCCTGTCTCCCGGGAAATGAA
2251 AGCCGAATTCGCCCCTCTCCCTCCCCCCCCCTAACGTTACTGGCCGAAG
2301 CCGCTTGGAATAAGGCCGGTGTGCGTTTGTCTATATGTTATTTTCCACCA
2351 TATTGCCGTCTTTTGGCAATGTGAGGGCCCGGAAACCTGGCCCTGTCTTC
2401 TTGACGAGCATTCCTAGGGGTCTTTCCCCTCTCGCCAAAGGAATGCAAGG
2451 TCTGTTGAATGTCGTGAAGGAAGCAGTTCCTCTGGAAGCTTCTTGAAGAC
2501 AAACAACGTCTGTAGCGACCCTTTGCAGGCAGCGGAACCCCCCACCTGGC
2551 GACAGGTGCCTCTGCGGCCAAAAGCCACGTGTATAAGATACACCTGCAAA
2601 GGCGGCACAACCCCAGTGCCACGTTGTGAGTTGGATAGTTGTGGAAAGAG
2651 TCAAATGGCTCTCCTCAAGCGTATTCAACAAGGGGCTGAAGGATGCCCAG
2701 AAGGTACCCCATTGTATGGGATCTGATCTGGGGCCTCGGTGCACATGCTT
2751 TACATGTGTTTAGTCGAGGTTAAAAAAACGTCTAGGCCCCCCGAACCACG
2801 GGGACGTGGTTTTCCTTTGAAAAACACGATGATAATATGGCCTCCTTTGT
```

Figure 8b

```
2851   CTCTCTGCTCCTGGTAGGCATCCTATTCCATGCCACCCAGGCCGACATCC
2901   AGCTGACCCAGTCTCCATCATCTCTGAGCGCATCTGTTGGAGATAGGGTC
2951   ACTATGAGCTGTAAGTCCAGTCAAAGTGTTTTATACAGTGCAAATCACAA
3001   GAACTACTTGGCCTGGTACCAGCAGAAACCAGGGAAAGCACCTAAACTGC
3051   TGATCTACTGGGCATCCACTAGGGAATCTGGTGTCCCTTCGCGATTCTCT
3101   GGCAGCGGATCTGGGACAGATTTTACTTTCACCATCAGCTCTCTTCAACC
3151   AGAAGACATTGCAACATATTATTGTCACCAATACCTCTCCTCGTGGACGT
3201   TCGGTGGAGGGACCAAGGTGCAGATCAAACGAACTGTGGCTGCACCATCT
3251   GTCTTCATCTTCCCGCCATCTGATGAGCAGTTGAAATCTGGAACTGCCTC
3301   TGTTGTGTGCCTGCTGAATAACTTCTATCCCAGAGAGGCCAAAGTACAGT
3351   GGAAGGTGGATAACGCCCTCCAATCGGGTAACTCCCAGGAGAGTGTCACA
3401   GAGCAGGACAGCAAGGACAGCACCTACAGCCTCAGCAGCACCCTGACGCT
3451   GAGCAAAGCAGACTACGAGAAACACAAAGTCTACGCCTGCGAAGTCACCC
3501   ATCAGGGCCTGAGCTCGCCCGTCACAAAGAGCTTCAACAGGGGAGAGTGT
3551   TAGAGATCTAGGCCTCCTAGGTCGACATCGATAAAATAAAAGATTTATT
3601   TAGTCTCCAGAAAAGGGGGGAATGAAAGACCCCACCTGTAGGTTTGGCA
3651   AGCTAGCTTAAGTAACGCCATTTTGCAAGGCATGGAAAATACATAACTG
3701   AGAATAGAGAAGTTCAGATCAAGGTCAGGAACAGATGGAACAGCTGAATA
3751   TGGGCCAAACAGGATATCTGTGGTAAGCAGTTCCTGCCCCGGCTCAGGGC
3801   CAAGAACAGATGGAACAGCTGAATATGGGCCAAACAGGATATCTGTGGTA
3851   AGCAGTTCCTGCCCCGGCTCAGGGCCAAGAACAGATGGTCCCCAGATGCG
3901   GTCCAGCCCTCAGCAGTTTCTAGAGAACCATCAGATGTTTCCAGGGTGCC
3951   CCAAGGACCTGAAATGACCCTGTGCCTTATTTGAACTAACCAATCAGTTC
4001   GCTTCTCGCTTCTGTTCGCGCGCTTCTGCTCCCGAGCTCAATAAAAGAG
4051   CCCACAACCCCTCACTCGGGGCGCCAGTCCTCCGATTGACTGAGTCGCCC
4101   GGGTACCCGTGTATCCAATAAACCCTCTTGCAGTTGCATCCGACTTGTGG
4151   TCTCGCTGTTCCTTGGGAGGGTCTCCTCTGAGTGATTGACTACCCGTCAG
4201   GTCTTTCATT
```

| | |
|---|---|
| 1 - 812 | CMV promoter/enhancer |
| 852 - 854 | LL2 antibody heavy chain signal peptide start codon |
| 2247 - 2249 | LL2 antibody heavy chain stop codon |
| 2261 - 2836 | EMCV IRES |
| 2837 - 2839 | Bovine alpha-lactalbumin signal peptide start codon |
| 2894 - 2896 | First codon of mature LL2 antibody light chain gene |
| 3551 - 3553 | LL2 antibody light chain gene stop codon |
| 3622 - 4210 | MoMuLV 3' LTR |

Figure 9a
SEQ ID NO:6
MMTV MN14 Vector

```
   1  CGAGCTTGGCAGAAATGGTTGAACTCCCGAGAGTGTCCTACACCTAGGGG
  51  AGAAGCAGCCAAGGGGTTGTTTCCCACCAAGGACGACCCGTCTGCGCACA
 101  AACGGATGAGCCCATCAGACAAAGACATATTCATTCTCTGCTGCAAACTT
 151  GGCATAGCTCTGCTTTGCCTGGGGCTATTGGGGGAAGTTGCGGTTCGTGC
 201  TCGCAGGGCTCTCACCCTTGACTCTTTCAATAATAACTCTTCTGTGCAAG
 251  ATTACAATCTAAACAATTCGGAGAACTCGACCTTCCTCCTGAGGCAAGGA
 301  CCACAGCCAACTTCCTCTTACAAGCCGCATCGATTTGTCCTTCAGAAAT
 351  AGAAATAAGAATGCTTGCTAAAAATTATATTTTTACCAATAAGACCAATC
 401  CAATAGGTAGATTATTAGTTACTATGTTAAGAAATGAATCATTATCTTTT
 451  AGTACTATTTTTACTCAAATTCAGAAGTTAGAAATGGGAATAGAAAATAG
 501  AAAGAGACGCTCAACCTCAATTGAAGAACAGGTGCAAGGACTATTGACCA
 551  CAGGCCTAGAAGTAAAAAAGGGAAAAAGAGTGTTTTTGTCAAAATAGGA
 601  GACAGGTGGTGGCAACCAGGGACTTATAGGGGACCTTACATCTACAGACC
 651  AACAGATGCCCCCTTACCATATACAGGAAGATATGACTTAAATTGGGATA
 701  GGTGGGTTACAGTCAATGGCTATAAAGTGTTATATAGATCCCTCCCCTTT
 751  CGTGAAAGACTCGCCAGAGCTAGACCTCCTTGGTGTATGTTGTCTCAAGA
 801  AAAGAAAGACGACATGAAACAACAGGTACATGATTATATTTATCTAGGAA
 851  CAGGAATGCACTTTTGGGGAAAGATTTTCCATACCAAGGAGGGGACAGTG
 901  GCTGGACTAATAGAACATTATTCTGCAAAAACTTATGGCATGAGTTATTA
 951  TGATTAGCCTTGATTTGCCCAACCTTGCGGTTCCCAAGGCTTAAGTAAGT
1001  TTTTGGTTACAAACTGTTCTTAAAACAAGGATGTGAGACAAGTGGTTTCC
1051  TGACTTGGTTTGGTATCAAAGGTTCTGATCTGAGCTCTGAGTGTTCTATT
1101  TTCCTATGTTCTTTTGGAATTTATCCAAATCTTATGTAAATGCTTATGTA
1151  AACCAAGATATAAAAGAGTGCTGATTTTTTGAGTAAACTTGCAACAGTCC
1201  TAACATTCACCTCTTGTGTGTTTGTGTCTGTTCGCCATCCCGTCTCCGCT
1251  CGTCACTTATCCTTCACTTTCCAGAGGGTCCCCCCGCAGACCCCGGCGAC
1301  CCTCAGGTCGGCCGACTGCGGCAGCTGGCCCCGAACAGGGACCCTCGGA
1351  TAAGTGACCCTTGTCTTTATTTCTACTATTTTGTGTTCGTCTTGTTTTGT
1401  CTCTATCTTGTCTGGCTATCATCACAAGAGCGGAACGGACTCACCTCAGG
1451  GAACCAAGCTAGCCCGGGGTCGACGGATCCGATTACTTACTGGCAGGTGC
1501  TGGGGGCTTCCGAGACAATCGCGAACATCTACACCACACAACACCGCCTC
1551  GACCAGGGTGAGATATCGGCCGGGGACGCGGCGGTGGTAATTACAAGCGA
1601  GATCCGATTACTTACTGGCAGGTGCTGGGGGCTTCCGAGACAATCGCGAA
1651  CATCTACACCACACAACACCGCCTCGACCAGGGTGAGATATCGGCCGGGG
1701  ACGCGGCGGTGGTAATTACAAGCGAGATCCCCGGGAATTCAGGACCTCAC
1751  CATGGGATGGAGCTGTATCATCCTCTTCTTGGTAGCAACAGCTACAGGTG
1801  TCCACTCCGAGGTCCAACTGGTGGAGAGCGGTGGAGGTGTTGTGCAACCT
1851  GGCCGGTCCCTGCGCCTGTCCTGCTCCGCATCTGGCTTCGATTTCACCAC
1901  ATATTGGATGAGTTGGGTGAGACAGGCACCTGGAAAAGGTCTTGAGTGGA
1951  TTGGAGAAATTCATCCAGATAGCAGTACGATTAACTATGCGCCGTCTCTA
2001  AAGGATAGATTTACAATATCGCGAGACAACGCCAAGAACACATTGTTCCT
2051  GCAAATGGACAGCCTGAGACCCGAAGACACCGGGGTCTATTTTTGTGCAA
2101  GCCTTTACTTCGGCTTCCCCTGGTTTGCTTATTGGGGCCAAGGGACCCCG
2151  GTCACCGTCTCCTCAGCCTCCACCAAGGGCCCATCGGTCTTCCCCCTGGC
2201  ACCCTCCTCCAAGAGCACCTCTGGGGGCACAGCGGCCCTGGGCTGCCTGG
2251  TCAAGGACTACTTCCCCGAACCGGTGACGGTGTCGTGGAACTCAGGCGCC
2301  CTGACCAGCGGCGTGCACACCTTCCCGGCTGTCCTACAGTCCTCAGGACT
2351  CTACTCCCTCAGCAGCGTGGTGACCGTGCCCTCCAGCAGCTTGGGCACCC
2401  AGACCTACATCTGCAACGTGAATCACAAGCCCAGCAACACCAAGGTGGAC
2451  AAGAGAGTTGAGCCCAAATCTTGTGACAAAACTCACACATGCCCACCGTG
2501  CCCAGCACCTGAACTCCTGGGGGGACCGTCAGTCTTCCTCTTCCCCCCAA
2551  AACCCAAGGACACCCTCATGATCTCCCGGACCCCTGAGGTCACATGCGTG
2601  GTGGTGGACGTGAGCCACGAAGACCCTGAGGTCAAGTTCAACTGGTACGT
2651  GGACGGCGTGGAGGTGCATAATGCCAAGACAAAGCCGCGGGAGGAGCAGT
2701  ACAACAGCACGTACCGTGTGGTCAGCGTCCTCACCGTCCTGCACCAGGAC
2751  TGGCTGAATGGCAAGGAGTACAAGTGCAAGGTCTCCAACAAAGCCCTCCC
2801  AGCCCCCATCGAGAAAACCATCTCCAAAGCCAAAGGGCAGCCCCGAGAAC
```

Figure 9b

```
2851  CACAGGTGTACACCCTGCCCCCATCCCGGGAGGAGATGACCAAGAACCAG
2901  GTCAGCCTGACCTGCCTGGTCAAAGGCTTCTATCCCAGCGACATCGCCGT
2951  GGAGTGGGAGAGCAATGGGCAGCCGGAGAACAACTACAAGACCACGCCTC
3001  CCGTGCTGGACTCCGACGGCTCCTTCTTCCTCTATAGCAAGCTCACCGTG
3051  GACAAGAGCAGGTGGCAGCAGGGGAACGTCTTCTCATGCTCCGTGATGCA
3101  CGAGGCTCTGCACAACCACTACACGCAGAAGAGCCTCTCCCTGTCTCCCG
3151  GGAAATGAAAGCCGAATTCGCCCCTCTCCCTCCCCCCCCCCTAACGTTAC
3201  TGGCCGAAGCCGCTTGGAATAAGGCCGGTGTGCGTTTGTCTATATGTTAT
3251  TTTCCACCATATTGCCGTCTTTTGGCAATGTGAGGGCCCGGAAACCTGGC
3301  CCTGTCTTCTTGACGAGCATTCCTAGGGGTCTTTCCCCTCTCGCCAAAGG
3351  AATGCAAGGTCTGTTGAATGTCGTGAAGGAAGCAGTTCCTCTGGAAGCTT
3401  CTTGAAGACAAACAACGTCTGTAGCGACCCTTTGCAGGCAGCGGAACCCC
3451  CCACCTGGCGACAGGTGCCTCTGCGGCCAAAAGCCACGTGTATAAGATAC
3501  ACCTGCAAAGGCGGCACAACCCCAGTGCCACGTTGTGAGTTGGATAGTTG
3551  TGGAAAGAGTCAAATGGCTCTCCTCAAGCGTATTCAACAAGGGGCTGAAG
3601  GATGCCCAGAAGGTACCCCATTGTATGGGATCTGATCTGGGGCCTCGGTG
3651  CACATGCTTTACATGTGTTTAGTCGAGGTTAAAAAAACGTCTAGGCCCCC
3701  CGAACCACGGGGACGTGGTTTTCCTTTGAAAAACACGATGATAATATGGC
3751  CTCCTTTGTCTCTCTGCTCCTGGTAGGCATCCTATTCCATGCCACCCAGG
3801  CCGACATCCAGCTGACCCAGAGCCCAAGCAGCCTGAGCGCCAGCGTGGGT
3851  GACAGAGTGACCATCACCTGTAAGGCCAGTCAGGATGTGGGTACTTCTGT
3901  AGCCTGGTACCAGCAGAAGCCAGGTAAGGCTCCAAAGCTGCTGATCTACT
3951  GGACATCCACCCGGCACACTGGTGTGCCAAGCAGATTCAGCGGTAGCGGT
4001  AGCGGTACCGACTTCACCTTCACCATCAGCAGCCTCCAGCCAGAGGACAT
4051  CGCCACCTACTACTGCCAGCAATATAGCCTCTATCGGTCGTTCGGCCAAG
4101  GGACCAAGGTGGAAATCAAACGAACTGTGGCTGCACCATCTGTCTTCATC
4151  TTCCCGCCATCTGATGAGCAGTTGAAATCTGGAACTGCCTCTGTTGTGTG
4201  CCTGCTGAATAACTTCTATCCCAGAGAGGCCAAAGTACAGTGGAAGGTGG
4251  ATAACGCCCTCCAATCGGGTAACTCCCAGGAGAGTGTCACAGAGCAGGAC
4301  AGCAAGGACAGCACCTACAGCCTCAGCAGCACCCTGACGCTGAGCAAAGC
4351  AGACTACGAGAAACACAAAGTCTACGCCTGCGAAGTCACCCATCAGGGCC
4401  TGAGCTCGCCCGTCACAAAGAGCTTCAACAGGGGAGAGTGTTAGAGATCC
4451  CCCGGGCTGCAGGAATTCGATATCAAGCTTATCGATAATCAACCTCTGGA
4501  TTACAAAATTTGTGAAAGATTGACTGGTATTCTTAACTATGTTGCTCCTT
4551  TTACGCTATGTGGATACGCTGCTTTAATGCCTTTGTATCATGCTATTGCT
4601  TCCCGTATGGCTTTCATTTTCTCCTCCTTGTATAAATCCTGGTTGCTGTC
4651  TCTTTATGAGGAGTTGTGGCCCGTTGTCAGGCAACGTGGCGTGGTGTGCA
4701  CTGTGTTTGCTGACGCAACCCCCACTGGTTGGGGCATTGCCACCACCTGT
4751  CAGCTCCTTTCCGGGACTTTCGCTTTCCCCCTCCCTATTGCCACGGCGGA
4801  ACTCATCGCCGCCTGCCTTGCCCGCTGCTGGACAGGGGCTCGGCTGTTGG
4851  GCACTGACAATTCCGTGGTGTTGTCGGGGAAATCATCGTCCTTTCCTTGG
4901  CTGCTCGCCTGTGTTGCCACCTGGATTCTGCGCGGGACGTCCTTCTGCTA
4951  CGTCCCTTCGGCCCTCAATCCAGCGGACCTTCCTTCCCGCGGCCTGCTGC
5001  CGGCCTCTGCGGCCTCTTCCGCGTCTTCGCCTTCGCCCTCAGACGAGTCGG
5051  ATCTCCCTTTGGGCCGCCTCCCCGCCTGATCGATACCGTCAACATCGATA
5101  AAATAAAAGATTTTATTTAGTCTCCAGAAAAAGGGGGGAATGAAAGACCC
5151  CACCTGTAGGTTTGGCAAGCTAGCTTAAGTAACGCCATTTTGCAAGGCAT
5201  GGAAAATACATAACTGAGAATAGAGAAGTTCAGATCAAGGTCAGGAACA
5251  GATGGAACAGCTGAATATGGGCCAAACAGGATATCTGTGGTAAGCAGTTC
5301  CTGCCCCGGCTCAGGGCCAAGAACAGATGGAACAGCTGAATATGGGCCAA
5351  ACAGGATATCTGTGGTAAGCAGTTCCTGCCCCGGCTCAGGGCCAAGAACA
5401  GATGGTCCCCAGATGCGGTCCAGCCCTCAGCAGTTTCTAGAGAACCATCA
5451  GATGTTTCCAGGGTGCCCCAAGGACCTGAAATGACCCTGTGCCTTATTTG
5501  AACTAACCAATCAGTTCGCTTCTCGCTTCTGTTCGCGCGCTTCTGCTCCC
5551  CGAGCTCAATAAAAGAGCCCACAACCCCTCACTCGGGGCGCCAGTCCTCC
5601  GATTGACTGAGTCGCCCGGGTACCCGTGTATCCAATAAACCCTCTTGCAG
5651  TTGCATCCGACTTGTGGTCTCGCTGTTCCTTGGGAGGGTCTCCTCTGAGT
5701  GATTGACTACCCGTCAGCGGGGGTCTTTCATT
```

1 - 1457      Mouse mammary tumor virus LTR
1475 - 1726   Double mutated PPE sequence

Figure 9c

| | |
|---|---|
| 1752 - 1754 | MN14 heavy chain signal peptide start codon |
| 3156 - 3158 | MN14 heavy chain stop codon |
| 3170 - 3745 | EMCV IRES |
| 3746 - 3748 | Bovine alpha-lactalbumin signal peptide start codon |
| 3803 - 3805 | First codon of mature MN14 light chain gene |
| 4442 - 4444 | MN14 antibody light chain gene stop codon |
| 4487 - 5078 | WPRE sequence |
| 5133 - 5372 | MoMuLV 3' LTR |

Figure 10a
SEQ ID NO:7
Alpha-Lactalbumin MN14 Vector

```
   1  AAAGACCCCACCCGTAGGTGGCAAGCTAGCTTAAGTAACGCCACTTTGCA
  51  AGGCATGGAAAAATACATAACTGAGAATAGAAAAGTTCAGATCAAGGTCA
 101  GGAACAAAGAAACAGCTGAATACCAAACAGGATATCTGTGGTAAGCGGTT
 151  CCTGCCCCGGCTCAGGGCCAAGAACAGATGAGACAGCTGAGTGATGGGCC
 201  AAACAGGATATCTGTGGTAAGCAGTTCCTGCCCCGGCTCGGGGCCAAGAA
 251  CAGATGGTCCCCAGATGCGGTCCAGCCCTCAGCAGTTTCTAGTGAATCAT
 301  CAGATGTTTCCAGGGTGCCCCAAGGACCTGAAAATGACCCTGTACCTTAT
 351  TTGAACTAACCAATCAGTTCGCTTCTCGCTTCTGTTCGCGCGCTTCCGCT
 401  CTCCGAGCTCAATAAAAGAGCCCACAACCCCTCACTCGGCGCGCCAGTCT
 451  TCCGATAGACTGCGTCGCCCGGGTACCCGTATTCCCAATAAAGCCTCTTG
 501  CTGTTTGCATCCGAATCGTGGTCTCGCTGTTCCTTGGGAGGGTCTCCTCT
 551  GAGTGATTGACTACCCACGACGGGGGTCTTTCATTTGGGGGCTCGTCCGG
 601  GATTTGGAGACCCCTGCCCAGGGACCACCGACCCACCACCGGGAGGTAAG
 651  CTGGCCAGCAACTTATCTGTGTCTGTCCGATTGTCTAGTGTCTATGTTTG
 701  ATGTTATGCGCCTGCGTCTGTACTAGTTAGCTAACTAGCTCTGTATCTGG
 751  CGGACCCGTGGTGGAACTGACGAGTTCTGAACACCCGGCCGCAACCCTGG
 801  GAGACGTCCCAGGGACTTTGGGGGCCGTTTTGTGGCCCGACCTGAGGAA
 851  GGGAGTCGATGTGGAATCCGACCCCGTCAGGATATGTGGTTCTGGTAGGA
 901  GACGAGAACCTAAAACAGTTCCCGCCTCCGTCTGAATTTTTGCTTTCGGT
 951  TTGGAACCGAAGCCGCGCGTCTTGTCTGCTGCAGCGCTGCAGCATCGTTC
1001  TGTGTTGTCTCTGTCTGACTGTGTTTCTGTATTTGTCTGAAAATTAGGGC
1051  CAGACTGTTACCACTCCCTTAAGTTTGACCTTAGGTCACTGGAAAGATGT
1101  CGAGCGGATCGCTCACAACCAGTCGGTAGATGTCAAGAAGAGACGTTGGG
1151  TTACCTTCTGCTCTGCAGAATGGCCAACCTTTAACGTCGGATGGCCGCGA
1201  GACGGCACCTTTAACCGAGACCTCATCACCCAGGTTAAGATCAAGGTCTT
1251  TTCACCTGGCCCGCATGGACACCCAGACCAGGTCCCCTACATCGTGACCT
1301  GGGAAGCCTTGGCTTTTGACCCCCCTCCCTGGGTCAAGCCCTTTGTACAC
1351  CCTAAGCCTCCGCCTCCTCTTCCTCCATCCGCCCCGTCTCTCCCCCTTGA
1401  ACCTCCTCGTTCGACCCCGCCTCGATCCTCCCTTTATCCAGCCCTCACTC
1451  CTTCTCTAGGCGCCGGAATTCCGATCTGATCAAGAGACAGGATGAGGATC
1501  GTTTCGCATGATTGAACAAGATGGATTGCACGCAGGTTCTCCGGCCGCTT
1551  GGGTGGAGAGGCTATTCGGCTATGACTGGGCACAACAGACAATCGGCTGC
1601  TCTGATGCCGCCGTGTTCCGGCTGTCAGCGCAGGGGCGCCCGGTTCTTTT
1651  TGTCAAGACCGACCTGTCCGGTGCCCTGAATGAACTGCAGGACGAGGCAG
1701  CGCGGCTATCGTGGCTGGCCACGACGGGCGTTCCTTGCGCAGCTGTGCTC
1751  GACGTTGTCACTGAAGCGGGAAGGGACTGGCTGCTATTGGGCGAAGTGCC
1801  GGGGCAGGATCTCCTGTCATCTCACCTTGCTCCTGCCGAGAAAGTATCCA
1851  TCATGGCTGATGCAATGCGGCGGCTGCATACGCTTGATCCGGCTACCTGC
1901  CCATTCGACCACCAAGCGAAACATCGCATCGAGCGAGCACGTACTCGGAT
1951  GGAAGCCGGTCTTGTCGATCAGGATGATCTGGACGAAGAGCATCAGGGGC
2001  TCGCGCCAGCCGAACTGTTCGCCAGGCTCAAGGCGCGCATGCCCGACGGC
2051  GAGGATCTCGTCGTGACCCATGGCGATGCCTGCTTGCCGAATATCATGGT
2101  GGAAAATGGCCGCTTTTCTGGATTCATCGACTGTGGCCGGCTGGGTGTGG
2151  CGGACCGCTATCAGGACATAGCGTTGGCTACCCGTGATATTGCTGAAGAG
2201  CTTGGCGGCGAATGGGCTGACCGCTTCCTCGTGCTTTACGGTATCGCCGC
2251  TCCCGATTCGCAGCGCATCGCCTTCTATCGCCTTCTTGACGAGTTCTTCT
2301  GAGCGGGACTCTGGGGTTCGAAATGACCGACCAAGCGACGCCCAACCTGC
2351  CATCACGAGATTTCGATTCCACCGCCGCCTTCTATGAAAGGTTGGGCTTC
2401  GGAATCGTTTTCCGGGACGCCGGCTGGATGATCCTCCAGCGCGGGATCT
2451  CATGCTGGAGTTCTTCGCCCACCCCGGGCTCGATCCCCTCGCGAGTTGGT
2501  TCAGCTGCTGCCTGAGGCTGGACGACCTCGCGGAGTTCTACCGGCAGTGC
2551  AAATCCGTCGGCATCCAGGAAACCAGCAGCGGCTATCCGCGCATCCATGC
2601  CCCCGAACTGCAGGAGTGGGGAGGCACGATGGCCGCTTTGGTCGAGGCGG
2651  ATCCTAGAACTAGCGAAAATGCAAGAGCAAAGACGAAAACATGCCACACA
2701  TGAGGAATACCGATTCTCTCATTAACATATTCAGGCCAGTTATCTGGGCT
2751  TAAAAGCAGAAGTCCAACCCAGATAACGATCATATACATGGTTCTCTCCA
2801  GAGGTTCATTACTGAACACTCGTCCGAGAATAACGAGTGGATCAGTCCTG
```

Figure 10b

```
2851 GGTGGTCATTGAAAGGACTGATGCTGAAGTTGAAGCTCCAATACTTTGGC
2901 CACCTGATGCGAAGAACTGACTCATGTGATAAGACCCTGATACTGGGAAA
2951 GATTGAAGGCAGGAGGAGAAGGGATGACAGAGGATGGAAGAGTTGGATGG
3001 AATCACCAACTCGATGGACATGAGTTTGAGCAAGCTTCCAGGAGTTGGTA
3051 ATGGGCAGGGAAGCCTGGCGTGCTGCAGTCCATGGGGTTGCAAAGAGTTG
3101 GACACTACTGAGTGACTGAACTGAACTGATAGTGTAATCCATGGTACAGA
3151 ATATAGGATAAAAAGAGGAAGAGTTTGCCCTGATTCTGAAGAGTTGTAG
3201 GATATAAAAGTTTAGAATACCTTTAGTTTGGAAGTCTTAAATTATTTACT
3251 TAGGATGGGTACCCACTGCAATATAAGAAATCAGGCTTTAGAGACTGATG
3301 TAGAGAGAATGAGCCCTGGCATACCAGAAGCTAACAGCTATTGGTTATAG
3351 CTGTTATAACCAATATATAACCAATATATTGGTTATATAGCATGAAGCTT
3401 GATGCCAGCAATTTGAAGGAACCATTTAGAACTAGTATCCTAAACTCTAC
3451 ATGTTCCAGGACACTGATCTTAAAGCTCAGGTTCAGAATCTTGTTTTATA
3501 GGCTCTAGGTGTATATTGTGGGGCTTCCCTGGTGGCTCAGATGGTAAAGT
3551 GTCTGCCTGCAATGTGGGTGATCTGGGTTCGATCCCTGGCTTGGGAAGAT
3601 CCCCTGGAGAAGGAAATGGCAACCCACTCTAGTACTCTTACCTGGAAAAT
3651 TCCATGGACAGAGGAGCCTTGTAAGCTACAGTCCATGGGATTGCAAAGAG
3701 TTGAACACAACTGAGCAACTAAGCACAGCACAGTACAGTATACACCTGTG
3751 AGGTGAAGTGAAGTGAAGGTTCAATGCAGGGTCTCCTGCATTGCAGAAAG
3801 ATTCTTTACCATCTGAGCCACCAGGGAAGCCCAAGAATACTGGAGTGGGT
3851 AGCCTATTCCTTCTCCAGGGGATCTTCCCATCCCAGGAATTGAACTGGAG
3901 TCTCCTGCATTTCAGGTGGATTCTTCACCAGCTGAACTACCAGGTGGATA
3951 CTACTCCAATATTAAAGTGCTTAAAGTCCAGTTTTCCCACCTTTCCCAAA
4001 AAGGTTGGGTCACTCTTTTTTAACCTTCTGTGGCCTACTCTGAGGCTGTC
4051 TACAAGCTTATATATTTATGAACACATTTATTGCAAGTTGTTAGTTTTAG
4101 ATTTACAATGTGGTATCTGGCTATTTAGTGGTATTGGTGGTTGGGGATGG
4151 GGAGGCTGATAGCATCTCAGAGGGCAGCTAGATACTGTCATACACACTTT
4201 TCAAGTTCTCCATTTTTGTGAAATAGAAAGTCTCTGGATCTAAGTTATAT
4251 GTGATTCTCAGTCTCTGTGGTCATATTCTATTCTACTCCTGACCACTCAA
4301 CAAGGAACCAAGATATCAAGGGACACTTGTTTTGTTTCATGCCTGGGTTG
4351 AGTGGGCCATGACATATGTTCTGGGCCTTGTTACATGGCTGGATTGGTTG
4401 GACAAGTGCCAGCTCTGATCCTGGGACTGTGGCATGTGATGACATACACC
4451 CCCTCTCCACATTCTGCATGTCTCTAGGGGGAAGGGGGAAGCTCGGTAT
4501 AGAACCTTTATTGTATTTTCTGATTGCCTCACTTCTTATATTGCCCCCAT
4551 GCCCTTCTTTGTTCCTCAAGTAACCAGAGACAGTGCTTCCCAGAACCAAC
4601 CCTACAAGAAACAAAGGGCTAAACAAAGCCAAATGGGAAGCAGGATCATG
4651 GTTTGAACTCTTTCTGGCCAGAGAACAATACCTGCTATGGACTAGATACT
4701 GGGAGAGGGAAAGGAAAAGTAGGGTGAATTATGGAAGGAAGCTGGCAGGC
4751 TCAGCGTTTCTGTCTTGGCATGACCAGTCTCTCTTCATTCTCTTCCTAGA
4801 TGTAGGGCTTGGTACCAGAGCCCCTGAGGCTTTCTGCATGAATATAAATA
4851 TATGAAACTGAGTGATGCTTCCATTTCAGGTTCTTGGGGGCGCCGAATTC
4901 GAGCTCGGTACCCGGGGATCTCGACGGATCCGATTACTTACTGGCAGGTG
4951 CTGGGGGCTTCCGAGACAATCGCGAACATCTACACCACACAACACCGCCT
5001 CGACCAGGGTGAGATATCGGCCGGGACGCGGCGGTGGTAATTACAAGCG
5051 AGATCCGATTACTTACTGGCAGGTGCTGGGGGCTTCCGAGACAATCGCGA
5101 ACATCTACACCACACAACACCGCCTCGACCAGGGTGAGATATCGGCCGGG
5151 GACGCGGCGGTGGTAATTACAAGCGAGATCCCCGGGAATTCAGGACCTCA
5201 CCATGGGATGGAGCTGTATCATCCTCTTCTTGGTAGCAACAGCTACAGGT
5251 GTCCACTCCGAGGTCCAACTGGTGGAGAGCGGTGGAGGTGTTGTGCAACC
5301 TGGCCGGTCCCTGCGCCTGTCCTGCTCCGCATCTGGCTTCGATTTCACCA
5351 CATATTGGATGAGTTGGGTGAGACAGGCACCTGGAAAAGGTCTTGAGTGG
5401 ATTGGAGAAATTCATCCAGATAGCAGTACGATTAACTATGCGCCGTCTCT
5451 AAAGGATAGATTTACAATATCGCGAGACAACGCCAAGAACACATTGTTCC
5501 TGCAAATGGACAGCCTGAGACCCGAAGACACCGGGGTCTATTTTTGTGCA
5551 AGCCTTTACTTCGGCTTCCCCTGGTTTGCTTATTGGGGCCAAGGGACCCC
5601 GGTCACCGTCTCCTCAGCCTCCACCAAGGGCCCATCGGTCTTCCCCCTGG
5651 CACCCTCCTCCAAGAGCACCTCTGGGGGCACAGCGGCCCTGGGCTGCCTG
5701 GTCAAGGACTACTTCCCCGAACCGGTGACGGTGTCGTGGAACTCAGGCGC
5751 CCTGACCAGCGGCGTGCACACCTTCCCGGCTGTCCTACAGTCCTCAGGAC
5801 TCTACTCCCTCAGCAGCGTGGTGACCGTGCCCTCCAGCAGCTTGGGCACC
5851 CAGACCTACATCTGCAACGTGAATCACAAGCCCAGCAACACCAAGGTGGA
5901 CAAGAGAGTTGAGCCCAAATCTTGTGACAAAACTCACACATGCCCACCGT
```

Figure 10c

```
5951 GCCCAGCACCTGAACTCCTGGGGGGACCGTCAGTCTTCCTCTTCCCCCCA
6001 AAACCCAAGGACACCCTCATGATCTCCCGGACCCCTGAGGTCACATGCGT
6051 GGTGGTGGACGTGAGCCACGAAGACCCTGAGGTCAAGTTCAACTGGTACG
6101 TGGACGGCGTGGAGGTGCATAATGCCAAGACAAAGCCGCGGGAGGAGCAG
6151 TACAACAGCACGTACCGTGTGGTCAGCGTCCTCACCGTCCTGCACCAGGA
6201 CTGGCTGAATGGCAAGGAGTACAAGTGCAAGGTCTCCAACAAAGCCCTCC
6251 CAGCCCCCATCGAGAAAACCATCTCCAAAGCCAAAGGGCAGCCCCGAGAA
6301 CCACAGGTGTACACCCTGCCCCCATCCCGGGAGGAGATGACCAAGAACCA
6351 GGTCAGCCTGACCTGCCTGGTCAAAGGCTTCTATCCCAGCGACATCGCCG
6401 TGGAGTGGGAGAGCAATGGGCAGCCGGAGAACAACTACAAGACCACGCCT
6451 CCCGTGCTGGACTCCGACGGCTCCTTCTTCCTCTATAGCAAGCTCACCGT
6501 GGACAAGAGCAGGTGGCAGCAGGGGAACGTCTTCTCATGCTCCGTGATGC
6551 ACGAGGCTCTGCACAACCACTACACGCAGAAGAGCCTCTCCCTGTCTCCC
6601 GGGAAATGAAAGCCGAATTCGCCCCTCTCCCTCCCCCCCCCCTAACGTTA
6651 CTGGCCGAAGCCGCTTGGAATAAGGCCGGTGTGCGTTTGTCTATATGTTA
6701 TTTTCCACCATATTGCCGTCTTTTGGCAATGTGAGGGCCCGGAAACCTGG
6751 CCCTGTCTTCTTGACGAGCATTCCTAGGGGTCTTTCCCCTCTCGCCAAAG
6801 GAATGCAAGGTCTGTTGAATGTCGTGAAGGAAGCAGTTCCTCTGGAAGCT
6851 TCTTGAAGACAAACAACGTCTGTAGCGACCCTTTGCAGGCAGCGGAACCC
6901 CCCACCTGGCGACAGGTGCCTCTGCGGCCAAAAGCCACGTGTATAAGATA
6951 CACCTGCAAAGGCGGCACAACCCCAGTGCCACGTTGTGAGTTGGATAGTT
7001 GTGGAAAGAGTCAAATGGCTCTCCTCAAGCGTATTCAACAAGGGGCTGAA
7051 GGATGCCCAGAAGGTACCCCATTGTATGGGATCTGATCTGGGGCCTCGGT
7101 GCACATGCTTTACATGTGTTTAGTCGAGGTTAAAAAAACGTCTAGGCCCC
7151 CCGAACCACGGGGACGTGGTTTTCCTTTGAAAAACACGATGATAATATGG
7201 CCTCCTTTGTCTCTCTGCTCCTGGTAGGCATCCTATTCCATGCCACCCAG
7251 GCCGACATCCAGCTGACCCAGAGCCCAAGCAGCCTGAGCGCCAGCGTGGG
7301 TGACAGAGTGACCATCACCTGTAAGGCCAGTCAGGATGTGGGTACTTCTG
7351 TAGCCTGGTACCAGCAGAAGCCAGGTAAGGCTCCAAAGCTGCTGATCTAC
7401 TGGACATCCACCCGGCACACTGGTGTGCCAAGCAGATTCAGCGGTAGCGG
7451 TAGCGGTACCGACTTCACCTTCACCATCAGCAGCCTCCAGCCAGAGGACA
7501 TCGCCACCTACTACTGCCAGCAATATAGCCTCTATCGGTCGTTCGGCCAA
7551 GGGACCAAGGTGGAAATCAAACGAACTGTGGCTGCACCATCTGTCTTCAT
7601 CTTCCCGCCATCTGATGAGCAGTTGAAATCTGGAACTGCCTCTGTTGTGT
7651 GCCTGCTGAATAACTTCTATCCCAGAGAGGCCAAAGTACAGTGGAAGGTG
7701 GATAACGCCCTCCAATCGGGTAACTCCCAGGAGAGTGTCACAGAGCAGGA
7751 CAGCAAGGACAGCACCTACAGCCTCAGCAGCACCCTGACGCTGAGCAAAG
7801 CAGACTACGAGAAACACAAAGTCTACGCCTGCGAAGTCACCCATCAGGGC
7851 CTGAGCTCGCCCGTCACAAAGAGCTTCAACAGGGGAGAGTGTTAGAGATC
7901 CCCCGGGCTGCAGGAATTCGATATCAAGCTTATCGATAATCAACCTCTGG
7951 ATTACAAAATTTGTGAAAGATTGACTGGTATTCTTAACTATGTTGCTCCT
8001 TTTACGCTATGTGGATACGCTGCTTTAATGCCTTTGTATCATGCTATTGC
8051 TTCCCGTATGGCTTTCATTTTCTCCTCCTTGTATAAATCCTGGTTGCTGT
8101 CTCTTTATGAGGAGTTGTGGCCCGTTGTCAGGCAACGTGGCGTGGTGTGC
8151 ACTGTGTTTGCTGACGCAACCCCCACTGGTTGGGGCATTGCCACCACCTG
8201 TCAGCTCCTTTCCGGGACTTTCGCTTTCCCCCTCCCTATTGCCACGGCGG
8251 AACTCATCGCCGCCTGCCTTGCCCGCTGCTGGACAGGGGCTCGGCTGTTG
8301 GGCACTGACAATTCCGTGGTGTTGTCGGGGAAATCATCGTCCTTTCCTTG
8351 GCTGCTCGCCTGTGTTGCCACCTGGATTCTGCGCGGGACGTCCTTCTGCT
8401 ACGTCCCTTCGGCCCTCAATCCAGCGGACCTTCCTTCCCGCGGCCTGCTG
8451 CCGGCTCTGCGGCCTCTTCCGCGTCTTCGCCTTCGCCCTCAGACGAGTCG
8501 GATCTCCCTTTGGGCCGCCTCCCCGCCTGATCGATACCGTCAACATCGAT
8551 AAAATAAAAGATTTTATTTAGTCTCCAGAAAAAGGGGGGAATGAAAGACC
8601 CCACCTGTAGGTTTGGCAAGCTAGCTTAAGTAACGCCATTTTGCAAGGCA
8651 TGGAAAAATACATAACTGAGAATAGAGAAGTTCAGATCAAGGTCAGGAAC
8701 AGATGGAACAGCTGAATATGGGCCAAACAGGATATCTGTGGTAAGCAGTT
8751 CCTGCCCCGGCTCAGGGCCAAGAACAGATGGAACAGCTGAATATGGGCCA
8801 AACAGGATATCTGTGGTAAGCAGTTCCTGCCCCGGCTCAGGGCCAAGAAC
8851 AGATGGTCCCCAGATGCGGTCCAGCCCTCAGCAGTTTCTAGAGAACCATC
8901 AGATGTTTCCAGGGTGCCCCAAGGACCTGAAATGACCCTGTGCCTTATTT
8951 GAACTAACCAATCAGTTCGCTTCTCGCTTCTGTTCGCGCGCTTCTGCTCC
9001 CCGAGCTCAATAAAAGAGCCCACAACCCCTCACTCGGGGCGCCAGTCCTC
```

Figure 10d
```
9051  CGATTGACTGAGTCGCCCGGGTACCCGTGTATCCAATAAACCCTCTTGCA
9101  GTTGCATCCGACTTGTGGTCTCGCTGTTCCTTGGGAGGGTCTCCTCTGAG
9151  TGATTGACTACCCGTCAGCGGGGGTCTTTCATT
```

| | |
|---|---|
| 1 - 658 | MoMuSV 5' LTR |
| 659 - 1468 | Extended packaging region |
| 1512 - 2306 | Neomycin resistance gene |
| 2661 - 4896 | Bovine/human alpha-lactalbumin 5' flanking region |
| 5084 - 5327 | Double mutated PPE sequence |
| 6207 - 6209 | MN14 antibody heavy chain gene signal peptide start codon |
| 6611-6613 | MN14 antibody heavy chain stop codon |
| 6625 - 7200 | EMCV IRES |
| 7201 - 7203 | Bovine alpha-lactalbumin signal peptide start codon |
| 7258 - 7260 | First codon of mature MN14 antibody light chain gene |
| 7897 - 7899 | MN14 antibody light gene stop codon |
| 7938 - 8529 | WPRE sequence |
| 8600 - 9138 | Moloney murine leukemia virus 3' LTR |

Figure 11a
SEQ ID NO:8
Alpha-Lactalbumin Bot Vector

```
   1  GATCAGTCCTGGGTGGTCATTGAAAGGACTGATGCTGAAGTTGAAGCTCC
  51  AATACTTTGGCCACCTGATGCGAAGAACTGACTCATGTGATAAGACCCTG
 101  ATACTGGGAAAGATTGAAGGCAGGAGGAGAAGGGATGACAGAGGATGGAA
 151  GAGTTGGATGGAATCACCAACTCGATGGACATGAGTTTGAGCAAGCTTCC
 201  AGGAGTTGGTAATGGGCAGGGAAGCCTGGCGTGCTGCAGTCCATGGGGTT
 251  GCAAAGAGTTGGACACTACTGAGTGACTGAACTGAACTGATAGTGTAATC
 301  CATGGTACAGAATATAGGATAAAAAGAGGAAGAGTTTGCCCTGATTCTG
 351  AAGAGTTGTAGGATATAAAAGTTTAGAATACCTTTAGTTTGGAAGTCTTA
 401  AATTATTTACTTAGGATGGGTACCCACTGCAATATAAGAAATCAGGCTTT
 451  AGAGACTGATGTAGAGAGAATGAGCCCTGGCATACCAGAAGCTAACAGCT
 501  ATTGGTTATAGCTGTTATAACCAATATATAACCAATATATTGGTTATATA
 551  GCATGAAGCTTGATGCCAGCAATTTGAAGGAACCATTTAGAACTAGTATC
 601  CTAAACTCTACATGTTCCAGGACACTGATCTTAAAGCTCAGGTTCAGAAT
 651  CTTGTTTTATAGGCTCTAGGTGTATATTGTGGGGCTTCCCTGGTGGCTCA
 701  GATGGTAAAGTGTCTGCCTGCAATGTGGGTGATCTGGGTTCGATCCCTGG
 751  CTTGGGAAGATCCCCTGGAGAAGGAAATGGCAACCCACTCTAGTACTCTT
 801  ACCTGGAAAATTCCATGGACAGAGGAGCCTTGTAAGCTACAGTCCATGGG
 851  ATTGCAAAGAGTTGAACACAACTGAGCAACTAAGCACAGCACAGTACAGT
 901  ATACACCTGTGAGGTGAAGTGAAGTGAAGGTTCAATGCAGGGTCTCCTGC
 951  ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACTTTTCAAGTTCTCCATTTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGTTCTGGGCCTTGTTACATGGC
1551  TGGATTGGTTGGACAAGTGCCAGCTCTGATCCTGGGACTGTGGCATGTGA
1601  TGACATACACCCCCTCTCCACATTCTGCATGTCTCTAGGGGGGAAGGGGG
1651  AAGCTCGGTATAGAACCTTTATTGTATTTTCTGATTGCCTCACTTCTTAT
1701  ATTGCCCCCATGCCCTTCTTTGTTCCTCAAGTAACCAGAGACAGTGCTTC
1751  CCAGAACCAACCCTACAAGAAACAAAGGGCTAAACAAAGCCAAATGGGAA
1801  GCAGGATCATGGTTTGAACTCTTTCTGGCCAGAGAACAATACCTGCTATG
1851  GACTAGATACTGGGAGAGGGAAAGGAAAAGTAGGGTGAATTATGGAAGGA
1901  AGCTGGCAGGCTCAGCGTTTCTGTCTTGGCATGACCAGTCTCTCTTCATT
1951  CTCTTCCTAGATGTAGGGCTTGGTACCAGAGCCCCTGAGGCTTTCTGCAT
2001  GAATATAAATATATGAAACTGAGTGATGCTTCCATTTCAGGTTCTTGGGG
2051  GCGCCGAATTCGAGCTCGGTACCCGGGGATCTCGACGGATCCGATTACTT
2101  ACTGGCAGGTGCTGGGGCTTCCGAGACAATCGCGAACATCTACACCACA
2151  CAACACCGCCTCGACCAGGGTGAGATATCGGCCGGGGACGCGGCGGTGGT
2201  AATTACAAGCGAGATCCGATTACTTACTGGCAGGTGCTGGGGCTTCCGA
2251  GACAATCGCGAACATCTACACCACACAACACCGCCTCGACCAGGGTGAGA
2301  TATCGGCCGGGACGCGGCGGTGGTAATTACAAGCGAGATCTCGAGAAGC
2351  TTGTTGGGAATTCAGGCCATCGATCCCGCCGCCACCATGGAATGGAGCTG
2401  GGTCTTTCTCTTCTTCCTGTCAGTAACTACAGGTGTCCACTCCGACATCC
2451  AGATGACCCAGTCTCCAGCCTCCCTATCTGCATCTGTGGGAGAAACTGTC
2501  ACTATCACATGTCGAGCAAGTGGGAATATTCACAATTATTTAGCATGGTA
2551  TCAGCAGAAACAGGGAAAATCTCCTCAGCTCCTGGTCTATAATGCAAAAA
2601  CCTTAGCAGATGGTGTGCCATCAAGGTTCAGTGGCAGTGGATCAGGAACA
2651  CAATATTCTCTCAAGATCAACAGCCTGCAGCCTGAAGATTTTGGGAGTTA
2701  TTACTGTCAACATTTTTGGAGTACTCCGTGGACGTTCGGTGGAGGCACCA
2751  AGCTGGAAATCAAACGGGCTGATGCTGCACCAACTGTATCCATCTTCCCA
2801  CCATCCAGTGAGCAGTTAACATCTGGAGGTGCCTCAGTCGTGTGCTTCTT
```

Figure 11b

```
2851  GAACAACTTCTACCCCAAAGACATCAATGTCAAGTGGAAGATTGATGGCA
2901  GTGAACGACAAAATGGCGTCCTGAACAGTTGGACTGATCAGGACAGCAAA
2951  GACAGCACCTACAGCATGAGCAGCACCCTCACATTGACCAAGGACGAGTA
3001  TGAACGACATAACAGCTATACCTGTGAGGCCACTCACAAGACATCAACTT
3051  CACCCATTGTCAAGAGCTTCAACAGGAATGAGTGTTGAAAGCATCGATTT
3101  CCCCTGAATTCGCCCCTCTCCCTCCCCCCCCCTAACGTTACTGGCCGAA
3151  GCCGCTTGGAATAAGGCCGGTGTGCGTTTGTCTATATGTTATTTTCCACC
3201  ATATTGCCGTCTTTTGGCAATGTGAGGGCCCGGAAACCTGGCCCTGTCTT
3251  CTTGACGAGCATTCCTAGGGGTCTTTCCCCTCTCGCCAAAGGAATGCAAG
3301  GTCTGTTGAATGTCGTGAAGGAAGCAGTTCCTCTGGAAGCTTCTTGAAGA
3351  CAAACAACGTCTGTAGCGACCCTTTGCAGGCAGCGGAACCCCCCACCTGG
3401  CGACAGGTGCCTCTGCGGCCAAAAGCCACGTGTATAAGATACACCTGCAA
3451  AGGCGGCACAACCCCAGTGCCACGTTGTGAGTTGGATAGTTGTGGAAAGA
3501  GTCAAATGGCTCTCCTCAAGCGTATTCAACAAGGGGCTGAAGGATGCCCA
3551  GAAGGTACCCCATTGTATGGGATCTGATCTGGGGCCTCGGTGCACATGCT
3601  TTACATGTGTTTAGTCGAGGTTAAAAAAACGTCTAGGCCCCCCGAACCAC
3651  GGGGACGTGGTTTTCCTTTGAAAAACACGATGATAATATGGCCTCCTTTG
3701  TCTCTCTGCTCCTGGTAGGCATCCTATTCCATGCCACCCAGGCCGAGGTT
3751  CAGCTTCAGCAGTCTGGGGCAGAGCTTGTGAAGCCAGGGGCCTCAGTCAA
3801  GTTGTCCTGCACAGCTTCTGGCTTCAACATTAAAGACACCTTTATGCACT
3851  GGGTGAAGCAGAGGCCTGAACAGGGCCTGGAGTGGATTGGAAGGATTGAT
3901  CCTGCGAATGGGAATACTGAATATGACCCGAAGTTCCAGGGCAAGGCCAC
3951  TATAACAGCAGACACATCCTCCAACACAGTCAACCTGCAGCTCAGCAGCC
4001  TGACATCTGAGGACACTGCCGTCTATTACTGTGCTAGTGGAGGGGAACTG
4051  GGGTTTCCTTACTGGGGCCAAGGGACTCTGGTCACTGTCTCTGCAGCCAA
4101  AACGACACCCCCATCTGTCTATCCACTGGCCCCTGGATCTGCTGCCCAAA
4151  CTAACTCCATGGTGACCCTGGGATGCCTGGTCAAGGGCTATTTCCCTGAG
4201  CCAGTGACAGTGACCTGGAACTCTGGATCCCTGTCCAGCGGTGTGCACAC
4251  CTTCCCAGCTGTCCTGCAGTTTGACCTCTACACTCTGAGCAGCTCAGTGA
4301  CTGTCCCCTCCAGCACCTGGCCCAGCGAGACCGTCACCTGCAACGTTGCC
4351  CACCCGGCCAGCAGCACCAAGGTGGACAAGAAAATTGTGCCCAGGGATTG
4401  TACTAGTGGAGGTGGAGGTAGCCACCATCACCATCACCATTAATCTAGAG
4451  TTAAGCGGCCGTCGAGATCTCGACATCGATAATCAACCTCTGGATTACAA
4501  AATTTGTGAAAGATTGACTGGTATTCTTAACTATGTTGCTCCTTTTACGC
4551  TATGTGGATACGCTGCTTTAATGCCTTTGTATCATGCTATTGCTTCCCGT
4601  ATGGCTTTCATTTTCTCCTCCTTGTATAAATCCTGGTTGCTGTCTCTTTA
4651  TGAGGAGTTGTGGCCCGTTGTCAGGCAACGTGGCGTGGTGTGCACTGTGT
4701  TTGCTGACGCAACCCCCACTGGTTGGGGCATTGCCACCACCTGTCAGCTC
4751  CTTTCCGGGACTTTCGCTTTCCCCCTCCCTATTGCCACGGCGGAACTCAT
4801  CGCCGCCTGCCTTGCCCGCTGCTGGACAGGGCTCGGCTGTTGGGCACTG
4851  ACAATTCCGTGGTGTTGTCGGGGAAATCATCGTCCTTTCCTTGGCTGCTC
4901  GCCTGTGTTGCCACCTGGATTCTGCGCGGGACGTCCTTCTGCTACGTCCC
4951  TTCGGCCCTCAATCCAGCGGACCTTCCTTCCCGCGGCCTGCTGCCGGCTC
5001  TGCGGCCTCTTCCGCGTCTTCGCCTTCGCCCTCAGACGAGTCGGATCTCC
5051  CTTTGGGCCGCCTCCCCGCCTGATCGATAAAATAAAAGATTTTATTTAGT
5101  CTCCAGAAAAGGGGGGAATGAAAGACCCCACCTGTAGGTTTGGCAAGCT
5151  AGCTTAAGTAACGCCATTTTGCAAGGCATGGAAAAATACATAACTGAGAA
5201  TAGAGAAGTTCAGATCAAGGTCAGGAACAGATGGAACAGCTGAATATGGG
5251  CCAAACAGGATATCTGTGGTAAGCAGTTCCTGCCCCGGCTCAGGGCCAAG
5301  AACAGATGGAACAGCTGAATATGGGCCAAACAGGATATCTGTGGTAAGCA
5351  GTTCCTGCCCCGGCTCAGGGCCAAGAACAGATGGTCCCCAGATGCGGTCC
5401  AGCCCTCAGCAGTTTCTAGAGAACCATCAGATGTTTCCAGGGTGCCCCAA
5451  GGACCTGAAATGACCCTGTGCCTTATTTGAACTAACCAATCAGTTCGCTT
5501  CTCGCTTCTGTTCGCGCGCTTCTGCTCCCCGAGCTCAATAAAAGAGCCCA
5551  CAACCCCTCACTCGGGGCGCCAGTCCTCCGATTGACTGAGTCGCCCGGGT
5601  ACCCGTGTATCCAATAAACCCTCTTGCAGTTGCATCCGACTTGTGGTCTC
```

Figure 11c
```
5651  GCTGTTCCTTGGGAGGGTCTCCTCTGAGTGATTGACTACCCGTCAGCGGG
5701  GGTCTTTCATT
```

| | |
|---|---|
| 1 - 2053 | Bovine/human alpha-lactalbumin 5' flanking region |
| 2093 - 2336 | Double mtated PPE sequence |
| 2387 - 2443 | cc49 signal peptide coding region |
| 2444 - 3088 | Bot antibody light chain Fab coding region |
| 3112 - 3686 | EMCV IRES |
| 3687 - 3745 | Bovine alpha-lactalbumin signal peptide coding region |
| 3746 - 4443 | Bot antibody heavy chain Fab coding region |
| 4481 - 5072 | WPRE sequence |
| 5118 - 5711 | Molo Figure 12a
SEQ ID NO:9
LSNRL Vector

```
   1 TTTGAAAGACCCCACCCGTAGGTGGCAAGCTAGCTTAAGTAACGCCACTT
  51 TGCAAGGCATGGAAAAATACATAACTGAGAATAGAAAAGTTCAGATCAAG
 101 GTCAGGAACAAAGAAACAGCTGAATACCAAACAGGATATCTGTGGTAAGC
 151 GGTTCCTGCCCCGGCTCAGGGCCAAGAACAGATGAGACAGCTGAGTGATG
 201 GGCCAAACAGGATATCTGTGGTAAGCAGTTCCTGCCCCGGCTCGGGGCCA
 251 AGAACAGATGGTCCCCAGATGCGGTCCAGCCCTCAGCAGTTTCTAGTGAA
 301 TCATCAGATGTTTCCAGGGTGCCCCAAGGACCTGAAAATGACCCTGTACC
 351 TTATTTGAACTAACCAATCAGTTCGCTTCTCGCTTCTGTTCGCGCGCTTC
 401 CGCTCTCCGAGCTCAATAAAAGAGCCCACAACCCCTCACTCGGCGCGCCA
 451 GTCTTCCGATAGACTGCGTCGCCCGGGTACCCGTATTCCCAATAAAGCCT
 501 CTTGCTGTTTGCATCCGAATCGTGGTCTCGCTGTTCCTTGGGAGGGTCTC
 551 CTCTGAGTGATTGACTACCCACGACGGGGGTCTTTCATTTGGGGGCTCGT
 601 CCGGGATTTGGAGACCCCTGCCCAGGGACCACCGACCCACCACCGGGAGG
 651 TAAGCTGGCCAGCAACTTATCTGTGTCTGTCCGATTGTCTAGTGTCTATG
 701 TTTGATGTTATGCGCCTGCGTCTGTACTAGTTAGCTAACTAGCTCTGTAT
 751 CTGGCGGACCCGTGGTGGAACTGACGAGTTCTGAACACCCGGCCGCAACC
 801 CTGGGAGACGTCCCAGGGACTTTGGGGGCCGTTTTTGTGGCCCGACCTGA
 851 GGAAGGGAGTCGATGTGGAATCCGACCCCGTCAGGATATGTGGTTCTGGT
 901 AGGAGACGAGAACCTAAAACAGTTCCCGCCTCCGTCTGAATTTTTGCTTT
 951 CGGTTTGGAACCGAAGCCGCGCGTCTTGTCTGCTGCAGCCAAGCTTGGGC
1001 TGCAGGTCGAGGACTGGGGACCCTGCACCGAACATGGAGAACACAACATC
1051 AGGATTCCTAGGACCCCTGCTCGTGTTACAGGCGGGGTTTTCTTGTTGA
1101 CAAGAATCCTCACAATACCACAGAGTCTAGACTCGTGGTGGACTTCTCTC
1151 AATTTTCTAGGGGAGCACCCACGTGTCCTGGCCAAAATTCGCAGTCCCC
1201 AACCTCCAATCACTCACCAACCTCTTGTCCTCCAATTTGTCCTGGCTATC
1251 GCTGGATGTGTCTGCGGCGTTTTATCATATTCCTCTTCATCCTGCTGCTA
1301 TGCCTCATCTTCTTGTTGGTTCTTCTGGACTACCAAGGTATGTTGCCCGT
1351 TTGTCCTCTACTTCCAGGAACATCAACTACCAGCACGGGACCATGCAAGA
1401 CCTGCACGATTCCTGCTCAAGGAACCTCTATGTTTCCCTCTTGTTGCTGT
1451 ACAAAACCTTCGGACGGAAACTGCACTTGTATTCCCATCCCATCATCCTG
1501 GGCTTTCGCAAGATTCCTATGGGAGTGGGCCTCAGTCCGTTTCTCCTGGC
1551 TCAGTTTACTAGTGCCATTTGTTCAGTGGTTCGTAGGGCTTTCCCCCACT
1601 GTTTGGCTTTCAGTTATATGGATGATGTGGTATTGGGGGCCAAGTCTGTA
1651 CAACATCTTGAGTCCCTTTTTACCTCTATTACCAATTTTCTTTTGTCTTT
1701 GGGTATACATTTAAACCCTAATAAAACCAAACGTTGGGGCTACTCCCTTA
1751 ACTTCATGGGATATGTAATTGGATGTTGGGGTACTTTACCGCAAGAACAT
1801 ATTGTACTAAAAATCAAGCAATGTTTTCGAAAACTGCCTGTAAATAGACC
1851 TATTGATTGGAAAGTATGTCAGAGACTTGTGGGTCTTTTGGGCTTTGCTG
1901 CCCCTTTTACACAATGTGGCTATCCTGCCTTAATGCCTTTATATGCATGT
1951 ATACAATCTAAGCAGGCTTTCACTTTCTCGCCAACTTACAAGGCCTTTCT
2001 GTGTAAACAATATCTGAACCTTTACCCCGTTGCCCGGCAACGGTCAGGTC
2051 TCTGCCAAGTGTTTGCTGACGCAACCCCCACTGGATGGGCTTGGCTATC
2101 GGCCATAGCCGCATGCGCGGACCTTTGTGGCTCCTCTGCCGATCCATACT
2151 GCGGAACTCCTAGCAGCTTGTTTTGCTCGCAGGCGGTCTGGAGCGAAACT
2201 TATCGGCACCGACAACTCTGTTGTCCTCTCTCGGAAATACACCTCCTTTC
2251 CATGGCTGCTAGGGTGTGCTGCCAACTGGATCCCCTCAGGATATAGTAGT
2301 TTCGCTTTTGCATAGGGAGGGGGAAATGTAGTCTTATGCAATACACTTGT
2351 AGTCTTGCAACATGGTAACGATGAGTTAGCAACATGCCTTACAAGGAGAG
2401 AAAAAGCACCGTGCATGCCGATTGGTGGAAGTAAGGTGGTACGATCGTGC
2451 CTTATTAGGAAGGCAACAGACAGGTCTGACATGGATTGGACGAACCACTG
2501 AATTCCGCATTGCAGAGATAATTGTATTTAAGTGCCTAGCTCGATACAGC
2551 AAACGCCATTTTTGACCATTCACCACATTGGTGTGCACCTTCCAAAGCTT
2601 CACGCTGCCGCAAGCACTCAGGGCGCAAGGGCTGCTAAAGGAAGCGGAAC
2651 ACGTAGAAAGCCAGTCCGCAGAAACGGTGCTGACCCCGGATGAATGTCAG
2701 CTACTGGGCTATCTGGACAAGGGAAAACGCAAGCGCAAAGAGAAAGCAGG
2751 TAGCTTGCAGTGGGCTTACATGGCGATAGCTAGACTGGGCGGTTTTATGG
2801 ACAGCAAGCGAACCGGAATTGCCAGCTGGGGCGCCCTCTGGTAAGGTTGG
```

Figure 12b

```
2851  GAAGCCCTGCAAAGTAAACTGGATGGCTTTCTTGCCGCCAAGGATCTGAT
2901  GGCGCAGGGGATCAAGATCTGATCAAGAGACAGGATGAGGATCGTTTCGC
2951  ATGATTGAACAAGATGGATTGCACGCAGGTTCTCCGGCCGCTTGGGTGGA
3001  GAGGCTATTCGGCTATGACTGGGCACAACAGACAATCGGCTGCTCTGATG
3051  CCGCCGTGTTCCGGCTGTCAGCGCAGGGGCGCCCGGTTCTTTTTGTCAAG
3101  ACCGACCTGTCCGGTGCCCTGAATGAACTGCAGGACGAGGCAGCGCGGCT
3151  ATCGTGGCTGGCCACGACGGGCGTTCCTTGCGCAGCTGTGCTCGACGTTG
3201  TCACTGAAGCGGGAAGGGACTGGCTGCTATTGGGCGAAGTGCCGGGGCAG
3251  GATCTCCTGTCATCTCACCTTGCTCCTGCCGAGAAAGTATCCATCATGGC
3301  TGATGCAATGCGGCGGCTGCATACGCTTGATCCGGCTACCTGCCCATTCG
3351  ACCACCAAGCGAAACATCGCATCGAGCGAGCACGTACTCGGATGGAAGCC
3401  GGTCTTGTCGATCAGGATGATCTGGACGAAGAGCATCAGGGGCTCGCGCC
3451  AGCCGAACTGTTCGCCAGGCTCAAGGCGCGCATGCCCGACGGCGAGGATC
3501  TCGTCGTGACCCATGGCGATGCCTGCTTGCCGAATATCATGGTGGAAAAT
3551  GGCCGCTTTTCTGGATTCATCGACTGTGGCCGGCTGGGTGTGGCGGACCG
3601  CTATCAGGACATAGCGTTGGCTACCCGTGATATTGCTGAAGAGCTTGGCG
3651  GCGAATGGGCTGACCGCTTCCTCGTGCTTTACGGTATCGCCGCTCCCGAT
3701  TCGCAGCGCATCGCCTTCTATCGCCTTCTTGACGAGTTCTTCTGAGCGGG
3751  ACTCTGGGGTTCGAAATGACCGACCAAGCGACGCCCAACCTGCCATCACG
3801  AGATTTCGATTCCACCGCCGCCTTCTATGAAAGGTTGGGCTTCGGAATCG
3851  TTTTCCGGGACGCCGGCTGGATGATCCTCCAGCGCGGGGATCTCATGCTG
3901  GAGTTCTTCGCCCACCCCAACCCTGGCCCTATTATTGGGTGGACTAACCA
3951  TGGGGGGAATTGCCGCTGGAATAGGAACAGGGACTACTGCTCTAATGGCC
4001  ACTCAGCAATTCCAGCAGCTCCAAGCCGCAGTACAGGATGATCTCAGGGA
4051  GGTTGAAAAATCAATCTCTAACCTAGAAAGTCTCTCACTTCCCTGTCTG
4101  AAGTTGTCCTACAGAATCGAAGGGGCCTAGACTTGTTATTTCTAAAAGAA
4151  GGAGGGCTGTGTGCTGCTCTAAAAGAAGAATGTTGCTTCTATGCGGACCA
4201  CACAGGACTAGTGAGAGACAGCATGGCCAAATTGAGAGAGAGGCTTAATC
4251  AGAGACAGAAACTGTTTGAGTCAACTCAAGGATGGTTTGAGGGACTGTTT
4301  AACAGATCCCCTTGGTTTACCACCTTGATATCTACCATTATGGGACCCCT
4351  CATTGTACTCCTAATGATTTTGCTCTTCGGACCCTGCATTCTTAATCGAT
4401  TAGTCCAATTTGTTAAAGACAGGATATCAGTGGTCCAGGCTCTAGTTTTG
4451  ACTCAACAATATCACCAGCTGAAGCCTATAGAGTACGAGCCATAGATAAA
4501  ATAAAAGATTTTATTTAGTCTCCAGAAAAAGGGGGGAATGAAAGACCCCA
4551  CCTGTAGGTTTGGCAAGCTAGCTTAAGTAACGCCATTTTGCAAGGCATGG
4601  AAAAATACATAACTGAGAATAGAGAAGTTCAGATCAAGGTCAGGAACAGA
4651  TGGAACAGCTGAATATGGGCCAAACAGGATATCTGTGGTAAGCAGTTCCT
4701  GCCCCGGCTCAGGGCCAAGAACAGATGGAACAGCTGAATATGGGCCAAAC
4751  AGGATATCTGTGGTAAGCAGTTCCTGCCCCGGCTCAGGGCCAAGAACAGA
4801  TGGTCCCCAGATGCGGTCCAGCCCTCAGCAGTTTCTAGAGAACCATCAGA
4851  TGTTTCCAGGGTGCCCCAAGGACCTGAAATGACCCTGTGCCTTATTTGAA
4901  CTAACCAATCAGTTCGCTTCTCGCTTCTGTTCGCGCGCTTCTGCTCCCCG
4951  AGCTCAATAAAAGAGCCCACAACCCCTCACTCGGGGCGCCAGTCCTCCGA
5001  TTGACTGAGTCGCCCGGGTACCCGTGTATCCAATAAACCCTCTTGCAGTT
5051  GCATCCGACTTGTGGTCTCGCTGTTCCTTGGGAGGGTCTCCTCTGAGTGA
5101  TTGACTACCCGTCAGCGGGGGTCTTTCATT
```

| | |
|---|---|
| 1 – 589 | MoMuSV 5' LTR |
| 659 – 897 | Retroviral packaging region |
| 1034 – 1714 | Hepatitis B surface antigen |
| 2279 – 2595 | RSV promoter |
| 2951 – 3745 | Neomycin phosphotransferase gene |
| 4537 – 5130 | MoMuLV 3' LTR |

Figure 13a
SEQ ID NO:10
Alpha-Lactalbumin cc49IL2 Vector

| | |
|---|---|
| 1 | GATCAGTCCTGGGTGGTCATTGAAAGGACTGATGCTGAAGTTGAAGCTCC |
| 51 | AATACTTTGGCCACCTGATGCGAAGAACTGACTCATGTGATAAGACCCTG |
| 101 | ATACTGGGAAAGATTGAAGGCAGGAGGAGAAGGGATGACAGAGGATGGAA |
| 151 | GAGTTGGATGGAATCACCAACTCGATGGACATGAGTTTGAGCAAGCTTCC |
| 201 | AGGAGTTGGTAATGGGCAGGGAAGCCTGGCGTGCTGCAGTCCATGGGGTT |
| 251 | GCAAAGAGTTGGACACTACTGAGTGACTGAACTGAACTGATAGTGTAATC |
| 301 | CATGGTACAGAATATAGGATAAAAAGAGGAAGAGTTTGCCCTGATTCTG |
| 351 | AAGAGTTGTAGGATATAAAAGTTTAGAATACCTTTAGTTTGGAAGTCTTA |
| 401 | AATTATTTACTTAGGATGGGTACCCACTGCAATATAAGAAATCAGGCTTT |
| 451 | AGAGACTGATGTAGAGAGAATGAGCCCTGGCATACCAGAAGCTAACAGCT |
| 501 | ATTGGTTATAGCTGTTATAACCAATATATAACCAATATATTGGTTATATA |
| 551 | GCATGAAGCTTGATGCCAGCAATTTGAAGGAACCATTTAGAACTAGTATC |
| 601 | CTAAACTCTACATGTTCCAGGACACTGATCTTAAAGCTCAGGTTCAGAAT |
| 651 | CTTGTTTTATAGGCTCTAGGTGTATATTGTGGGCTTCCCTGGTGGCTCA |
| 701 | GATGGTAAAGTGTCTGCCTGCAATGTGGGTGATCTGGGTTCGATCCCTGG |
| 751 | CTTGGGAAGATCCCCTGGAGAAGGAAATGGCAACCCACTCTAGTACTCTT |
| 801 | ACCTGGAAAATTCCATGGACAGAGGAGCCTTGTAAGCTACAGTCCATGGG |
| 851 | ATTGCAAAGAGTTGAACACAACTGAGCAACTAAGCACAGCACAGTACAGT |
| 901 | ATACACCTGTGAGGTGAAGTGAAGTGAAGGTTCAATGCAGGGTCTCCTGC |
| 951 | ATTGCAGAAAGATTCTTTACCATCTGAGCCACCAGGGAAGCCCAAGAATA |
| 1001 | CTGGAGTGGGTAGCCTATTCCTTCTCCAGGGGATCTTCCCATCCCAGGAA |
| 1051 | TTGAACTGGAGTCTCCTGCATTTCAGGTGGATTCTTCACCAGCTGAACTA |
| 1101 | CCAGGTGGATACTACTCCAATATTAAAGTGCTTAAAGTCCAGTTTTCCCA |
| 1151 | CCTTTCCCAAAAAGGTTGGGTCACTCTTTTTAACCTTCTGTGGCCTACT |
| 1201 | CTGAGGCTGTCTACAAGCTTATATATTTATGAACACATTTATTGCAAGTT |
| 1251 | GTTAGTTTTAGATTTACAATGTGGTATCTGGCTATTTAGTGGTATTGGTG |
| 1301 | GTTGGGGATGGGGAGGCTGATAGCATCTCAGAGGGCAGCTAGATACTGTC |
| 1351 | ATACACACTTTTCAAGTTCTCCATTTTTGTGAAATAGAAAGTCTCTGGAT |
| 1401 | CTAAGTTATATGTGATTCTCAGTCTCTGTGGTCATATTCTATTCTACTCC |
| 1451 | TGACCACTCAACAAGGAACCAAGATATCAAGGGACACTTGTTTTGTTTCA |
| 1501 | TGCCTGGGTTGAGTGGGCCATGACATATGTTCTGGGCCTTGTTACATGGC |
| 1551 | TGGATTGGTTGGACAAGTGCCAGCTCTGATCCTGGGACTGTGGCATGTGA |
| 1601 | TGACATACACCCCCTCTCCACATTCTGCATGTCTCTAGGGGGAAGGGGG |
| 1651 | AAGCTCGGTATAGAACCTTTATTGTATTTCTGATTGCCTCACTTCTTAT |
| 1701 | ATTGCCCCCATGCCCTTCTTTGTTCCTCAAGTAACCAGAGACAGTGCTTC |
| 1751 | CCAGAACCAACCCTACAAGAAACAAAGGGCTAAACAAAGCCAAATGGGAA |
| 1801 | GCAGGATCATGGTTTGAACTCTTTCTGGCCAGAGAACAATACCTGCTATG |
| 1851 | GACTAGATACTGGGAGAGGGAAAGGAAAGTAGGGTGAATTATGGAAGGA |
| 1901 | AGCTGGCAGGCTCAGCGTTTCTGTCTTGGCATGACCAGTCTCTCTTCATT |
| 1951 | CTCTTCCTAGATGTAGGGCTTGGTACCAGAGCCCCTGAGGCTTTCTGCAT |
| 2001 | GAATATAAATATATGAAACTGAGTGATGCTTCCATTTCAGGTTCTTGGGG |
| 2051 | GCGCCGAATTCGAGCTCGGTACCCGGGGATCTCGAGAAGCTTTAACCATG |
| 2101 | GAATGGAGCTGGGTCTTTCTCTTCTTCCTGTCAGTAACTACAGGTGTCCA |
| 2151 | CTCCCAGGTTCAGTTGCAGCAGTCTGACGCTGAGTTGGTGAAACCTGGGG |
| 2201 | CTTCAGTGAAGATTTCCTGCAAGGCTTCTGGCTACACCTTCACTGACCAT |
| 2251 | GCAATTCACTGGGTGAAACAGAACCCTGAACAGGGCCTGGAATGGATTGG |
| 2301 | ATATTTTTCTCCCGGAAATGATGATTTTAAATACAATGAGAGGTTCAAGG |
| 2351 | GCAAGGCCACACTGACTGCAGACAAATCCTCCAGCACTGCCTACGTGCAG |
| 2401 | CTCAACAGCCTGACATCTGAGGATTCTGCAGTGTATTTCTGTACAAGATC |
| 2451 | CCTGAATATGGCCTACTGGGGTCAAGGAACCTCAGTCACCGTCTCCTCAG |
| 2501 | GAGGCGGAGGCAGCGGAGGCGGTGGCTCGGGAGGCGGAGGCTCGGACATT |
| 2551 | GTGATGTCACAGTCTCCATCCTCCCTACCTGTGTCAGTTGGCGAGAAGGT |
| 2601 | TACTTTGAGCTGCAAGTCCAGTCAGAGCCTTTTATATAGTGGTAATCAAA |
| 2651 | AGAACTACTTGGCCTGGTACCAGCAGAAACCAGGGCAGTCTCCTAAACTG |
| 2701 | CTGATTTACTGGGCATCCGCTAGGGAATCTGGGGTCCCTGATCGCTTCAC |
| 2751 | AGGCAGTGGATCTGGGACAGATTTCACTCTCTCCATCAGCAGTGTGAAGA |
| 2801 | CTGAAGACCTGGCAGTTTATTACTGTCAGCAGTATTATAGCTATCCCCTC |

Figure 13b

```
2851  ACGTTCGGTGCTGGGACCAAGCTGGTGCTGAAACGGGCCGCCGAGCCCAA
2901  ATCTCCTGACAAAACTCACACATGCCCACCGTGCCCAGCACCTGAACTCC
2951  TGGGGGGACCGTCAGTCTTCCTCTTCCCCCCAAAACCCAAGGACACCCTC
3001  ATGATCTCCCGGACCCCTGAGGTCACATGCGTGGTGGTGGACGTGAGCCA
3051  CGAAGACCCTGAGGTCAAGTTCAACTGGTACGTGGACGGCGTGGAGGTGC
3101  ATAATGCCAAGACAAAGCCGCGGGAGGAGCAGTACAACAGCACGTACCGT
3151  GTGGTCAGCGTCCTCACCGTCCTGCACCAGGACTGGCTGAATGGCAAGGA
3201  GTACAAGTGCAAGGTCTCCAACAAAGCCCTCCCAGCCCCCATCGAGAAAA
3251  CCATCTCCAAAGCCAAAGGGCAGCCCCGAGAACCACAGGTGTACACCCTG
3301  CCCCCATCCCGGGATGAGCTGACCAAGAACCAGGTCAGCCTGACCTGCCT
3351  GGTCAAAGGCTTCTATCCCAGCGACATCGCCGTGGAGTGGGAGAGCAATG
3401  GGCAGCCGGAGAACAACTACAAGACCACGCCTCCCGTGCTGGACTCCGAC
3451  GGCTCCTTCTTCCTCTACAGCAAGCTCACCGTGGACAAGAGCAGGTGGCA
3501  GCAGGGGAACGTCTTCTCATGCTCCGTGATGCATGAGGCTCTGCACAACC
3551  ACTACACGCAGAAGAGCCTCTCCCTGTCTCCGGGTAAAGGAGGCGGATCA
3601  GGAGGTGGCGCACCTACTTCAAGTTCTACAAAGAAAACACAGCTACAACT
3651  GGAGCATTTACTGCTGGATTTACAGATGATTTTGAATGGAATTAATAATT
3701  ACAAGAATCCCAAACTCACCAGGATGCTCACATTTAAGTTTTACATGCCC
3751  AAGAAGGCCACAGAACTGAAACATCTTCAGTGTCTAGAAGAAGAACTCAA
3801  ACCTCTGGAGGAAGTGCTAAATTTAGCTCAAAGCAAAAACTTTCACTTAA
3851  GACCCAGGGACTTAATCAGCAATATCAACGTAATAGTTCTGGAACTAAAG
3901  GGATCTGAAACAACATTCATGTGTGAATATGCTGATGAGACAGCAACCAT
3951  TGTAGAATTTCTGAACAGATGGATTACCTTTTGTCAAAGCATCATCTCAA
4001  CACTAACTTGAAGCTTGTTAACATCGATAAAATAAAAGATTTTATTTAGT
4051  CTCCAGAAAAAGGGGGGAATGAAAGACCCCACCTGTAGGTTTGGCAAGCT
4101  AGCTTAAGTAACGCCATTTTGCAAGGCATGGAAAAATACATAACTGAGAA
4151  TAGAGAAGTTCAGATCAAGGTCAGGAACAGATGGAACAGCTGAATATGGG
4201  CCAAACAGGATATCTGTGGTAAGCAGTTCCTGCCCCGGCTCAGGGCCAAG
4251  AACAGATGGAACAGCTGAATATGGGCCAAACAGGATATCTGTGGTAAGCA
4301  GTTCCTGCCCCGGCTCAGGGCCAAGAACAGATGGTCCCCAGATGCGGTCC
4351  AGCCCTCAGCAGTTTCTAGAGAACCATCAGATGTTTCCAGGGTGCCCCAA
4401  GGACCTGAAATGACCCTGTGCCTTATTTGAACTAACCAATCAGTTCGCTT
4451  CTCGCTTCTGTTCGCGCGCTTCTGCTCCCGAGCTCAATAAAAGAGCCCA
4501  CAACCCCTCACTCGGGGCGCCAGTCCTCCGATTGACTGAGTCGCCCGGGT
4551  ACCCGTGTATCCAATAAACCCTCTTGCAGTTGCATCCGACTTGTGGTCTC
4601  GCTGTTCCTTGGGAGGGTCTCCTCTGAGTGATTGACTACCCGTCAGCGGG
4651  GGTCTTTCATT
```

| | |
|---|---|
| 1 - 2055 | Bovine/human alpha-lactalbumin 5' flanking region |
| 2098 - 4011 | cc49-IL2 coding region |
| 4068 - 4661 | MoMuLV 3' LTR |

Figure 14a
SEQ ID NO:11
Alpha-Lactalbumin YP Vector

```
   1  GATCAGTCCTGGGTGGTCATTGAAAGGACTGATGCTGAAGTTGAAGCTCC
  51  AATACTTTGGCCACCTGATGCGAAGAACTGACTCATGTGATAAGACCCTG
 101  ATACTGGGAAAGATTGAAGGCAGGAGGAGAAGGGATGACAGAGGATGGAA
 151  GAGTTGGATGGAATCACCAACTCGATGGACATGAGTTTGAGCAAGCTTCC
 201  AGGAGTTGGTAATGGGCAGGGAAGCCTGGCGTGCTGCAGTCCATGGGGTT
 251  GCAAAGAGTTGGACACTACTGAGTGACTGAACTGAACTGATAGTGTAATC
 301  CATGGTACAGAATATAGGATAAAAAGAGGAAGAGTTTGCCCTGATTCTG
 351  AAGAGTTGTAGGATATAAAAGTTTAGAATACCTTTAGTTTGGAAGTCTTA
 401  AATTATTTACTTAGGATGGGTACCCACTGCAATATAAGAAATCAGGCTTT
 451  AGAGACTGATGTAGAGAGAATGAGCCCTGGCATACCAGAAGCTAACAGCT
 501  ATTGGTTATAGCTGTTATAACCAATATATAACCAATATATTGGTTATATA
 551  GCATGAAGCTTGATGCCAGCAATTTGAAGGAACCATTTAGAACTAGTATC
 601  CTAAACTCTACATGTTCCAGGACACTGATCTTAAAGCTCAGGTTCAGAAT
 651  CTTGTTTTATAGGCTCTAGGTGTATATTGTGGGCTTCCCTGGTGGCTCA
 701  GATGGTAAAGTGTCTGCCTGCAATGTGGGTGATCTGGGTTCGATCCCTGG
 751  CTTGGGAAGATCCCCTGGAGAAGGAAATGGCAACCCACTCTAGTACTCTT
 801  ACCTGGAAAATTCCATGGACAGAGGAGCCTTGTAAGCTACAGTCCATGGG
 851  ATTGCAAAGAGTTGAACACAACTGAGCAACTAAGCACAGCACAGTACAGT
 901  ATACACCTGTGAGGTGAAGTGAAGTGAAGGTTCAATGCAGGGTCTCCTGC
 951  ATTGCAGAAAGATTCTTTACCATCTGAGCCACCAGGGAAGCCCAAGAATA
1001  CTGGAGTGGGTAGCCTATTCCTTCTCCAGGGGATCTTCCCATCCCAGGAA
1051  TTGAACTGGAGTCTCCTGCATTTCAGGTGGATTCTTCACCAGCTGAACTA
1101  CCAGGTGGATACTACTCCAATATTAAAGTGCTTAAAGTCCAGTTTTCCCA
1151  CCTTTCCCAAAAAGGTTGGGTCACTCTTTTTTAACCTTCTGTGGCCTACT
1201  CTGAGGCTGTCTACAAGCTTATATATTTATGAACACATTTATTGCAAGTT
1251  GTTAGTTTTAGATTTACAATGTGGTATCTGGCTATTTAGTGGTATTGGTG
1301  GTTGGGGATGGGGAGGCTGATAGCATCTCAGAGGGCAGCTAGATACTGTC
1351  ATACACACTTTTCAAGTTCTCCATTTTTGTGAAATAGAAAGTCTCTGGAT
1401  CTAAGTTATATGTGATTCTCAGTCTCTGTGGTCATATTCTATTCTACTCC
1451  TGACCACTCAACAAGGAACCAAGATATCAAGGGACACTTGTTTTGTTTCA
1501  TGCCTGGGTTGAGTGGGCCATGACATATGTTCTGGGCCTTGTTACATGGC
1551  TGGATTGGTTGGACAAGTGCCAGCTCTGATCCTGGGACTGTGGCATGTGA
1601  TGACATACACCCCCTCTCCACATTCTGCATGTCTCTAGGGGGGAAGGGGG
1651  AAGCTCGGTATAGAACCTTTATTGTATTTTCTGATTGCCTCACTTCTTAT
1701  ATTGCCCCCATGCCCTTCTTTGTTCCTCAAGTAACCAGAGACAGTGCTTC
1751  CCAGAACCAACCCTACAAGAAACAAAGGGCTAAACAAAGCCAAATGGGAA
1801  GCAGGATCATGGTTTGAACTCTTTCTGGCCAGAGAACAATACCTGCTATG
1851  GACTAGATACTGGGAGAGGGAAAGGAAAAGTAGGGTGAATTATGGAAGGA
1901  AGCTGGCAGGCTCAGCGTTTCTGTCTTGGCATGACCAGTCTCTCTTCATT
1951  CTCTTCCTAGATGTAGGGCTTGGTACCAGAGCCCCTGAGGCTTTCTGCAT
2001  GAATATAAATATATGAAACTGAGTGATGCTTCCATTTCAGGTTCTTGGGG
2051  GCGCCGAATTCGAGCTCGGTACCCGGGGATCTCGACGGATCCGATTACTT
2101  ACTGGCAGGTGCTGGGGGCTTCCGAGACAATCGCGAACATCTACACCACA
2151  CAACACCGCCTCGACCAGGGTGAGATATCGGCCGGGACGCGGCGGTGGT
2201  AATTACAAGCGAGATCCGATTACTTACTGGCAGGTGCTGGGGGCTTCCGA
2251  GACAATCGCGAACATCTACACCACACAACACCGCCTCGACCAGGGTGAGA
2301  TATCGGCCGGGACGCGGCGGTGGTAATTACAAGCGAGATCTCGAGTTAA
2351  CAGATCTAGGCCTCCTAGGTCGACGGATCCCCGGGAATTCGGCGCCGCCA
2401  CCATGATGTCCTTTGTCTCTCTGCTCCTGGTAGGCATCCTATTCCATGCC
2451  ACCCAGGCCCAGGTCCAACTGCAGCAGTCTGGGCCTGAGCTGGTGAAGCC
2501  TGGGACTTCAGTGAGGATATCCTGCAAGGCTTCTGGCTACACCTTCACAA
2551  GCTACTATTTACACTGGGTGAAGCAGAGGCCTGGACAGGGACTTGAGTGG
2601  ATTGCATGGATTTATCCTGGAAATGTTATTACTACGTACAATGAGAAGTT
2651  CAAGGGCAAGGCCACACTGACTGCAGACAAATCCTCCAGCACAGCCTACA
2701  TGCACCTCAACAGCCTGACCTCTGAGGACTCTGCGGTCTATTTCTGTGCA
2751  AGGGGTGACCATGATCTTGACTACTGGGGCCAAGGCACCACTCTCACAGT
2801  CTCCTCAGCCAAAACGACACCCCCATCTGTCTATCCACTGGCCCCTGGAT
```

Figure 14b

```
2851  CTGCTGCCCAAACTAACTCCATGGTGACCCTGGGATGCCTGGTCAAGGGC
2901  TATTTCCCTGAGCCAGTGACAGTGACCTGGAACTCTGGATCCCTGTCCAG
2951  CGGTGTGCACACCTTCCCAGCTGTCCTGCAGTCTGACCTCTACACTCTGA
3001  GCAGCTCAGTGACTGTCCCCTCCAGCACCTGGCCCAGCGAGACCGTCACC
3051  TGCAACGTTGCCCACCCGGCCAGCAGCACCAAGGTGGACAAGAAAATTGT
3101  GCCCAGGGATTGTACTAGTGGAGGTGGAGGTAGCTAAGGGAGATCTCGAC
3151  GGATCCCCGGGAATTCGCCCCTCTCCCTCCCCCCCCCCTAACGTTACTGG
3201  CCGAAGCCGCTTGGAATAAGGCCGGTGTGCGTTTGTCTATATGTTATTTT
3251  CCACCATATTGCCGTCTTTTGGCAATGTGAGGGCCCGGAAACCTGGCCCT
3301  GTCTTCTTGACGAGCATTCCTAGGGGTCTTTCCCCTCTCGCCAAAGGAAT
3351  GCAAGGTCTGTTGAATGTCGTGAAGGAAGCAGTTCCTCTGGAAGCTTCTT
3401  GAAGACAAACAACGTCTGTAGCGACCCTTTGCAGGCAGCGGAACCCCCCA
3451  CCTGGCGACAGGTGCCTCTGCGGCCAAAAGCCACGTGTATAAGATACACC
3501  TGCAAAGGCGGCACAACCCCAGTGCCACGTTGTGAGTTGGATAGTTGTGG
3551  AAAGAGTCAAATGGCTCTCCTCAAGCGTATTCAACAAGGGGCTGAAGGAT
3601  GCCCAGAAGGTACCCCATTGTATGGGATCTGATCTGGGGCCTCGGTGCAC
3651  ATGCTTTACATGTGTTTAGTCGAGGTTAAAAAAACGTCTAGGCCCCCCGA
3701  ACCACGGGGACGTGGTTTTCCTTTGAAAAACACGATGATAATATGGCCTC
3751  CTTTGTCTCTCTGCTCCTGGTAGGCATCCTATTCCATGCCACCCAGGCCG
3801  ACATTGTGCTGACACAATCTCCAGCAATCATGTCTGCATCTCCAGGGGAG
3851  AAGGTCACCATGACCTGCAGTGCCACCTCAAGTGTAAGTTACATACACTG
3901  GTACCAGCAGAAGTCAGGCACCTCCCCCAAAAGATGGATTTATGACACAT
3951  CCAAACTGGCTTCTGGAGTCCCTGCTCGCTTCAGTGGCAGTGGGTCTGGG
4001  ACCTCTCACTCTCTCACACTCAGCAGCATGGAGGCTGAAGATGCTGCCAC
4051  TTATTACTGCCAGCAGTGGGGTAGTTACCTCACGTTCGGTGCGGGGACCA
4101  AGCTGGAGCTGAAACGGGCTGATGCTGCACCAACTGTATCCATCTTCCCA
4151  CCATCCAGTGAGCAGTTAACATCTGGAGGTGCCTCAGTCGTGTGCTTCTT
4201  GAACAACTTCTACCCCAAAGACATCAATGTCAAGTGGAAGATTGATGGCA
4251  GTGAACGACAAAATGGCGTCCTGAACAGTTGGACTGATCAGGACAGCAAA
4301  GACAGCACCTACAGCATGAGCAGCACCCTCACGTTGACCAAGGACGAGTA
4351  TGAACGACATAACAGCTATACCTGTGAGGCCACTCACAAGACATCAACTT
4401  CACCCATTGTCAAGAGCTTCAACAGGAATGAGTGTTAATAGGGGAGATCT
4451  CGACATCGATAATCAACCTCTGGATTACAAAATTTGTGAAAGATTGACTG
4501  GTATTCTTAACTATGTTGCTCCTTTTACGCTATGTGGATACGCTGCTTTA
4551  ATGCCTTTGTATCATGCTATTGCTTCCCGTATGGCTTTCATTTTCTCCTC
4601  CTTGTATAAATCCTGGTTGCTGTCTCTTTATGAGGAGTTGTGGCCCGTTG
4651  TCAGGCAACGTGGCGTGGTGTGCACTGTGTTTGCTGACGCAACCCCCACT
4701  GGTTGGGGCATTGCCACCACCTGTCAGCTCCTTTCCGGGACTTTCGCTTT
4751  CCCCCTCCCTATTGCCACGGCGGAACTCATCGCCGCCTGCCTTGCCCGCT
4801  GCTGGACAGGGGCTCGGCTGTTGGGCACTGACAATTCCGTGGTGTTGTCG
4851  GGGAAATCATCGTCCTTTCCTTGGCTGCTCGCCTGTGTTGCCACCTGGAT
4901  TCTGCGCGGGACGTCCTTCTGCTACGTCCCTTCGGCCCTCAATCCAGCGG
4951  ACCTTCCTTCCCGCGGCCTGCTGCCGGCTCTGCGGCCTCTTCCGCGTCTT
5001  CGCCTTCGCCCTCAGACGAGTCGGATCTCCCTTTGGGCCGCCTCCCCGCC
5051  TGATCGATAAAATAAAAGATTTTATTTAGTCTCCAGAAAAAGGGGGGAAT
5101  GAAAGACCCCACCTGTAGGTTTGGCAAGCTAGCTTAAGTAACGCCATTTT
5151  GCAAGGCATGGAAAATACATAACTGAGAATAGAGAAGTTCAGATCAAGG
5201  TCAGGAACAGATGGAACAGCTGAATATGGGCCAAACAGGATATCTGTGGT
5251  AAGCAGTTCCTGCCCCGGCTCAGGGCCAAGAACAGATGGAACAGCTGAAT
5301  ATGGGCCAAACAGGATATCTGTGGTAAGCAGTTCCTGCCCCGGCTCAGGG
5351  CCAAGAACAGATGGTCCCCAGATGCGGTCCAGCCCTCAGCAGTTTCTAGA
5401  GAACCATCAGATGTTTCCAGGGTGCCCCAAGGACCTGAAATGACCCTGTG
5451  CCTTATTTGAACTAACCAATCAGTTCGCTTCTCGCTTCTGTTCGCGCGCT
5501  TCTGCTCCCCGAGCTCAATAAAAGAGCCCACAACCCCTCACTCGGGGCGC
5551  CAGTCCTCCGATTGACTGAGTCGCCCGGGTACCCGTGTATCCAATAAACC
5601  CTCTTGCAGTTGCATCCGACTTGTGGTCTCGCTGTTCCTTGGGAGGGTCT
```

Figure 14c
5651 CCTCTGAGTGATTGACTACCCGTCAGCGGGGGTCTTTCATT

| | |
|---|---|
| 1 - 2053 | Bovine/Human Alpha-lactalbumin 5' flanking region |
| 2093 - 2336 | Double mutated PPE sequence |
| 2403 - 2459 | Bovine alpha-lactalbumin signal peptide coding region |
| 2460 - 3137 | Yersenia pestis heavy chain Fab gene coding region |
| 3167 - 3742 | EMCV IRES |
| 3743 - 3799 | Bovine alpha-lactalbumin signal peptide coding region |
| 3800 - 4441 | Yersenia pestis light chain Fab gene coding region |
| 4461 - 5052 | WPRE sequence |
| 5098 - 5691 | Moloney murine leukemia virus 3' LTR |

Figure 15
SEQ ID NO:12
IRES-Casein Signal Peptide Sequence

```
1    GGAATTCGCCCCTCTCCCTCCCCCCCCCCTAACGTTACTGGCCGAAGCCG
51   CTTGGAATAAGGCCGGTGTGCGTTTGTCTATATGTTATTTTCCACCATAT
101  TGCCGTCTTTTGGCAATGTGAGGGCCCGGAAACCTGGCCCTGTCTTCTTG
151  ACGAGCATTCCTAGGGGTCTTTCCCCTCTCGCCAAAGGAATGCAAGGTCT
201  GTTGAATGTCGTGAAGGAAGCAGTTCCTCTGGAAGCTTCTTGAAGACAAA
251  CAACGTCTGTAGCGACCCTTTGCAGGCAGCGGAACCCCCACCTGGCGAC
301  AGGTGCCTCTGCGGCCAAAAGCCACGTGTATAAGATACACCTGCAAAGGC
351  GGCACAACCCCAGTGCCACGTTGTGAGTTGGATAGTTGTGGAAAGAGTCA
401  AATGGCTCTCCTCAAGCGTATTCAACAAGGGGCTGAAGGATGCCCAGAAG
451  GTACCCCATTGTATGGGATCTGATCTGGGGCCTCGGTGCACATGCTTTAC
501  ATGTGTTTAGTCGAGGTTAAAAAAACGTCTAGGCCCCCCGAACCACGGGG
551  ACGTGGTTTTCCTTTGAAAAACACGATGATAATATGGCCTTGCTCATCCT
601  TACCTGTCTTGTGGCTGTTGCTCTTGCCGGCGCCATGGGATATCTAGATC
651  TCGAGCTCGCGAAAGCTT
```

| | |
|---|---|
| 1 - 583 | IRES |
| 584 - 628 | Modified bovine alpha-S1 casein signal peptide coding region |
| 629 - 668 | Multiple cloning site |

Figure 16a

SEQ ID NO: 13

LNBOTDC Vector

```
   1   TTTGAAAGACCCCACCCGTAGGTGGCAAGCTAGCTTAAGTAACGCCACTT
  51   TGCAAGGCATGGAAAAATACATAACTGAGAATAGAAAAGTTCAGATCAAG
 101   GTCAGGAACAAAGAAACAGCTGAATACCAAACAGGATATCTGTGGTAAGC
 151   GGTTCCTGCCCCGGCTCAGGGCCAAGAACAGATGAGACAGCTGAGTGATG
 201   GGCCAAACAGGATATCTGTGGTAAGCAGTTCCTGCCCCGGCTCGGGGCCA
 251   AGAACAGATGGTCCCCAGATGCGGTCCAGCCCTCAGCAGTTTCTAGTGAA
 301   TCATCAGATGTTTCCAGGGTGCCCCAAGGACCTGAAAATGACCCTGTACC
 351   TTATTTGAACTAACCAATCAGTTCGCTTCTCGCTTCTGTTCGCGCGCTTC
 401   CGCTCTCCGAGCTCAATAAAAGAGCCCACAACCCCTCACTCGGCGCGCCA
 451   GTCTTCCGATAGACTGCGTCGCCCGGGTACCCGTATTCCCAATAAAGCCT
 501   CTTGCTGTTTGCATCCGAATCGTGGTCTCGCTGTTCCTTGGGAGGGTCTC
 551   CTCTGAGTGATTGACTACCCACGACGGGGGTCTTTCATTTGGGGGCTCGT
 601   CCGGGATTTGGAGACCCCTGCCCAGGGACCACCGACCCACCACCGGGAGG
 651   TAAGCTGGCCAGCAACTTATCTGTGTCTGTCCGATTGTCTAGTGTCTATG
 701   TTTGATGTTATGCGCCTGCGTCTGTACTAGTTAGCTAACTAGCTCTGTAT
 751   CTGGCGGACCCGTGGTGGAACTGACGAGTTCTGAACACCCGGCCGCAACC
 801   CTGGGAGACGTCCCAGGGACTTTGGGGGCCGTTTTTGTGGCCCGACCTGA
 851   GGAAGGGAGTCGATGTGGAATCCGACCCCGTCAGGATATGTGGTTCTGGT
 901   AGGAGACGAGAACCTAAAACAGTTCCCGCCTCCGTCTGAATTTTTGCTTT
 951   CGGTTTGGAACCGAAGCCGCGCGTCTTGTCTGCTGCAGCGCTGCAGCATC
1001   GTTCTGTGTTGTCTCTGTCTGACTGTGTTTCTGTATTTGTCTGAAAATTA
1051   GGGCCAGACTGTTACCACTCCCTTAAGTTTGACCTTAGGTCACTGGAAAG
1101   ATGTCGAGCGGATCGCTCACAACCAGTCGGTAGATGTCAAGAAGAGACGT
1151   TGGGTTACCTTCTGCTCTGCAGAATGGCCAACCTTTAACGTCGGATGGCC
1201   GCGAGACGGCACCTTTAACCGAGACCTCATCACCCAGGTTAAGATCAAGG
1251   TCTTTTCACCTGGCCCGCATGGACACCCAGACCAGGTCCCCTACATCGTG
1301   ACCTGGGAAGCCTTGGCTTTTGACCCCCCTCCCTGGGTCAAGCCCTTTGT
1351   ACACCCTAAGCCTCCGCCTCCTCTTCCTCCATCCGCCCCGTCTCTCCCCC
1401   TTGAACCTCCTCGTTCGACCCCGCCTCGATCCTCCCTTTATCCAGCCCTC
1451   ACTCCTTCTCTAGGCGCCGGAATTCCGATCTGATCAAGAGACAGGATGAG
1501   GATCGTTTCGCATGATTGAACAAGATGGATTGCACGCAGGTTCTCCGGCC
1551   GCTTGGGTGGAGAGGCTATTCGGCTATGACTGGGCACAACAGACAATCGG
1601   CTGCTCTGATGCCGCCGTGTTCCGGCTGTCAGCGCAGGGGCGCCCGGTTC
1651   TTTTTGTCAAGACCGACCTGTCCGGTGCCCTGAATGAACTGCAGGACGAG
1701   GCAGCGCGGCTATCGTGGCTGGCCACGACGGGCGTTCCTTGCGCAGCTGT
1751   GCTCGACGTTGTCACTGAAGCGGGAAGGGACTGGCTGCTATTGGGCGAAG
1801   TGCCGGGGCAGGATCTCCTGTCATCTCACCTTGCTCCTGCCGAGAAAGTA
1851   TCCATCATGGCTGATGCAATGCGGCGGCTGCATACGCTTGATCCGGCTAC
1901   CTGCCCATTCGACCACCAAGCGAAACATCGCATCGAGCGAGCACGTACTC
1951   GGATGGAAGCCGGTCTTGTCGATCAGGATGATCTGGACGAAGAGCATCAG
2001   GGGCTCGCGCCAGCCGAACTGTTCGCCAGGCTCAAGGCGCGCATGCCCGA
2051   CGGCGAGGATCTCGTCGTGACCCATGGCGATGCCTGCTTGCCGAATATCA
2101   TGGTGGAAAATGGCCGCTTTTCTGGATTCATCGACTGTGGCCGGCTGGGT
2151   GTGGCGGACCGCTATCAGGACATAGCGTTGGCTACCCGTGATATTGCTGA
2201   AGAGCTTGGCGGCGAATGGGCTGACCGCTTCCTCGTGCTTTACGGTATCG
2251   CCGCTCCCGATTCGCAGCGCATCGCCTTCTATCGCCTTCTTGACGAGTTC
2301   TTCTGAGCGGGACTCTGGGGTTCGAAATGACCGACCAAGCGACGCCCAAC
2351   CTGCCATCACGAGATTTCGATTCCACCGCCGCCTTCTATGAAAGGTTGGG
2401   CTTCGGAATCGTTTTCCGGGACGCCGGCTGGATGATCCTCCAGCGCGGGG
2451   ATCTCATGCTGGAGTTCTTCGCCCACCCCGGGCTCGATCCCCTCGCGAGT
2501   TGGTTCAGCTGCTGCCTGAGGCTGGACGACCTCGCGGAGTTCTACCGGCA
2551   GTGCAAATCCGTCGGCATCCAGGAAACCAGCAGCGGCTATCCGCGCATCC
2601   ATGCCCCCGAACTGCAGGAGTGGGGAGGCACGATGGCCGCTTTGGTCGAG
2651   GCGGATCCGGCCATTAGCCATATTATTCATTGGTTATATAGCATAAATCA
2701   ATATTGGCTATTGGCCATTGCATACGTTGTATCCATATCATAATATGTAC
2751   ATTTATATTGGCTCATGTCCAACATTACCGCCATGTTGACATTGATTATT
```

Figure 16b

```
2801 GACTAGTTATTAATAGTAATCAATTACGGGGTCATTAGTTCATAGCCCAT
2851 ATATGGAGTTCCGCGTTACATAACTTACGGTAAATGGCCCGCCTGGCTGA
2901 CCGCCCAACGACCCCCGCCCATTGACGTCAATAATGACGTATGTTCCCAT
2951 AGTAACGCCAATAGGGACTTTCCATTGACGTCAATGGGTGGAGTATTTAC
3001 GGTAAACTGCCCACTTGGCAGTACATCAAGTGTATCATATGCCAAGTACG
3051 CCCCCTATTGACGTCAATGACGGTAAATGGCCCGCCTGGCATTATGCCCA
3101 GTACATGACCTTATGGGACTTTCCTACTTGGCAGTACATCTACGTATTAG
3151 TCATCGCTATTACCATGGTGATGCGGTTTTGGCAGTACATCAATGGGCGT
3201 GGATAGCGGTTTGACTCACGGGGATTTCCAAGTCTCCACCCCATTGACGT
3251 CAATGGGAGTTTGTTTTGGCACCAAAATCAACGGGACTTTCCAAAATGTC
3301 GTAACAACTCCGCCCCATTGACGCAAATGGGCGGTAGGCATGTACGGTGG
3351 GAGGTCTATATAAGCAGAGCTCGTTTAGTGAACCGTCAGATCGCCTGGAG
3401 ACGCCATCCACGCTGTTTTGACCTCCATAGAAGACACCGGGACCGATCCA
3451 GCCTCCGCGGCCCCAAGCTTCTCGACGGATCCCCGGGAATTCAGGCCATC
3501 GATCCCGCCGCCACCATGGAATGGAGCTGGGTCTTTCTCTTCCTGTC
3551 AGTAACTACAGGTGTCCACTCCGACATCCAGATGACCCAGTCTCCAGCCT
3601 CCCTATCTGCATCTGTGGGAGAAACTGTCACTATCACATGTCGAGCAAGT
3651 GGGAATATTCACAATTATTTAGCATGGTATCAGCAGAAACAGGGAAAATC
3701 TCCTCAGCTCCTGGTCTATAATGCAAAAACCTTAGCAGATGGTGTGCCAT
3751 CAAGGTTCAGTGGCAGTGGATCAGGAACACAATATTCTCTCAAGATCAAC
3801 AGCCTGCAGCCTGAAGATTTTGGGAGTTATTACTGTCAACATTTTTGGAG
3851 TACTCCGTGGACGTTCGGTGGAGGCACCAAGCTGGAAATCAAACGGGCTG
3901 ATGCTGCACCAACTGTATCCATCTTCCCACCATCCAGTGAGCAGTTAACA
3951 TCTGGAGGTGCCTCAGTCGTGTGCTTCTTGAACAACTTCTACCCCAAAGA
4001 CATCAATGTCAAGTGGAAGATTGATGGCAGTGAACGACAAAATGGCGTCC
4051 TGAACAGTTGGACTGATCAGGACAGCAAAGACAGCACCTACAGCATGAGC
4101 AGCACCCTCACATTGACCAAGGACGAGTATGAACGACATAACAGCTATAC
4151 CTGTGAGGCCACTCACAAGACATCAACTTCACCCATTGTCAAGAGCTTCA
4201 ACAGGAATGAGTGTTGAAAGCATCGATTTCCCCTGAATTCGCCCCTCTCC
4251 CTCCCCCCCCCCCTAACGTTACTGGCCGAAGCCGCTTGGAATAAGGCCGGT
4301 GTGCGTTTGTCTATATGTTATTTTCCACCATATTGCCGTCTTTTGGCAAT
4351 GTGAGGGCCCGGAAACCTGGCCCTGTCTTCTTGACGAGCATTCCTAGGGG
4401 TCTTTCCCCTCTCGCCAAAGGAATGCAAGGTCTGTTGAATGTCGTGAAGG
4451 AAGCAGTTCCTCTGGAAGCTTCTTGAAGACAAACAACGTCTGTAGCGACC
4501 CTTTGCAGGCAGCGGAACCCCCCACCTGGCGACAGGTGCCTCTGCGGCCA
4551 AAAGCCACGTGTATAAGATACACCTGCAAAGGCGGCACAACCCCAGTGCC
4601 ACGTTGTGAGTTGGATAGTTGTGGAAAGAGTCAAATGGCTCTCCTCAAGC
4651 GTATTCAACAAGGGGCTGAAGGATGCCCAGAAGGTACCCCATTGTATGGG
4701 ATCTGATCTGGGGCCTCGGTGCACATGCTTTACATGTGTTTAGTCGAGGT
4751 TAAAAAAACGTCTAGGCCCCCCGAACCACGGGGACGTGGTTTTCCTTTGA
4801 AAAACACGATGATAATATGGCCTCCTTTGTCTCTCTGCTCCTGGTAGGCA
4851 TCCTATTCCATGCCACCCAGGCCGAGGTTCAGCTTCAGCAGTCTGGGGCA
4901 GAGCTTGTGAAGCCAGGGGCCTCAGTCAAGTTGTCCTGCACAGCTTCTGG
4951 CTTCAACATTAAAGACACCTTTATGCACTGGGTGAAGCAGAGGCCTGAAC
5001 AGGGCCTGGAGTGGATTGGAAGGATTGATCCTGCGAATGGGAATACTGAA
5051 TATGACCCGAAGTTCCAGGGCAAGGCCACTATAACAGCAGACACATCCTC
5101 CAACACAGTCAACCTGCAGCTCAGCAGCCTGACATCTGAGGACACTGCCG
5151 TCTATTACTGTGCTAGTGGAGGGGAACTGGGGTTTCCTTACTGGGGCCAA
5201 GGGACTCTGGTCACTGTCTCTGCAGCCAAAACGACACCCCCATCTGTCTA
5251 TCCACTGGCCCCTGGATCTGCTGCCCAAACTAACTCCATGGTGACCCTGG
5301 GATGCCTGGTCAAGGGCTATTTCCCTGAGCCAGTGACAGTGACCTGGAAC
5351 TCTGGATCCCTGTCCAGCGGTGTGCACACCTTCCCAGCTGTCCTGCAGTC
5401 TGACCTCTACACTCTGAGCAGCTCAGTGACTGTCCCCTCCAGCACCTGGC
5451 CCAGCGAGACCGTCACCTGCAACGTTGCCCACCCGGCCAGCAGCACCAAG
5501 GTGGACAAGAAAATTGTGCCCAGGGATTGTACTAGTGGAGGTGGAGGTAG
5551 CCACCATCACCATCACCATTAATCTAGAGTTAAGCGGCCGTCGAGATCTA
5601 GGCCTCCTAGGTCGACATCGATAAAATAAAAGATTTTATTTAGTCTCCAG
5651 AAAAAGGGGGGAATGAAAGACCCCACCTGTAGGTTTGGCAAGCTAGCTTA
5701 AGTAACGCCATTTTGCAAGGCATGGAAAAATACATAACTGAGAATAGAGA
5751 AGTTCAGATCAAGGTCAGGAACAGATGGAACAGCTGAATATGGGCCAAAC
5801 AGGATATCTGTGGTAAGCAGTTCCTGCCCCGGCTCAGGGCCAAGAACAGA
5851 TGGAACAGCTGAATATGGGCCAAACAGGATATCTGTGGTAAGCAGTTCCT
```

Figure 16c

```
5901  GCCCCGGCTCAGGGCCAAGAACAGATGGTCCCCAGATGCGGTCCAGCCCT
5951  CAGCAGTTTCTAGAGAACCATCAGATGTTTCCAGGGTGCCCCAAGGACCT
6001  GAAATGACCCTGTGCCTTATTTGAACTAACCAATCAGTTCGCTTCTCGCT
6051  TCTGTTCGCGCGCTTCTGCTCCCCGAGCTCAATAAAAGAGCCCACAACCC
6101  CTCACTCGGGGCGCCAGTCCTCCGATTGACTGAGTCGCCCGGGTACCCGT
6151  GTATCCAATAAACCCTCTTGCAGTTGCATCCGACTTGTGGTCTCGCTGTT
6201  CCTTGGGAGGGTCTCCTCTGAGTGATTGACTACCCGTCAGCGGGGGTCTT
      TCATT
```

| | |
|---|---|
| Moloney Murine Sarcoma Virus 5' LTR | 1 - 589 |
| Moloney Murine Leukemia Virus Extended Packaging Region | 659 - 1468 |
| Neomycin Resistance Gene | 1512 - 2306 |
| CMV Promoter | 2656 - 3473 |
| cc49 Signal Peptide Coding Region | 3516 - 3572 |
| Bot Fab 5 Light Chain | 3573 - 4217 |
| EMCV IRES (Clonetech) | 4235 - 4816 |
| Modified Bovine α-LA Signal Peptide Coding Region | 4817 - 4873 |
| Bot Fab 5 Heavy Chain | 4874 - 5572 |
| Moloney Murine Leukemia Virus 3' LTR | 5662 - 6255 |

Figure 17a
SEQ ID NO: 34
LNBOTDC Vector

```
   1 GAATTAATTCATACCAGATCACCGAAAACTGTCCTCCAAATGTGTCCCCC
  51 TCACACTCCCAAATTCGCGGGCTTCTGCCTCTTAGACCACTCTACCCTAT
 101 TCCCCACACTCACCGGAGCCAAAGCCGCGGCCCTTCCGTTTCTTTGCTTT
 151 TGAAAGACCCCACCCGTAGGTGGCAAGCTAGCTTAAGTAACGCCACTTTG
 201 CAAGGCATGGAAAAATACATAACTGAGAATAGAAAAGTTCAGATCAAGGT
 251 CAGGAACAAAGAAACAGCTGAATACCAAACAGGATATCTGTGGTAAGCGG
 301 TTCCTGCCCCGGCTCAGGGCCAAGAACAGATGAGACAGCTGAGTGATGGG
 351 CCAAACAGGATATCTGTGGTAAGCAGTTCCTGCCCCGGCTCGGGCCAAG
 401 AACAGATGGTCCCCAGATGCGGTCCAGCCCTCAGCAGTTTCTAGTGAATC
 451 ATCAGATGTTTCCAGGGTGCCCCAAGGACCTGAAAATGACCCTGTACCTT
 501 ATTTGAACTAACCAATCAGTTCGCTTCTCGCTTCTGTTCGCGCGCTTCCG
 551 CTCTCCGAGCTCAATAAAAGAGCCCACAACCCCTCACTCGGCGCGCCAGT
 601 CTTCCGATAGACTGCGTCGCCCGGGTACCCGTATTCCCAATAAAGCCTCT
 651 TGCTGTTTGCATCCGAATCGTGGTCTCGCTGTTCCTTGGGAGGGTCTCCT
 701 CTGAGTGATTGACTACCCACGACGGGGGTCTTTCATTTGGGGGCTCGTCC
 751 GGGATTTGGAGACCCCTGCCCAGGGACCACCGACCCACCACCGGGAGGTA
 801 AGCTGGCCAGCAACTTATCTGTGTCTGTCCGATTGTCTAGTGTCTATGTT
 851 TGATGTTATGCGCCTGCGTCTGTACTAGTTAGCTAACTAGCTCTGTATCT
 901 GGCGGACCCGTGGTGGAACTGACGAGTTCTGAACACCCGGCCGCAACCCT
 951 GGGAGACGTCCCAGGGACTTTGGGGGCCGTTTTTGTGGCCCGACCTGAGG
1001 AAGGGAGTCGATGTGGAATCCGACCCCGTCAGGATATGTGGTTCTGGTAG
1051 GAGACGAGAACCTAAAACAGTTCCCGCCTCCGTCTGAATTTTTGCTTTCG
1101 GTTTGGAACCGAAGCCGCGCGTCTTGTCTGCTGCAGCGCTGCAGCATCGT
1151 TCTGTGTTGTCTCTGTCTGACTGTGTTTCTGTATTTGTCTGAAAATTAGG
1201 GCCAGACTGTTACCACTCCCTTAAGTTTGACCTTAGGTCACTGGAAAGAT
1251 GTCGAGCGGATCGCTCACAACCAGTCGGTAGATGTCAAGAAGAGACGTTG
1301 GGTTACCTTCTGCTCTGCAGAATGGCCAACCTTTAACGTCGGATGGCCGC
1351 GAGACGGCACCTTTAACCGAGACCTCATCACCCAGGTTAAGATCAAGGTC
1401 TTTTCACCTGGCCCGCATGGACACCCAGACCAGGTCCCCTACATCGTGAC
1451 CTGGGAAGCCTTGGCTTTTGACCCCCCTCCCTGGGTCAAGCCCTTTGTAC
1501 ACCCTAAGCCTCCGCCTCCTCTTCCTCCATCCGCCCCGTCTCTCCCCCTT
1551 GAACCTCCTCGTTCGACCCCGCCTCGATCCTCCCTTTATCCAGCCCTCAC
1601 TCCTTCTCTAGGCGCCGGAATTCCGATCTGATCAAGAGACAGGATGAGGG
1651 AGCTTGTATATCCATTTTCGGATCTGATCAGCACGTGTTGACAATTAATC
1701 ATCGGCATAGTATATCGGCATAGTATAATACGACAAGGTGAGGAACTAAA
1751 CCATGGCCAAGCCTTTGTCTCAAGAAGAATCCACCCTCATTGAAAGAGCA
1801 ACGGCTACAATCAACAGCATCCCCATCTCTGAAGACTACAGCGTCGCCAG
1851 CGCAGCTCTCTCTAGCGACGGCCGCATCTTCACTGGTGTCAATGTATATC
1901 ATTTTACTGGGGGACCTTGTGCAGAACTCGTGGTGCTGGGCACTGCTGCT
1951 GCTGCGGCAGCTGGCAACCTGACTTGTATCGTCGCGATCGGAAATGAGAA
2001 CAGGGGCATCTTGAGCCCCTGCGGACGGTGTCGACAGGTGCTTCTCGATC
2051 TGCATCCTGGGATCAAAGCGATAGTGAAGGACAGTGATGGACAGCCGACG
2101 GCAGTTGGGATTCGTGAATTGCTGCCCTCTGGTTATGTGTGGGAGGGCTA
2151 AGCACTTCGTGGCCGAGGAGCAGGACTGACACGTGCTACGAGATTTCGAT
2201 TCCACCGCCGCCTTCTATGAAAGGTTGGGCTTCGGAATCGTTTTCCGGGA
2251 CGCCGGCTGGATGATCCTCCAGCGCGGGGATCTCATGCTGGAGTTCTTCG
2301 CCCACCCCAACTTGTTTATTGCAGCTTATAATGGTTACAAATAAAGCAAT
2351 AGCATCACAAATTTCACAAATAAAGCATTTTTTTCACTGCATTCTAGTTG
2401 TGGTTTGTCCAAACTCATCAATGTATCTTATCATGTCTGTACGAGTTGGT
2451 TCAGCTGCTGCCTGAGGCTGGACGACCTCGCGGAGTTCTACCGGCAGTGC
2501 AAATCCGTCGGCATCCAGGAAACCAGCAGCGGCTATCCGCGCATCCATGC
2551 CCCCGAACTGCAGGAGTGGGGAGGCACGATGGCCGCTTTGGTCGAGGCGG
2601 ATCCGGCCATTAGCCATATTATTCATTGGTTATATAGCATAAATCAATAT
2651 TGGCTATTGGCCATTGCATACGTTGTATCCATATCATAATATGTACATTT
2701 ATATTGGCTCATGTCCAACATTACCGCCATGTTGACATTGATTATTGACT
2751 AGTTATTAATAGTAATCAATTACGGGGTCATTAGTTCATAGCCCATATAT
2801 GGAGTTCCGCGTTACATAACTTACGGTAAATGGCCCGCCTGGCTGACCGC
2851 CCAACGACCCCCGCCCATTGACGTCAATAATGACGTATGTTCCCATAGTA
```

Figure 17b

```
2901 ACGCCAATAGGGACTTTCCATTGACGTCAATGGGTGGAGTATTTACGGTA
2951 AACTGCCCACTTGGCAGTACATCAAGTGTATCATATGCCAAGTACGCCCC
3001 CTATTGACGTCAATGACGGTAAATGGCCCGCCTGGCATTATGCCCAGTAC
3051 ATGACCTTATGGGACTTTCCTACTTGGCAGTACATCTACGTATTAGTCAT
3101 CGCTATTACCATGGTGATGCGGTTTTGGCAGTACATCAATGGGCGTGGAT
3151 AGCGGTTTGACTCACGGGGATTTCCAAGTCTCCACCCCATTGACGTCAAT
3201 GGGAGTTTGTTTTGGCACCAAAATCAACGGGACTTTCCAAAATGTCGTAA
3251 CAACTCCGCCCCATTGACGCAAATGGGCGGTAGGCATGTACGGTGGGAGG
3301 TCTATATAAGCAGAGCTCGTTTAGTGAACCGTCAGATCGCCTGGAGACGC
3351 CATCCACGCTGTTTTGACCTCCATAGAAGACACCGGGACCGATCCAGCCT
3401 CCGCGGCCCCAAGCTTCTCGAGTTAACAGATCTAGGCTGGCACGACAGGT
3451 TTCCCGACTGGAAAGCGGGCAGTGAGCGCAACGCAATTAATGTGAGTTAG
3501 CTCACTCATTAGGCACCCCAGGCTTTACACTTTATGCTTCCGGCTCGTAT
3551 GTTGTGTGGAATTGTGAGCGGATAACAATTTCACACAGGAAACAGCTATG
3601 ACCATGATTACGCCAAGCTTGGCTGCAGGTCGACGGATCCACTAGTAACG
3651 GCCGCCAGTGTGCTGGAATTCACCATGGGGCAACCCGGGAACGGCAGCGC
3701 CTTCTTGCTGGCACCCAATGGAAGCCATGCGCCGGACCACGACGTCACGC
3751 AGCAAAGGGACGAGGTGTGGGTGGTGGGCATGGGCATCGTCATGTCTCTC
3801 ATCGTCCTGGCCATCGTGTTTGGCAATGTGCTGGTCATCACAGCCATTGC
3851 CAAGTTCGAGCGTCTGCAGACGGTCACCAACTACTTCATCACAAGCTTGG
3901 CCTGTGCTGATCTGGTCATGGGGCTAGCAGTGGTGCCCTTTGGGGCCGCC
3951 CATATTCTCATGAAAATGTGGACTTTTGGCAACTTCTGGTGCGAGTTCTG
4001 GACTTCCATTGATGTGCTGTGCGTCACGGCATCGATTGAGACCCTGTGCG
4051 TGATCGCAGTCGACCGCTACTTTGCCATTACTAGTCCTTTCAAGTACCAG
4101 AGCCTGCTGACCAAGAATAAGGCCCGGGTGATCATTCTGATGGTGTGGAT
4151 TGTGTCAGGCCTTACCTCCTTCTTGCCCATTCAGATGCACTGGTACAGGG
4201 CCACCCACCAGGAAGCCATCAACTGCTATGCCAATGAGACCTGCTGTGAC
4251 TTCTTCACGAACCAAGCCTATGCCATTGCCTCTTCCATCGTGTCCTTCTA
4301 CGTTCCCCTGGTGATCATGGTCTTCGTCTACTCCAGGGTCTTTCAGGAGG
4351 CCAAAAGGCAGCTCCAGAAGATTGACAAATCTGAGGGCCGCTTCCATGTC
4401 CAGAACCTTAGCCAGGTGGAGCAGGATGGGCGGACGGGGCATGGACTCCG
4451 CAGATCTTCCAAGTTCTGCTTGAAGGAGCACAAAGCCCTCAAGACGTTAG
4501 GCATCATCATGGGCACTTTCACCCTCTGCTGGCTGCCCTTCTTCATCGTT
4551 AACATTGTGCATGTGATCCAGGATAACCTCATCCGTAAGGAAGTTTACAT
4601 CCTCCTAAATTGGATAGGCTATGTCAATTCTGGTTTCAATCCCCTTATCT
4651 ACTGCCGGAGCCCAGATTTCAGGATTGCCTTCCAGGAGCTTCTGTGCCTG
4701 CGCAGGTCTTCTTTGAAGGCCTATGGCAATGGCTACTCCAGCAACGGCAA
4751 CACAGGGGAGCAGAGTGGATATCACGTGGAACAGGAGAAAGAAAATAAAC
4801 TGCTGTGTGAAGACCTCCCAGGCACGGAAGACTTTGTGGGCCATCAAGGT
4851 ACTGTGCCTAGCGATAACATTGATTCACAAGGGAGGAATTGTAGTACAAA
4901 TGACTCACTGCTCTCGAGAATCGAGGGGCGGCACCACCATCATCACCACG
4951 TCGACCCCGGGGACTACAAGGATGACGATGACAAGTAAGCTTTATCCATC
5001 ACACTGGCGGCCGCTCGAGCATGCATCTAGCGGCCGCTCGAGGCCGGCAA
5051 GGCCGGATCCCCGGGAATTCGCCCCTCTCCCTCCCCCCCCCCTAACGTTA
5101 CTGGCCGAAGCCGCTTGGAATAAGGCCGGTGTGCGTTTGTCTATATGTTA
5151 TTTTCCACCATATTGCCGTCTTTTGGCAATGTGAGGGCCCGGAAACCTGG
5201 CCCTGTCTTCTTGACGAGCATTCCTAGGGGTCTTTCCCTCTCGCCAAAG
5251 GAATGCAAGGTCTGTTGAATGTCGTGAAGGAAGCAGTTCCTCTGGAAGCT
5301 TCTTGAAGACAAACAACGTCTGTAGCGACCCTTTGCAGGCAGCGGAACCC
5351 CCCACCTGGCGACAGGTGCCTCTGCGGCCAAAAGCCACGTGTATAAGATA
5401 CACCTGCAAAGGCGGCACAACCCCAGTGCCACGTTGTGAGTTGGATAGTT
5451 GTGGAAAGAGTCAAATGGCTCTCCTCAAGCGTATTCAACAAGGGGCTGAA
5501 GGATGCCCAGAAGGTACCCCATTGTATGGGATCTGATCTGGGGCCTCGGT
5551 GCACATGCTTTACATGTGTTTAGTCGAGGTTAAAAAAACGTCTAGGCCCC
5601 CCGAACCACGGGGACGTGGTTTTCCTTTGAAAAACACGATGATAATATGG
5651 CCTCCTTTGTCTCTCTGCTCCTGGTAGGCATCCTATTCCATGCCACCCAG
5701 GCCGAGCTCACCCAGTCTCCAGACTCCCTGGCTGTGTCTCTGGGCGAGAG
5751 GGCCACCATCAACTGCAAGTCCAGCCAGAGTGTTTTGTACAGCTCCAACA
5801 ATAAGAACTATTTAGCTTGGTATCAGCAGAAACCAGGACAGCCTCCTAAG
5851 CTGCTCATTTACTGGGCATCTACCCGGGAATCCGGGGTCCCTGACCGATT
5901 CAGTGGCAGCGGGTCTGGGACAGATTTCACTCTCACCATCAGCAGCCTGC
5951 AGGCTGAAGATGTGGCAGTTTATTACTGTCAGCAATATTATAGTACTCAG
```

Figure 17c

```
6001 ACGTTCGGCCAAGGGACCAAGGTGGAAATCAAACGAACTGTGGCTGCACC
6051 ATCTGTCTTCATCTTCCCGCCATCTGATGAGCAGTTGAAATCTGGAACTG
6101 CCTCTGTTGTGTGCCTGCTGAATAACTTCTATCCCAGAGAGGCCAAAGTA
6151 CAGTGGAAGGTGGATAACGCCCTCCAATCGGGTAACTCCCAGGAGAGTGT
6201 CACAGAGCAGGACAGCAAGGACAGCACCTACAGCCTCAGCAGCACCCTGA
6251 CGCTGAGCAAAGCAGACTACGAGAAACACAAACTCTACGCCTGCGAAGTC
6301 ACCCATCAGGGCCTGAGATCGCCCGTCACAAAGAGCTTCAACAAGGGGAG
6351 AGTGTTAGTTCTAGATAATTAATTAGGAGGAGATCTCGAGCTCGCGAAAG
6401 CTTGGCACTGGCCGTCGTTTTACAACGTCGTGACTGGGAAAACCCTGGCG
6451 TTACCCAACTTAATCGCCTTGCAGCACATCCCCCTTTCGCCAGCCTCCTA
6501 GGTCGACATCGATAAAATAAAAGATTTTATTTAGTCTCCAGAAAAAGGGG
6551 GGAATGAAAGACCCCACCTGTAGGTTTGGCAAGCTAGCTTAAGTAACGCC
6601 ATTTTGCAAGGCATGGAAAAATACATAACTGAGAATAGAGAAGTTCAGAT
6651 CAAGGTCAGGAACAGATGGAACAGCTGAATATGGGCCAAACAGGATATCT
6701 GTGGTAAGCAGTTCCTGCCCCGGCTCAGGGCCAAGAACAGATGGAACAGC
6751 TGAATATGGGCCAAACAGGATATCTGTGGTAAGCAGTTCCTGCCCCGGCT
6801 CAGGGCCAAGAACAGATGGTCCCCAGATGCGGTCCAGCCCTCAGCAGTTT
6851 CTAGAGAACCATCAGATGTTTCCAGGGTGCCCCAAGGACCTGAAATGACC
6901 CTGTGCCTTATTTGAACTAACCAATCAGTTCGCTTCTCGCTTCTGTTCGC
6951 GCGCTTCTGCTCCCCGAGCTCAATAAAAGAGCCCACAACCCCTCACTCGG
7001 GGCGCCAGTCCTCCGATTGACTGAGTCGCCCGGGTACCCGTGTATCCAAT
7051 AAACCCTCTTGCAGTTGCATCCGACTTGTGGTCTCGCTGTTCCTTGGGAG
7101 GGTCTCCTCTGAGTGATTGACTACCCGTCAGCGGGGTCTTTCATTTGGG
7151 GGCTCGTCCGGGATCGGGAGACCCCTGCCCAGGGACCACCGACCCACCAC
7201 CGGGAGGTAAGCTGGCTGCCTCGCGCGTTTCGGTGATGACGGTGAAAACC
7251 TCTGACACATGCAGCTCCCGGAGACGGTCACAGCTTGTCTGTAAGCGGAT
7301 GCCGGGAGCAGACAAGCCCGTCAGGGCGCGTCAGCGGGTGTTGGCGGGTG
7351 TCGGGGCGCAGCCATGACCCAGTCACGTAGCGATAGCGGAGTGTATACTG
7401 GCTTAACTATGCGGCATCAGAGCAGATTGTACTGAGAGTGCACCATATGC
7451 GGTGTGAAATACCGCACAGATGCGTAAGGAGAAAATACCGCATCAGGCGC
7501 TCTTCCGCTTCCTCGCTCACTGACTCGCTGCGCTCGGTCGTTCGGCTGCG
7551 GCGAGCGGTATCAGCTCACTCAAAGGCGGTAATACGGTTATCCACAGAAT
7601 CAGGGGATAACGCAGGAAAGAACATGTGAGCAAAAGGCCAGCAAAAGGCC
7651 AGGAACCGTAAAAAGGCCGCGTTGCTGGCGTTTTTCCATAGGCTCCGCCC
7701 CCCTGACGAGCATCACAAAAATCGACGCTCAAGTCAGAGGTGGCGAAACC
7751 CGACAGGACTATAAAGATACCAGGCGTTTCCCCCTGGAAGCTCCCTCGTG
7801 CGCTCTCCTGTTCCGACCCTGCCGCTTACCGGATACCTGTCCGCCTTTCT
7851 CCCTTCGGGAAGCGTGGCGCTTTCTCATAGCTCACGCTGTAGGTATCTCA
7901 GTTCGGTGTAGGTCGTTCGCTCCAAGCTGGGCTGTGTGCACGAACCCCCC
7951 GTTCAGCCCGACCGCTGCGCCTTATCCGGTAACTATCGTCTTGAGTCCAA
8001 CCCGGTAAGACACGACTTATCGCCACTGGCAGCAGCCACTGGTAACAGGA
8051 TTAGCAGAGCGAGGTATGTAGGCGGTGCTACAGAGTTCTTGAAGTGGTGG
8101 CCTAACTACGGCTACACTAGAAGGACAGTATTTGGTATCTGCGCTCTGCT
8151 GAAGCCAGTTACCTTCGGAAAAAGAGTTGGTAGCTCTTGATCCGGCAAAC
8201 AAACCACCGCTGGTAGCGGTGGTTTTTTTGTTTGCAAGCAGCAGATTACG
8251 CGCAGAAAAAAGGATCTCAAGAAGATCCTTTGATCTTTTCTACGGGGTC
8301 TGACGCTCAGTGGAACGAAAACTCACGTTAAGGGATTTTGGTCATGAGAT
8351 TATCAAAAAGGATCTTCACCTAGATCCTTTTAAATTAAAAATGAAGTTTT
8401 AAATCAATCTAAAGTATATATGAGTAAACTTGGTCTGACAGTTACCAATG
8451 CTTAATCAGTGAGGCACCTATCTCAGCGATCTGTCTATTTCGTTCATCCA
8501 TAGTTGCCTGACTCCCCGTCGTGTAGATAACTACGATACGGGAGGGCTTA
8551 CCATCTGGCCCCAGTGCTGCAATGATACCGCGAGACCCACGCTCACCGGC
8601 TCCAGATTTATCAGCAATAAACCAGCCAGCCGGAAGGGCCGAGCGCAGAA
8651 GTGGTCCTGCAACTTTATCCGCCTCCATCCAGTCTATTAATTGTTGCCGG
8701 GAAGCTAGAGTAAGTAGTTCGCCAGTTAATAGTTTGCGCAACGTTGTTGC
8751 CATTGCTGCAGGCATCGTGGTGTCACGCTCGTCGTTTGGTATGGCTTCAT
8801 TCAGCTCCGGTTCCCAACGATCAAGGCGAGTTACATGATCCCCCATGTTG
8851 TGCAAAAAAGCGGTTAGCTCCTTCGGTCCTCCGATCGTTGTCAGAAGTAA
8901 GTTGGCCGCAGTGTTATCACTCATGGTTATGGCAGCACTGCATAATTCTC
8951 TTACTGTCATGCCATCCGTAAGATGCTTTTCTGTGACTGGTGAGTACTCA
9001 ACCAAGTCATTCTGAGAATAGTGTATGCGGCGACCGAGTTGCTCTTGCCC
9051 GGCGTCAACACGGGATAATACCGCGCCACATAGCAGAACTTTAAAAGTGC
```

Figure 17d

```
9101  TCATCATTGGAAAACGTTCTTCGGGGCGAAAACTCTCAAGGATCTTACCG
9151  CTGTTGAGATCCAGTTCGATGTAACCCACTCGTGCACCCAACTGATCTTC
9201  AGCATCTTTTACTTTCACCAGCGTTTCTGGGTGAGCAAAAACAGGAAGGC
9251  AAAATGCCGCAAAAAAGGGAATAAGGGCGACACGGAAATGTTGAATACTC
9301  ATACTCTTCCTTTTTCAATATTATTGAAGCATTTATCAGGGTTATTGTCT
9351  CATGAGCGGATACATATTTGAATGTATTTAGAAAAATAAACAAATAGGGG
9401  TTCCGCGCACATTTCCCCGAAAAGTGCCACCTGACGTCTAAGAAACCATT
9451  ATTATCATGACATTAACCTATAAAAATAGGCGTATCACGAGGCCCTTTCG
   1. TCTTCAAGAAT
```

```
Features:
149-737     Moloney murine sarcoma virus 5' LTR
807-1616    Extended Packaging Region
1680-1735   EM7 promoter (bacteriophage T7 promoter)
1754-2151   Blasticidin resistance gene coding sequence
2310-2440   SV40 poly A signal and site
2603-3420   CMV IE promoter
3675-4988   G-protein-coupled receptor (GPCR)
5071-5646   IRES
5647-5703   Bovine a-lactalbumin signal peptide
5704-6372   'humanized' antibody light chain
6553-7146   MoMuLV 3' LTR
7683Origin  of replication
9302-8442   b-Lactmase coding sequence
```

US 7,378,273 B2

EXPRESSION VECTORS

This application is a continuation of U.S. application Ser. No. 09/897,006, filed Jun. 29, 2001, which claims the benefit of Provisional Appl. 60/215,851, filed 3 Jul. 2000.

FIELD OF THE INVENTION

The present invention relates to novel regulatory elements and vectors for the expression of one or more proteins in a host cell.

BACKGROUND OF THE INVENTION

Methods for expression of recombinant proteins in bacterial host are widespread and offer ease of use and purification of the recombinant product. However, use of these systems for the expression of eukaryotic proteins is often limited by problems of insolubility and lack of proper post-transcription and post-translational processing (see, e.g., U.S. Pat. No. 5,721,121, incorporated herein by reference). Thus, eukaryotic expression systems are generally used for the expression of eukaryotic proteins. In particular, the pharmaceutical biotechnology industry relies heavily on the production of recombinant proteins in mammalian cells. These recombinantly produced proteins are essential to the therapeutic treatment of many diseases and conditions. In many cases, the market for these proteins exceeds a billion dollars a year. Examples of proteins produced recombinantly in mammalian cells include erythropoietin, factor VIII, factor IX, and insulin. In addition, recombinant antibodies are often used as therapeutic agents. Clinical applications of recombinantly produced proteins, in particular antibodies, often require large amounts of highly purified proteins. Proteins are generally produced in either mammalian cell culture or in transgenic animals.

Vectors for transferring the gene of interest into mammalian cells are widely available, including plasmids, retroviral vectors, and adenoviral vectors. Retroviral vectors are widely used as vehicles for delivery of genes into mammalian cells (See e.g., Vile and Russell, British Medical Bulletin, 51:12 [1995]). However, current methods for creating mammalian cell lines for expression of recombinant proteins suffer from several drawbacks. (See, e.g., Mielke et al., Biochem. 35:2239-52 [1996]). Episomal systems allow for high expression levels of the recombinant protein, but are frequently only stable for a short time period (See, e.g., Klehr and Bode, Mol. Genet. (Life Sci. Adv.) 7:47-52 [1988]). Mammalian cell lines containing integrated exogenous genes are somewhat more stable, but there is increasing evidence that stability depends on the presence of only a few copies or even a single copy of the exogenous gene. Vectors are often unstable, resulting in a decrease in the level of protein expression over time.

Based on overall product yield, expression of recombinant proteins in animals results in higher yields, relative to expression in cell culture (See e.g., Werner et al., Arzneimittelforshcung, 48:870 [1998]; Pollock et al., J. Immunol. Methods, 231:147 [1999]). However, expression in transgenic animals is limited by methods of producing transgenic mammals, variation in production and purity, and the life span of the animal.

Thus, despite continued efforts in the field, vectors for high level, continuous expression of one or more proteins in a host cell remain needed in the art.

SUMMARY OF THE INVENTION

The present invention relates to novel regulatory elements and vectors for the expression of one or more proteins in a host cell.

In some embodiments, the present invention provides a hybrid α-lactalbumin promoter comprising at least one portion derived from a first mammalian α-lactalbumin promoter and at least one portion derived from a second mammalian α-lactalbumin promoter. The present invention is not limited to portions derived from any particular α-lactalbumin promoter. Indeed, portions from a variety of α-lactalbumin promoters are contemplated, including, but not limited to bovine, human, ovine, caprine, and murine α-lactalbumin promoters. In other embodiments, the present invention provides a nucleic acid comprising a nucleic acid sequence selected from the group consisting of SEQ ID NO:1 and sequences hybridizable to SEQ ID NO:1 under low stringency conditions, wherein the nucleic acid contains sequences derived from at least two mammalian sources and causes mammary specific gene expression. In still other embodiments, the present invention provides a nucleic acid sequence encoding a hybrid bovine/human alpha lactalbumin (αLA) promoter/enhancer (i.e., SEQ ID NO:1) and sequences that are hybridizable to a hybrid bovine/human α-LA promoter under low to high stringency conditions. In preferred embodiments, these sequences drive the expression of an exogenous gene in the mammary gland of a transgenic animal. In some embodiments, the hybridizable sequence comprises human and bovine elements. In other embodiments, the present invention provides a vector containing the nucleic acid sequence of hybrid bovine/human α-LA promoter. In some embodiments, the vector is a retroviral vector. In still further embodiments, the present invention provides a host cell containing a vector containing a hybrid bovine/human α-LA promoter.

The present invention also provides a nucleic acid encoding a mutant RNA export element (PPE element; SEQ ID NO:2) and sequences that are hybridizable to a mutant PPE element. In some embodiments, the sequences hybridizable to a mutant PPE element contain ATG sequences that have been mutated at at least one of the positions corresponding to nucleic acid residues 4, 112, 131, and 238 of the wild-type PPE element. In preferred embodiments, these sequences enhance the export from the nucleus of the RNA to which they are operably linked. In other embodiments, the present invention provides a vector containing the nucleic acid sequence of the mutant PPE element. In some embodiments, the vector is a retroviral vector. In still further embodiments, the present invention provides a host cell containing a vector that contains a mutant PPE element.

The present invention also provides a nucleic acid encoding an IRES coding sequence and a signal peptide coding sequence, wherein said IRES and signal peptide coding sequences are adjacent to one another. In some embodiments, the IRES/signal peptide sequence comprises SEQ ID NO:3 or SEQ ID NO:12 and sequences that are hybridizable to these sequences under low stringency conditions. In preferred embodiments, these sequences interact with a ribosome and provide for the secretion of proteins to which they are operably linked. The present invention is not limited to any particular signal sequence peptide. Indeed, it is contemplated that a variety of signal peptides find use in the present invention. In some embodiments, the signal peptide sequence is selected from alpha-casein, human growth hormone, or α-lactalbumin signal peptide sequences. In other embodiments, the present invention provides a vector containing the nucleic acid sequence of the IRES/signal peptide sequence. In some embodiments, the vector is a retroviral vector. In still further embodiments, the present invention provides a host cell containing a vector that contains a IRES/signal peptide sequence.

The present invention also provides methods for producing a protein of interest. In some embodiments, the methods comprise providing a host cell and a vector containing at least one exogenous gene operably linked to a bovine/human hybrid α-lactalbumin promoter and introducing the vector to the host cell under conditions such that expression of the protein encoded by the exogenous gene is expressed. In some embodiments, the vector further contains a mutant RNA export element. In other embodiments, the vector contains at least two exogenous genes. In still further embodiments, the two or more exogenous genes are arranged in a polycistronic sequence separated by an internal ribosome entry site/bovine α-lactalbumin signal peptide.

The present invention also provides methods for expressing at least two proteins in a polycistronic sequence. In some embodiments, the proteins are unrelated, while in other embodiments, the proteins are subunits of a multisubunit protein. In some preferred embodiments, the present invention provides methods for producing an immunoglobulin including providing a host cell and a vector comprising a first exogenous gene and a second exogenous gene, wherein the first exogenous gene encodes a first immunoglobulin chain and wherein the second exogenous gene encodes a second immunoglobulin chain, and wherein the first and the second genes are separated by an internal ribosome entry site, and introducing the vector to the host cell under conditions such the first immunoglobulin chain and the second immunoglobulin chain encoded by the first and second exogenous genes are expressed. In some embodiments, the first immunoglobulin chain is an immunoglobulin light chain (e.g., λ or κ) and the second immunoglobulin chain is an immunoglobulin heavy chain (e.g., γ, α, μ, δ, or ε). In other embodiments, the first immunoglobulin chain is an immunoglobulin heavy chain (e.g., γ, α, μ, δ, or ε) and the second immunoglobulin chain is an immunoglobulin light chain (e.g., λ or κ). In some embodiments, the vector is a retroviral vector. In other embodiments, the vector further contains a bovine α-lactalbumin signal peptide. In still further embodiments, the vector further contains a bovine/human hybrid α-lactalbumin promoter. In yet other embodiments, the first immunoglobulin chain and the second immunoglobulin chain are expressed at a ratio of about 0.9:1.1 to 1:1. The present invention also provides immunoglobulins produced by the methods described herein. The present invention is not limited to the use of any particular vector. Indeed, it is contemplated that a variety of vectors find use in the present invention, including, but not limited to plasmid and retroviral vectors. In some preferred embodiments, the retroviral vector is pseudotyped.

In still further embodiments, the present invention provides methods of indirectly detecting the expression of a protein of interest comprising providing a host cell transduced or transfected with a vector encoding a polycistronic sequence, wherein the polycistronic sequence comprises a signal protein and a protein of interest operably linked by an IRES, and culturing the host cells under conditions such that the signal protein and protein of interest are produced, wherein the presence of the signal protein indicates the presence of the protein of interest. The methods of the present invention are not limited to the expression of any particular protein of interest. Indeed, the expression of a variety of proteins of interest is contemplated, including, but not limited to, G-protein coupled receptors. The present invention is not limited to the use of any particular signal protein. Indeed, the use of variety of signal proteins is contemplated, including, but not limited to, immunoglobulin heavy and light chains, beta-galactosidase, beta-lactamase, green fluorescent protein, and luciferase. In particularly preferred embodiments, expression of the signal protein and protein of interest is driven by the same promoter and the signal protein and protein of interest are transcribed as a single transcriptional unit.

DESCRIPTION OF THE FIGURES

FIG. 4 provides the sequence for the hybrid human-bovine alpha-lactalbumin promoter (SEQ ID NO:1).

FIG. 5 provides the sequence for the mutated PPE sequence (SEQ ID NO:2).

FIG. 6 provides the sequence for the IRES-Signal peptide sequence (SEQ ID NO:3).

FIGS. 7a and 7b provide the sequence for CMV MN14 vector (SEQ ID NO:4).

FIGS. 8a and 8b provide the sequence for the CMV LL2 vector (SEQ ID NO:5).

FIGS. 9a-c provide the sequence for the MMTV MN14 vector (SEQ ID NO:6).

FIGS. 10a-d provide the sequence for the alpha-lactalbumin MN14 Vector (SEQ ID NO:7).

FIGS. 11a-c provide the sequence for the alpha-lactalbumin Bot vector (SEQ ID NO:8).

FIGS. 12a-b provide the sequence for the LSRNL vector (SEQ ID NO:9).

FIGS. 13a-b provide the sequence for the alpha-lactalbumin cc49IL2 vector (SEQ ID NO:10).

FIGS. 14a-c provides the sequence for the alpha-lactalbumin YP vector (SEQ ID NO:11).

FIG. 15 provides the sequence for the IRES-Casein signal peptide sequence (SEQ ID NO:12).

FIGS. 16a-c provide the sequence for the LNBOTDC vector (SEQ ID NO:13).

FIGS. 17a-d provide the sequence of a retroviral vector that expresses a G-Protein coupled receptor and antibody light chain.

DEFINITIONS

Figure 1:
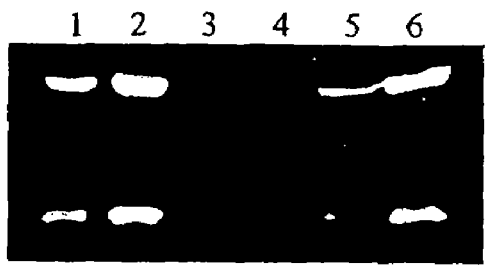
FIG. 1 is a Western blot of a 15% SDS-PAGE gel run under denaturing conditions and probed with anti-human IgG (Fc) and anti-human IgG (kappa).
Figure 2:
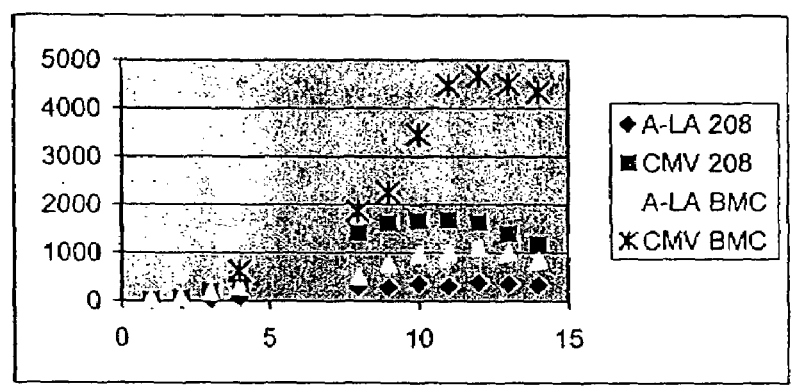
FIG. 2 is a graph of MN14 expression over time.

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transpose, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrating vector" refers to a vector whose integration or insertion into a nucleic acid (e.g., a chromosome) is accomplished via an integrase. Examples of "integrating vectors" include, but are not limited to, retroviral vectors, transposons, and adeno associated virus vectors.

As used herein, the term "integrated" refers to a vector that is stably inserted into the genome (i.e., into a chromosome) of a host cell.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "signal protein" refers to a protein that is co-expressed with a protein of interest and which, when detected by a suitable assay, provides indirect evidence of expression of the protein of interest. Examples of signal protein useful in the present invention include, but are not limited to, immunoglobulin heavy and light chains, beta-galactosidase, beta-lactamase, green fluorescent protein, and luciferase.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in Nucleic Acid Hybridization[1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp.16.9-16.15.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the *Rous sarcoma* virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element which is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin)

by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one which is capable of directing a level of transcription of an operably linked nucleic acid sequence in the presence of a stimulus (e.g., heat shock, chemicals, etc.) which is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual*, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons " or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the term "secretion signal" refers to any DNA sequence which when operably linked to a recombinant DNA sequence encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973-77 [1980], Gray et al., Gene 39(2): 247-54 [1985], and Martial et al., Science 205: 602-607 [1979]). Such secretion signal sequences are preferably derived from genes encoding polypeptides secreted from the cell type targeted for tissue-specific expression (e.g., secreted milk proteins for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310 and U.S. Pat. No. 6,136,597, each of which is incorporated herein by reference).

As used herein, the term "polycistronic" refers to an mRNA encoding more than polypeptide chain (See, e.g., WO 93/03143, WO 88/05486, and European Pat. No. 117058, all of which are incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3'LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMOLV), Moloney murine sarcoma virus (MoMSV), and Mouse mammary tumor virus (MMTV), Spumavirinae, amd Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola) which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus which is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus which includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein, the term "transpose" refers to transposable elements (e.g., Tn5, Tn7, and Tn10) that can move or transpose from one position to another in a genome. In general, the transposition is controlled by a transposase. The term "transpose vector," as used herein, refers to a vector encoding a nucleic acid of interest flanked by the terminal ends of transpose. Examples of transpose vectors include, but are not limited to, those described in U.S. Pat. Nos. 6,027,722; 5,958,775; 5,968,785; 5,965,443; and 5,719,055, all of which are incorporated herein by reference.

As used herein, the term "adeno-associated virus (AAV) vector" refers to a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV vector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements which allow for the induction of transcription. Such control elements are described above.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the antisense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein coat) a heterologous nucleotide sequence, which in turn is flanked 5' and 3' by AAV ITRs. A number of techniques for constructing recombinant AAV virions are known in the art (See, e.g., U.S. Pat. No. 5,173,414; WO 92/01070; WO 93/03769; Lebkowski et al., Molec. Cell. Biol. 8:3988-3996 [1988]; Vincent et al., Vaccines 90 [1990] (Cold Spring Harbor Laboratory Press); Carter, Current Opinion in Biotechnology 3:533-539 [1992]; Muzyczka, Current Topics in Microbiol. and Immunol. 158:97-129 [1992]; Kotin, Human Gene Therapy 5:793-801 [1994]; Shelling and Smith, Gene Therapy 1:165-169 [1994]; and Zhou et al., J. Exp. Med. 179:1867-1875 [1994], all of which are incorportaed herein by reference).

Suitable nucleotide sequences for use in AAV vectors (and, indeed, any of the vectors described herein) include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. (See, e.g., Han et al., Proc. Natl. Acad. Sci. USA 88:4313-4317 [1991]; Uhlmann et al., Chem. Rev. 90:543-584 [1990]; Helene et al., Biochim. Biophys. Acta. 1049:99-125 [1990]; Agarwal et al., Proc. Natl. Acad. Sci. USA 85:7079-7083 [1989]; and Heikkila et al., Nature 328:445-449 [1987]). For a discussion of suitable ribozymes, see, e.g., Cech et al. (1992) J. Biol. Chem. 267:17479-17482 and U.S. Pat. No. 5,225,347, incorporated herein by reference.

By "adeno-associated virus inverted terminal repeats" or "AAV ITRs" is meant the art-recognized palindromic regions found at each end of the AAV genome which function together in cis as origins of DNA replication and as packaging signals for the virus. For use with the present invention, flanking AAV ITRs are positioned 5' and 3' of one or more selected heterologous nucleotide sequences and, together with the rep coding region or the Rep expression product, provide for the integration of the selected sequences into the genome of a target cell.

The nucleotide sequences of AAV ITR regions are known (See, e.g., Kotin, Human Gene Therapy 5:793-801 [1994]; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. The 5' and 3' ITRs which flank a selected heterologous nucleotide sequence need not necessarily be identical or derived from the same AAV serotype or isolate, so long as they function as intended, i.e., to allow for the integration of the associated heterologous sequence into the target cell genome when the rep gene is present (either on the same or on a different vector), or when the Rep expression product is present in the target cell.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "clonally derived" refers to a cell line that it derived from a single cell.

As used herein, the term "non-clonally derived" refers to a cell line that is derived from more than one cell.

As used herein, the term "passage" refers to the process of diluting a culture of cells that has grown to a particular density or confluency (e.g., 70% or 80% confluent), and then allowing the diluted cells to regrow to the particular density or confluency desired (e.g., by replating the cells or establishing a new roller bottle culture with the cells.

As used herein, the term "stable," when used in reference to genome, refers to the stable maintenance of the information content of the genome from one generation to the next, or, in the particular case of a cell line, from one passage to the next. Accordingly, a genome is considered to be stable if no gross changes occur in the genome (e.g., a gene is deleted or a chromosomal translocation occurs). The term "stable" does not exclude subtle changes that may occur to the genome such as point mutations.

As used herein, the term "response," when used in reference to an assay, refers to the generation of a detectable signal (e.g., accumulation of reporter protein, increase in ion concentration, accumulation of a detectable chemical product).

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases are the tyrosine kinases (TKs) which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity (See, e.g., Ullrich and Schlessinger, Cell 61:203-212 [1990]). Tyrosine kinases can also be cytoplasmic, non-receptor-type enzymes and act as a downstream component of a signal transduction pathway.

As used herein, the term "signal transduction protein" refers to a proteins that are activated or otherwise effected by ligand binding to a membrane receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249-257 [1995]). Typically, GPCRs contain seven transmembrane domains. Putative GPCRs can be identified on the basis of sequence homology to known GPCRs.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydrolyses GTP, and a dimeric βγ subunit. In the basal, inactive state, the G-protein exists as a heterotrimer of the α and βγ subunits. When the G-protein is inactive, guanosine diphosphate (GDP) is associated with the α subunit of the G-protein. When a GPCR is bound and activated by a ligand, the GPCR binds to the G-protein heterotrimer and decreases the affinity of the Gα subunit for GDP. In its active state, the G subunit exchanges GDP for guanine triphosphate (GTP) and active Gα subunit disassociates from both the receptor and the dimeric βγ subunit. The disassociated, active Gα subunit transduces signals to effectors that are "downstream" in the G-protein signalling pathway within the cell. Eventually, the G-protein's endogenous GTPase activity returns active G subunit to its inactive state, in which it is associated with GDP and the dimeric βγ subunit.

Numerous members of the heterotrimeric G-protein family have been cloned, including more than 20 genes encoding various Gα subunits. The various G subunits have been categorized into four families, on the basis of amino acid sequences and functional homology. These four families are termed $G\alpha_s$, $G\alpha_i$, $G\alpha_q$, and $G\alpha_{12}$. Functionally, these four families differ with respect to the intracellular signaling pathways that they activate and the GPCR to which they couple.

For example, certain GPCRs normally couple with $G\alpha_s$ and, through $G\alpha_s$, these GPCRs stimulate adenylyl cyclase activity. Other GPCRs normally couple with $GG\alpha_q$, and through $GG\alpha_q$, these GPCRs can activate phospholipase C (PLC), such as the β isoform of phospholipase C (i.e., PLCβ, Sternweis and Smrcka, Trends in Biochem. Sci. 17:502-506 [1992]).

As used herein, the term "immunoglobulin" refers to proteins which bind a specific antigen. Immunoglobulins include, but are not limited to, polyclonal, monoclonal, chimeric, and humanized antibodies, Fab fragments, F(ab')2 fragments, and includes immunoglobulins of the following classes: IgG, IgA, IgM, IgD, IbE, and secreted immunoglobulins (sIg). Immunoglobulins generally comprise two identical heavy chains (γ, α, μ, γ, or ε) and two light chains (κ or λ).

As used herein, the term "antigen binding protein" refers to proteins which bind to a specific antigen. "Antigen binding proteins" include, but are not limited to, immunoglobulins, including polyclonal, monoclonal, chimeric, and humanized antibodies; Fab fragments, F(ab')2 fragments, and Fab expression libraries; and single chain antibodies. Various procedures known in the art are used for the production of polyclonal antibodies. For the production of an antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include, but are not limited to, the hybridoma technique originally developed by Köhler and Milstein (Köhler and Milstein, Nature 256:495-497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (Huse et al., Science 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos.,6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

DETAILED DESCRIPTION OF THE INVENTION

The present invention provides novel regulatory sequences for use in expression vectors. In some embodiments, the present invention provides retroviral expression vectors containing novel regulatory elements. In addition, in still other embodiments, the present invention provides methods for expressing proteins of interest in host cells. In particularly preferred embodiments, the present invention provides methods for expressing two chains of a multisubunit protein (e.g., a heavy chain and a light chain of an immunoglobulin or the subunits of follicle stimulating hormone) in a nearly equal ratio. These methods take advantage of the novel regulatory sequences and vectors of the present invention to solve problems in the prior art.

I. Components of Retroviral Expression Vectors

In particularly preferred embodiments, the retroviral vectors of the present invention include the following elements in operable association: a) a 5' LTR; b) a packaging signal; c) a 3' LTR, and d) a nucleic acid encoding a protein of interest located between the 5' and 3' LTRs. In addition, in some preferred embodiments, novel compositions, including, but not limited to those described below are included in expression vectors in order to aid in the expression, secretion and purification of proteins of interest. The following novel elements are described in more detail below: bovine/human hybrid alpha-lactalbumin (α-LA) promoter (A); mutant RNA export element (B); and internal ribosome entry site (C).

A. Bovine/Human Hybrid Alpha Lactalbumin Promoter

In some embodiments, the present invention provides a hybrid α-lactalbumin (α-LA) promoter. It is contemplated that the hybrid promoter may be constructed from portions of any two or more mammalian α-lactalbumin promoters (e.g., human, bovine, goat, sheep, rabbit, or mouse α-lactalbumin promoters among others; see, e.g., GenBank Accession numbers AF124257; AF123893; AX067504; Soulier et al., Transgenic Res. 8(1):23-31 (1999); McKee et al., Nat. Biotech. 16(7):647-51 (1998); Lubon et al., Biochem. J. 256(2):391-6 (1988); and U.S. Pat. No. 5,530,177). In some embodiments, the portion of at least one of the promoters contributing to the hybrid is at least 50 nucleotides in length, while in preferred embodiments, the portion of at least one of the promoters contributing to the hybrid is at least 100 nucleotides in length, while in particularly preferred embodiments, the portion of at least one of the promoters contributing to the hybrid is at least 500 nucleotides length, with the portion of the at least one other promoter contributing to the hybrid being of similar or longer length. Once constructed, the hybrid promoters can be assayed for functionality by operably linking the promoter to a reporter gene such as beta-galactosidase, green fluorescent protein, or luciferase, creating a transgenic animal such as transgenic mouse or bovine that comprises the resulting construct, and assaying various tissues of the resulting transgenic animal to determine the specificity of expression from the hybrid promoter. In preferred embodiments, expression from the hybrid promoter is substantially specific to the mammary gland, and in particular to mammary epithelial cells, with no or only trace levels of expression of in other tissues.

In particularly preferred embodiments, the hybrid promoter is a bovine/human hybrid α-lactalbumin (α-LA) promoter (SEQ ID NO: 1). The human portion of the promoter was derived from human genomic DNA and contains bases from +15 relative to the transcription start point to −600 relative to the transcription start point. The bovine portion is attached to the end of the human portion and corresponds to bases −550 to −2000 relative to the transcription start point.

The hybrid promoter preferably used in the present invention utilizes a region of the human promoter that contained an internal poly-adenylation signal. The internal poly-adenylation signal was removed by mutation. The mutation was at base 2012 and involved a change from A to T. The present invention is not limited to any particular mechanism of action. Indeed, an understanding of the mechanism is not required to practice the present invention. Nevertheless, it is contemplated the removal of poly-adenylation signals improves retroviral RNA production by eliminating premature mRNA termination problems. In addition, it is contemplated that additional enhancer regions exist in the human, but not the bovine sequence. The hybrid promoter was constructed to take advantage of these additional sequences. Likewise, the hybrid promoter contains bovine elements that may or may not be found in the human promoter.

B. RNA Export Element

In some embodiments, the present invention comprises a mutant RNA export element (pre-mRNA processing element (PPE), Mertz sequence, or WPRE; See, e.g., U.S. Pat. Nos. 5,914,267 and 5,686,120 and PCT Publication WO99/14310, all of which are incorporated herein by reference). The present invention is not limited to any particular mechanism of action. Indeed, an understanding of the mechanism is not required to practice the present invention. Nevertheless, it is contemplated that the use of RNA export elements allows or facilitates high levels of expression of the protein of interest without incorporating splice signals or introns in the nucleic acid sequence encoding the protein of interest.

In some embodiments, a mutated PPE element is utilized. In some particularly preferred embodiments, the PPE sequence is mutated to remove internal ATG sequences. The present invention is not limited to any particular mechanism of action. Indeed, an understanding of the mechanism is not required to practice the present invention. Nevertheless, it is contemplated that the removal of internal start sequences prevents potential unwanted translation initiation. In some embodiments utilizing a mutated PPE sequence, bases 4, 112, 131, and 238 of SEQ ID NO: 2 were changed from a G to a T. In all cases, these changes resulted in and ATG start codon being mutated to an ATT codon. In some embodiments, the mutated PPE sequence is placed in the 5' untranslated region (UTR) of the mRNA encoding the gene of interest. In other embodiments, the mutated PPE sequence is placed in the 3' UTR of the mRNA encoding the gene of interest. In some preferred embodiments, two mutated PPE sequences separated by a linker are placed in a head to tail array (See e.g., SEQ ID NO:2). It has been shown that two copies of the sequence cause a more dramatic effect on mRNA export. In other embodiments, 2-20 copies of the mutated PPE sequence are placed in the mRNA encoding the gene of interest.

Functional variants of the above sequences are easily identified by operably linking the variant sequence to a test gene in a vector, transfecting a host cell with the vector, and analyzing the host cell for expression of the test gene. Suitable test genes, host cells, and vectors are disclosed in the examples.

C. Internal Ribosome Entry Site

In some embodiments, the present invention comprises an internal ribosome entry site (IRES)/signal peptide sequence (e.g., SEQ ID NOs:3 and 12). The present invention contemplates that a variety of signal sequences may be fused with a variety of IRES sequences. Suitable signal sequences include those from α-lactalbumin, casein, tissue plasminogen activator, serum albumin, lactoferrin, and lactoferrin (See, e.g., Zwizinski et al., J. Biol. Chem. 255(16): 7973-77 [1980], Gray et al., Gene 39(2): 247-54 [1985], and Martial et al., Science 205: 602-607 [1979]). Such secretion signal sequences are preferably derived from genes encoding polypeptides secreted from the cell type targeted for tissue-specific expression (e.g., secreted milk proteins for expression in and secretion from mammary secretory cells). Suitable IRES sequences include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Functional IRES/signal peptide sequences may be identified by operably linking two genes with the sequence and an appropriate promoter, transfecting a host cell with the construct, and assaying the host cell for production the proteins encoding by the two genes. Suitable genes, vector constructs, and host cells for such screening are provided in the examples. In preferred embodiments, the coding sequences for the IRES and signal peptide are adjacent to one another, with no intervening coding sequences (i.e., that may be separated by noncoding sequences in some instances).

The present invention is not limited to any particular mechanism of action. Indeed, an understanding of the mechanism is not required to practice the present invention. The IRES allows translation of the gene to start at the IRES sequence, thereby resulting in the expression of two genes of interest in the same construct. The bovine α-lactalbumin signal peptide or casein signal peptide causes extracellular secretion of expressed protein products.

In some embodiments, the initial ATG of the signal peptide is attached to the IRES in order to allow the most efficient translation initiation from the IRES. In some embodiments, the second codon of the signal peptide is mutated from an ATG to a GCC, changing the second amino acid of the α-lactalbumin signal peptide from a methionine to an alanine. The present invention is not limited to any particular mechanism of action. Indeed, an understanding of the mechanism is not required to practice the present invention. Nevertheless, it is contemplated that this mutation facilitates more efficient translation initiation by the IRES. In some embodiments, the (IRES)/signal peptide is inserted into a vector between two genes of interest. In these embodiments, the (IRES)/signal peptide creates a second translation initiation site, allowing for the expression of two polypeptides from the same expression vector. In other words, a single transcript is produced that encodes two different polypeptides (e.g., the heavy and light chains of an immunoglobulin).

In some embodiments, the signal peptide is derived from α-lactalbumin. In other embodiments, the present invention comprises an internal ribosome entry site (IRES)/modified bovine α-S1 Casein signal peptide fusion protein (SEQ ID NO:12). The present invention is not limited to any particular mechanism of action. Indeed, an understanding of the mechanism is not required to practice the present invention. The IRES allows translation of the gene to start at the IRES sequence, allowing the expression of two genes of interest in the same construct. The bovine α-S1 casein signal peptide causes secretion of expressed protein products.

In some embodiments the second codon of the bovine α-S1 casein signal peptide is mutated from a AAA to a GCC. The mutation results in the second codon of the signal peptide being changed from an alanine to a lysine. In some embodiments, the third codon of the signal peptide is mutated from a CTT to a TTG, a change which does not result and an amino acid substitution. The present invention is not limited to any particular mechanism of action. Indeed, an understanding of the mechanism is not required to practice the present invention. Nevertheless, it is contemplated that this mutation allows more efficient translation initiation by the IRES.

II. Retroviral Expression Vectors

In some embodiments, the present invention comprises retroviral expression vectors. Retroviruses (family Retroviridae) are generally divided into three groups: the spumaviruses (e.g., human foamy virus); the lentiviruses (e.g., human immunodeficiency virus and sheep visna virus), and the oncoviruses (e.g., MLV and Rous sarcoma virus).

Retroviruses are enveloped (i.e., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (containing the viral gag gene products) which is surrounded by a lipid bilayer membrane derived from the host cell containing the viral envelope glycoproteins (also referred to as membrane-associated proteins).

The genomic organization of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector which contains the sequences necessary for the efficient expression of the gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (−PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes which are essential for viral replication (these essential genes are either deleted or disabled); therefore, the resulting virus is said to be "replication defective".

Second, following the construction of the recombinant vector, the vector DNA is introduced into a packaging cell line. Packaging cell lines provide viral proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles lacking a membrane-associated protein (e.g., an env protein). In order to produce viral particles containing a membrane associated protein which will permit entry of the virus into a cell, the packaging cell line containing the retroviral sequences is commonly transfected with sequences encoding a membrane-associated protein (e.g., the G protein of vesicular stomatitis virus (VSV)). The transfected packaging cell will then produce viral particles which contain the membrane-associated protein expressed by the transfected packaging cell line; these viral particles which contain viral genomic RNA derived from one virus encapsidated by the envelope proteins of another virus are said to be "pseudotyped virus particles".

The retroviral vectors of the present invention can be further modified to include additional regulatory sequences. As described above, the retroviral vectors of the present invention include the following elements in operable association: a) a 5' LTR; b) a packaging signal; c) a 3' LTR; and d) a nucleic acid encoding a protein of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter, and the thymidine kinase promoter.

In other embodiments of the present invention, where secretion of the protein of interest is desired, the vectors are modified by including a signal peptide sequence in operable association with the protein of interest. The sequences of several suitable signal peptides are known in the art, including, but not limited to, those derived from tissue plasminogen activator, human growth hormone, lactoferrin, alpha S1-casein, and alpha-lactalbumin.

In other embodiments of the present invention, the vectors are modified by incorporating one or more of the elements described above, including, but not limited to, an RNA export element, a PPE element, and an IRES/bovine α-lactalbumin signal sequence.

The retroviral vectors of the present invention may further comprise a selectable marker which facilitates selection of transformed cells. A number of selectable markers known in the art find use in the present invention, including, but not limited to the bacterial aminoglycoside 3' phosphotransferase gene (also referred to as the "neo gene") that confers resistance to the drug G418 in mammalian cells, the bacterial hygromycin G phosphotransferase (hyg) gene that confers resistance to the antibiotic hygromycin, and the bacterial xanthine-guanine phosphoribosyl transferase gene (also referred to as the "gpt gene") that confers the ability to grow in the presence of mycophenolic acid. In some embodiments, the selectable marker gene is provided as part of a polycistronic sequence also encoding the protein of interest.

In still other embodiments of the present invention, the retroviral vectors may comprise recombination elements recognized by a recombination system (e.g., the cre/loxP or flp recombinase systems: See, e.g., Hoess et al., Nucleic Acids Res., 14:2287 [1986], O'Gorman et al., Science 251:1351 [1991], van Deursen et al., Proc. Natl. Acad. Sci. USA 92:7376 [1995], and U.S. Pat. No. 6,025,192, incorporated herein by reference). After integration of the vectors into the genome of the host cell, the host cell can be transiently transfected (e.g., by electroporation, lipofection, or microinjection) with either a recombinase enzyme (e.g., Cre recombinase) or a nucleic acid sequence encoding the recombinase enzyme and one or more nucleic acid sequences encoding a protein of interest flanked by sequences recognized by the recombination enzyme so that the nucleic acid sequence of interest is inserted into the integrated vector.

Viral vectors, including recombinant retroviral vectors, provide a more efficient means of transferring genes into cells, as compared to other techniques such as calcium phosphate-DNA co-precipitation or DEAE-dextran-mediated transfection, electroporation or microinjection of nucleic acids. Nonetheless, the present invention is not limited to any particular mechanism. Indeed, an understanding of the mechanism is not required to practice the present invention. Nevertheless, it is believed that the efficiency of viral transfer is due in part to the fact that the transfer of nucleic acid is a receptor-mediated process (i.e., the virus binds to a specific receptor protein on the surface of the target cell). In addition, once inside a cell, the virally transferred nucleic acid integrates in controlled manner. This is in contrast to nucleic acids transferred by other means (e.g., calcium phosphate-DNA co-precipitation), which are typically subject to rearrangement and degradation.

Example 1, below, describes several illustrative examples of retroviral vectors of the current invention. However, it is not intended that the present invention be limited to the vectors described in Example 1. Indeed, any suitable retroviral vectors containing the novel elements of the present invention are contemplated. Furthermore, the elements described above find use in other vectors such as AAV vectors, transpose vectors, plasmids, bacterial artificial chromosomes, and yeast artificial chromosomes.

III. Expression of Proteins

In some embodiments of the present invention, the vectors and regulatory elements described above find use in the expression of one or more proteins. The present invention is not limited to the production of any particular protein. Indeed, the production of a wide variety of proteins is contemplated, including, but not limited to, erythropoietin, alpha-interferon, alpha-1 proteinase inhibitor, angiogenin, antithrombin III, beta-acid decarboxylase, human growth hormone, bovine growth hormone, porcine growth hormone, human serum albumin, beta-interferon, calf intestine alkaline phosphatase, cystic fibrosis transmembrane regulator, Factor VIII, Factor IX, Factor X, insulin, lactoferrin, tissue plasminogen activator, myelin basic protein, insulin, proinsulin, prolactin, hepatitis B antigen, immunoglobulins, monoclonal antibody CTLA4 Ig, Tag 72 monoclonal antibody, Tag 72 single chain antigen binding protein, protein C, cytokines and their receptors (e.g., tumor necrosis factor alpha and beta), growth hormone releasing factor, parathyroid hormone, thyroid stimulating hormone, lipoproteins, alpha-1-antitrypsin, follicle stimulating hormone, calcitonin, luteinizing hormone, glucagon, von Willebrands factor, atrial natriuretic factor, lung surfactant, urokinase, bombesin, thrombin, hemopoietic growth factor, enkephalinase, human macrophage inflammatory protein (MIP-1-alpha), serum albumins (e.g., mullerian-inhibiting substance), relaxin A-chain, relaxin B-chain, prorelaxin, mouse gonadotropin-associated peptide, beta-lactamase, DNase, inhibin, activin, vascular endothelial growth factor (VEGF), receptors for hormones or growth factors, integrin, protein A or D, rheumatoid factors, neurotrophic factors (e.g., bone-derived neurotrophic factor (BDNF)), neurotrophin-3, -4, -5, or -6 (NT-3, NT-4, NT-5, or NT-6), nerve growth factors (e.g., NGF-beta), platelet-derived growth factor (PDGF), fibroblast growth factors (e.g., aFGF and bFGF), epidermal growth factor (EGF), transforming growth factor (TGF) (e.g., TGF-alpha and TGF-beta, including TGF-$\beta$1, TGF-$\beta$2, TGF-$\beta$3, TGF-$\beta$4, or TGF-$\beta$5), insulin-like growth factor-I and -II (IGF-I and IGF-II), des(1-3)-IGF-I (brain IGF-I), insulin like growth factor binding proteins; CD proteins (e.g., CD-3, CD-4, CD-8, and CD-19), osteoinductive factors, immunotoxins, bone morphogenetic protein (BMP); interferons (e.g., interferon-alpha, -beta, and -gamma), colony stimulating factors (CSFs) (e.g., M-CSF, GM-CSF, and G-CSF), interleukins (IL) (e.g., IL-1 to IL-10), superoxide dismutase, T-cell receptors, surface membrane proteins, decay accelerating factor, viral antigens (e.g., a portion of the AIDS envelope), transport proteins, homing receptors, addressins, regulatory proteins, antibodies, chimeric proteins (e.g., immunoadhesins), and fragments of any of the above-listed polypeptides. One skilled in the art recognizes that the nucleic acid sequences for these proteins and their homologs are available from public databases (e.g., Gen Bank).

In some embodiments, the vectors of the present invention are used to express more than one exogenous protein. For example, host cells may be transfected with vectors encoding different proteins of interest (e.g., cotransfection with one vector encoding a first protein of interest and a second vector encoding a second protein of interest). In other embodiments, more than one protein is expressed by arranging the nucleic acids encoding the different proteins of interest in a polycistronic sequence (e.g., bicistronic or tricistronic sequences). This arrangement is especially useful when expression of the different proteins of interest in a 1:1 molar ratio is desired (e.g., expression of the light and heavy chains of an immunoglobulin molecule).

A. Expression of Protein in Cell Culture

In some embodiments of the present invention, proteins are expressed in cell culture. In some embodiments, retroviral vectors are used to express protein in mammalian tissue culture host cells, including, but not limited to, rat fibroblast cells, bovine kidney cells, and human kidney cells, while in some preferred embodiments, protein is expressed in bovine mammary cells. The host cells are cultured according to methods known in the art; suitable culture conditions for mammalian cells are well known in the art (See e.g., J. Immunol. Methods 56:221 [1983], Animal Cell Culture: A Practical Approach 2nd Ed., Rickwood, D. and Hames, B. D., eds. Oxford University Press, New York [1992]).

The present invention contemplates the transfection of a variety of host cells with integrating vectors. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular protein of interest into the culture medium. Examples of suitable mammalian host cells include, but are not limited to Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); and a human hepatoma line (Hep G2).

In addition to mammalian cell lines, the present invention also contemplates the transfection of plant protoplasts with integrating vectors at a low or high multiplicity of infection. For example, the present invention contemplates a plant cell or whole plant comprising at least one integrated integrating vector, preferably a retroviral vector, and most preferably a pseudotyped retroviral vector. All plants that can be produced by regeneration from protoplasts can also be transfected using the process according to the invention (e.g., cultivated plants of the genera *Solanum, Nicotiana, Brassica, Beta, Pisum, Phaseolus, Glycine, Helianthus, Allium, Avena, Hordeum, Oryzae, Setaria, Secale, Sorghum, Triticum, Zea, Musa, Cocos, Cydonia, Pyrus, Malus, Phoenix, Elaeis, Rubus, Fragaria, Prunus, Arachis, Panicum, Saccharum, Coffea, Camellia, Ananas, Vitis* or *Citrus*). In general, protoplasts are produced in accordance with conventional methods (See, e.g., U.S. Pat. Nos. 4,743,548; 4,677,066, 5,149,645; and 5,508,184; all of which are incorporated herein by reference). Plant tissue may be dispersed in an appropriate medium having an appropriate osmotic potential (e.g., 3 to 8 wt. % of a sugar polyol) and one or more polysaccharide hydrolases (e.g., pectinase, cellulase, etc.), and the cell wall degradation allowed to proceed for a sufficient time to provide protoplasts. After filtration the protoplasts may be isolated by centrifugation and may then be resuspended for subsequent treatment or use. Regeneration of protoplasts kept in culture to whole plants is performed by methods known in the art (See, e.g., Evans et al., *Handbook of Plant Cell Culture*, 1:124-176, MacMillan Publishing Co., New York [1983]; Binding, *Plant Protoplasts*, p. 21-37, CRC Press, Boca Raton [1985],) and Potrykus and Shillito, *Methods in Enzymology*, Vol. 118, Plant Molecular Biology, A. and H. Weissbach eds., Academic Press, Orlando [1986]).

The present invention also contemplates the use of amphibian and insect host cell lines. Examples of suitable insect host cell lines include, but are not limited to, mosquito cell lines (e.g., ATCC CRL-1660). Examples of suitable amphibian host cell lines include, but are not limited to, toad cell lines (e.g., ATCC CCL-102).

In preferred embodiments of the present invention, the host cell cultures are prepared in a medium suitable for the particular cell being cultured. Commercially available media such as Ham's F10 (Sigma, St. Louis, Mo.), Minimal Essential Medium (MEM, Sigma), RPMI-1640 (Sigma), and Dulbecco's Modified Eagle's Medium (DMEM, Sigma) are exemplary nutrient solutions. Suitable media are also described in U.S. Pat. Nos. 4,767,704; 4,657,866; 4,927,762; 5,122,469 and U.S. Pat. No. 4,560,655; and PCT Publications WO 90/03430; and WO 87/00195 (each of which are incorporated herein by reference). Any of these media may be supplemented as necessary, with hormones and/or other growth factors (e.g., insulin, transferrin, or epidermal growth factor), salts (e.g., sodium chloride, calcium, magnesium, and phosphate), buffers (e.g., HEPES), nucleosides (e.g., adenosine and thymidine), antibiotics (e.g., gentamycin (gentamicin)), trace elements (i.e., inorganic compounds usually present at final concentrations in the micromolar range) lipids (e.g., linoleic or other fatty acids) and their suitable carriers, and glucose or an equivalent energy source. Any other necessary supplements may also be included at appropriate concentrations known to those skilled in the art. For mammalian cell culture, the osmolality of the culture medium is generally about 290-330 mOsm.

The present invention also contemplates the use of a variety of culture systems (e.g., petri dishes, 96 well plates, roller bottles, and bioreactors) for the growth and expression of host cells. For example, the host cells can be cultured in a perfusion system. Perfusion culture refers to providing a continuous flow of culture medium through a culture maintained at high cell density. The cells are suspended and do not require a solid support upon which to grow. Generally, fresh nutrients must be supplied continuously with concomitant removal of toxic metabolites and, ideally, selective removal of dead cells. Filtering, entrapment and microcapsulation methods are all suitable for refreshing the culture environment at sufficient rates.

In alternative embodiments, a fed batch culture procedure is employed. In the preferred fed batch culture method the mammalian host cells and culture medium are supplied to a culturing vessel initially and additional culture nutrients are fed, continuously or in discrete increments, to the culture during culturing, with or without periodic cell and/or product harvest before termination of culture. In some embodiments, the fed batch culture is a semi-continuous fed batch culture in which the whole culture (including cells and medium) is removed from the growth vessel and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture (e.g., by filtration, encapsulation, anchoring to microcarriers etc.) and the culture medium is continuously or intermittently introduced and removed from the culturing vessel).

Further, the cells of the culture may be propagated according to any scheme or routine suitable for the particular host cell and the particular production plan contemplated. Therefore, the present invention contemplates single step, as well as multiple step culture procedures. In a single step culture, the host cells are inoculated into a culture environment and the processes of the instant invention are employed during a single production phase of the cell culture. In the multi-stage culture procedure, cells are cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

Fed batch or continuous cell culture conditions are contemplated in order to enhance growth of the mammalian cells in the growth phase of the cell culture. In the growth phase, cells are grown under conditions and for a period of time that is optimized for growth. Culture conditions, such as temperature, pH, dissolved oxygen ($dO_2$) and the like, are those used with the particular host and are apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells (e.g., CHO cells) is between about 30° to 38° C. and a suitable $dO_2$ is between 5-90% of air saturation.

Following the polypeptide production phase, the polypeptide of interest is recovered from the culture medium using well-established techniques. Preferably, the protein of interest is recovered from the culture medium as a secreted polypeptide (e.g., the secretion of the protein of interest is directed by a signal peptide sequence), although it also may be recovered from host cell lysates. As a first step, the culture medium or lysate is centrifuged to remove particulate cell debris. The polypeptide is then purified from contaminant soluble proteins and polypeptides using any suitable method. Suitable purificaiton methods include, but are not limited to fractionation on immunoaffinity or ion-exchange columns; ethanol precipitation; reverse phase HPLC; chromatography on silica or on a cation-exchange resin such as DEAE; chromatofocusing; SDS-PAGE;

ammonium sulfate precipitation; gel filtration using (e.g., Sephadex G-75); and protein A Sepharose columns to remove contaminants such as IgG. A protease inhibitor such as phenyl methyl sulfonyl fluoride (PMSF) also may be useful to inhibit proteolytic degradation during purification. Additionally, the protein of interest can be fused in frame to a marker sequence which allows for purification of the protein of interest. Non-limiting examples of marker sequences include a hexahistidine tag which may be supplied by a vector, preferably a pQE-9 vector, and a hemagglutinin (HA) tag. The HA tag corresponds to an epitope derived from the influenza hemagglutinin protein (See e.g., Wilson et al., Cell, 37:767 [1984]). One skilled in the art appreciates that purification methods suitable for the polypeptide of interest may require modification to account for changes in the character of the polypeptide upon expression in recombinant cell culture.

B. Expression of Proteins in Animals

In some embodiments of the present invention, the host cell utilized for expression of the protein of interest is part of a mammal. In preferred embodiments, the mammal is a transgenic bovine. The transgenic bovine may be produced by any suitable method (See e.g., Chan et al., PNAS, 95:14028 [1998]; U.S. Pat. No. 5,741,957 (incorporated herein by reference); and Pursel et al., Science, 244:1281 [1989]). In particularly preferred embodiments, the protein is expressed in the mammary gland of a bovine and secreted in the milk of the bovine. In embodiments where proteins are expressed in the milk of a bovine, proteins and signal sequences for tissue specific expression and secretion are utilized, including, but not limited to, bovine/human α-lactalbumin promoter and bovine α-lactalbumin signal sequence. The protein of interest may be recovered from bovine milk using any suitable method, including but not limited to, those described above for the recovery of protein from cell cultures.

Those skilled in the art recognize that the vectors of the present invention will find use in the production of other transgenic animals as well, including, but not limited to, mice, goats, pigs, birds and rabbits (See e.g., U.S. Pat. Nos. 5,523,226; 5,453,457; 4,873,191; 4,736,866; each of which is herein incorporated by reference).

C. Expression of Antibodies

In some embodiments of the present invention, single vectors are utilized for the expression of two or more proteins, including individual subunits of multisubunit proteins. In some embodiments, two or more chains of an immunoglobulin (e.g., one heavy chain ((γ, α, μ, δ, or ε) and one light chain (κ or λ)), separated by an IRES sequence, are expressed from the same vector as single transcriptional unit. The present invention is not limited to any particular vector. Indeed, the use of a variety of vectors is contemplated, including, but not limited to plasmids, cosmids, bacterial artificial chomosomes, yeast artificial chromosomes, adeno-associated virus vectors, and adenovirus vectors. Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In some particularly preferred embodiments, retroviral vectors are used to express immunoglobulins. In some embodiments, retroviral vectors for expression of immunoglobulins contain regulatory elements. In some preferred embodiments of the present invention, two immunoglobulins chains are expressed in the same retrovirus vector construct separated by an IRES sequence. In some particularly preferred embodiments, the two chains are separated by an IRES/α-LA signal sequence. In other embodiments, the vector further contains RNA export elements. In further embodiments, the RNA export element is a WPRE. In still other embodiments, the PPE element is at least one Mertz sequence. In some preferred embodiments, the PPE element is mutated to remove start signals. In other preferred embodiments, two PPE elements are placed in a head to tail array separated by a linker.

In preferred embodiments, expression of immunoglobulins by the vectors of the current invention is controlled by a promoter. In some embodiments, expression is controlled by a CMV promoter, while in other embodiments, expression is controlled by a MMTV promoter. In some preferred embodiments, expression is controlled by a hybrid bovine/human α-LA promoter.

In some embodiments of the present invention, heavy and light chains are expressed by the vectors of the current invention of a ratio of about 0.7:1.3. In preferred embodiments, heavy and light chains are expressed and a ratio of about 0.8:1.2. In particularly preferred embodiments, heavy and light chains are expressed at a ratio of about 0.9:1.1. In still more preferred embodiments, heavy and light chains are expressed at a ratio of about 1:1. In particularly preferred embodiments, the majority (e.g., greater that 90%, preferably greater than 95%, and most preferably greater than about 99%) of the heavy and light chains are correctly assembled in a ratio of 1:1 to form a functional (e.g., able to bind an antigen) antibody.

In illustrative examples of the present invention, immunoglobulins are expressed in a host cell comprising the vectors and elements described above. In some illustrative examples (See e.g., Examples 6, 8, and 12), the vectors described in Example 1 are used to express a variety of immunoglobulins in a variety of cell lines. In general, this expression led to the formation of functional, tetrameric immunoglobulins.

D. Expression of Other Proteins

The vectors of the present invention are also useful for expressing G-protein coupled receptors (GPCRs) and other transmembrane proteins. It is contemplated that when these proteins are expressed, they are correctly inserted into the membrane in their native conformation. Thus, GPCRs and other transmembrane proteins may be purified as part of a membrane fraction or purified from the membranes by methods known in the art.

Furthermore, the vectors of the present invention are useful for co-expressing a protein of interest for which there is no assay or for which assays are difficult. In this system, a protein of interest and a signal protein are arranged in a polycistronic sequence. Preferably, an IRES sequence separates the signal protein and protein of interest (e.g., a GPCR) and the genes encoding the signal protein and protein of interest are expressed as a single transcriptional unit. The present invention is not limited to any particular signal protein. Indeed, the use of a variety of signal proteins for which easy assays exist is contemplated. These signal proteins include, but are not limited to, green fluorescent protein, luciferase, beta-galactosidase, and antibody heavy or light chains. It is contemplated that when the signal protein and protein of interest are co-expressed from a polycistronic sequence, the presence of the signal protein is indicative of the presence of the protein of interest. Accordingly, in some embodiments, the present invention provides methods for indirectly detecting the expression of protein of interest comprising providing a host cell transfected with a vector encoding a polycistronic sequence, wherein the polycistronic sequence comprises a signal protein and a protein of interest operably linked by an IRES, and culturing the host cells under conditions such that the signal protein and protein of interest are produced, wherein the presence of the signal protein indicates the presence of the protein of interest.

Experimental

The following examples serve to illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms);pg (picograms); L (liters); ml (milliliters); µl (microliters); cm (centimeters); mm (millimeters); µm (micrometers); nm (nanometers); ° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (National Institutes of Health, Besthesda, Md.); RNA (ribonucleic acid); PBS (phosphate buffered saline); g (gravity); OD (optical density); HEPES (N-[2-αHydroxyethyl]piperazine-N-[2-ethanesulfonic acid]); HBS (HEPES buffered saline); PBS (phosphate buffered saline); SDS (sodium dodecylsulfate); Tris-HCl (tris [Hydroxymethyl]aminomethane-hydrochloride); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); ORI (plasmid origin of replication); lacI (lac repressor); X-gal (5-bromo-4-chloro-3-indolyl-β-D-galactoside); ATCC (American Type Culture Collection, Rockville, Md.); GIBCO/BRL (GIBCO/BRL, Grand Island, N.Y.); Perkin-Elmer (Perkin-Elmer, Norwalk, Conn.); and Sigam (Sigma Chemical Company, St. Louis, Mo.).

EXAMPLE 1

Vector Construction

The following Example describes the construction of vectors used in the experiments below.

A. CMV MN14

The CMV MN14 vector (SEQ ID NO:4; MN14 antibody is described in U.S. Pat. No. 5,874,540, incorporated herein by reference) comprises the following elements, arranged in 5' to 3' order: CMV promoter; MN14 heavy chain signal peptide, MN14 antibody heavy chain; IRES from encephalomyocarditis virus; bovine α-lactalbumin signal peptide; MN 14 antibody light chain; and 3' MoMuLV LTR. In addition to sequences described in SEQ ID NO: 4, the CMV MN14 vector further comprises a 5' MoMuLV LTR, a MoMuLV extended viral packaging signal, and a neomycin phosphotransferase gene (these additional elements are provided in SEQ ID NO:7; the 5' LTR is derived from Moloney Murine Sarcoma Virus in each of the constructs described herein, but is converted to the MoMuLV 5' LTR when integrated).

This construct uses the 5' MoMuLV LTR to control production of the neomycin phosphotransferase gene. The expression of MN14 antibody is controlled by the CMV promoter. The MN14 heavy chain gene and light chain gene are attached together by an IRES sequence. The CMV promoter drives production of a mRNA containing the heavy chain gene and the light chain gene attached by the IRES. Ribosomes attach to the mRNA at the CAP site and at the IRES sequence. This allows both heavy and light chain protein to be produced from a single mRNA. The mRNA expression from the LTR as well as from the CMV promoter is terminated and poly adenylated in the 3' LTR. The construct was cloned by similar methods as described in section B below.

The IRES sequence (SEQ ID NO:3) comprises a fusion of the IRES from the plasmid pLXIN (Clontech) and the bovine α-lactalbumin signal peptide. The initial ATG of the signal peptide was attached to the IRES to allow the most efficient translation initiation from the IRES. The 3' end of the signal peptide provides a multiple cloning site allowing easy attachment of any protein of interest to create a fusion protein with the signal peptide. The IRES sequence can serve as a translational enhancer as well as creating a second translation initiation site that allows two proteins to be produced from a single mRNA.

The IRES-bovine α-lactalbumin signal peptide was constructed as follows. The portion of the plasmid pLXIN (Clontech, Palo Alto, Calif.) containing the ECMV IRES was PCR amplified using the following primers.

```
Primer 1:
5' GATCCACTAGTAACGGCCGCCAGAATT    (SEQ ID NO: 35)
CGC 3'

Primer 2:
5' CAGAGAGACAAAGGAGGCCATATTATC    (SEQ ID NO: 36)
ATCGTGTTTTTCAAAG 3'
```

Primer 2 attaches a tail corresponding to the start of the bovine α-lactalbumin signal peptide coding region to the IRES sequence. In addition, the second triplet codon of the α-lactalbumin signal peptide was mutated from ATG to GCC to allow efficient translation from the IRES sequence. This mutation results in a methionine to alanine change in the protein sequence. This mutation was performed because the IRES prefers an alanine as the second amino acid in the protein chain. The resulting IRES PCR product contains an EcoRI site on the 5' end of the fragment (just downstream of Primer 1 above).

Next, the α-lactalbumin signal peptide containing sequence was PCR amplified from the α-LA Signal Peptide vector construct using the following primers.

```
Primer 3:
5' CTTTGAAAAACACGATGATAATATGGC    (SEQ ID NO: 14)
CTCCTTTGTCTCTCTG 3'

Primer 4:
5' TTCGCGAGCTCGAGATCTAGATATCCC    (SEQ ID NO: 15)
ATG 3'
```

Primer 3 attaches a tail corresponding to the 3' end of the IRES sequence to the α-lactalbumin signal peptide coding region. As stated above, the second triplet codon of the bovine α-lactalbumin signal peptide was mutated to allow efficient translation from the IRES sequence. The resulting signal peptide PCR fragment contains NaeI, NcoI, EcoRV, XbaI, BglII and XhoI sites on the 3' end.

After the IRES and signal peptide were amplified individually using the primers shown above, the two reaction products were mixed and PCR was performed using primer 1 and primer 4. The resultant product of this reaction is a spliced fragment that contains the IRES attached to the full length α-lactalbumin signal peptide. The ATG encoding the start of the signal peptide is placed at the same location as the ATG encoding the start of the neomycin phosphotransferase gene found in the vector pLXIN. The fragment also contains the EcoRI site on the 5' end and NaeI, NcoI, EcoRV, XbaI, BglII and XhoI sites on the 3' end.

The spliced IRES/α-lactalbumin signal peptide PCR fragment was digested with EcoRI and XhoI. The α-LA Signal Peptide vector construct was also digested with EcoRI and XhoI. These two fragments were ligated together to give the pIRES construct.

The IRES/α-lactalbumin signal peptide portion of the pIRES vector was sequenced and found to contain mutations in the 5' end of the IRES. These mutations occur in a long stretch of C's and were found in all clones that were isolated.

To repair this problem, pLXIN DNA was digested with EcoRI and BsmFI. The 500 bp band corresponding to a portion of the IRES sequence was isolated. The mutated IRES/α-lactalbumin signal peptide construct was also digested with EcoRI and BsmFI and the mutated IRES fragment was removed. The IRES fragment from pLXIN was then substituted for the IRES fragment of the mutated IRES/α-lactalbumin signal peptide construct. The IRES/α-LA signal peptide portion of resulting plasmid was then verified by DNA sequencing.

The resulting construct was found to have a number of sequence differences when compared to the expected pLXIN sequence obtained from Clontech. We also sequenced the IRES portion of pLXIN purchased from Clontech to verify its sequence. The differences from the expected sequence also appear to be present in the pLXIN plasmid that we obtained from Clontech. Four sequence differences were identified:

bp 347 T—was G in pLXIN sequence
bp 786-788 ACG—was GC in LXIN sequence.

B. CMV LL2

The CMV LL2 (SEQ ID NO:5; LL2 antibody is described in U.S. Pat. No. 6,187,287, incorporated herein by reference) construct comprises the following elements, arranged in 5' to 3' order: 5' CMV promoter (Clontech), LL2 heavy chain signal peptide, LL2 antibody heavy chain; IRES from encephalomyocarditis virus; bovine α-LA signal peptide; LL2 antibody light chain; and 3' MoMuLV LTR. In addition to sequences described in SEQ ID NO:5, the CMV LL2 vector further comprises a 5' MoMuLV LTR, a MoMuLV extended viral packaging signal, and a neomycin phosphotransferase gene (these additional elements are provided in SEQ ID NO:7).

This construct uses the 5' MoMuLV LTR to control production of the neomycin phosphotransferase gene. The expression of LL2 antibody is controlled by the CMV promoter (Clontech). The LL2 heavy chain gene and light chain gene are attached together by an IRES sequence. The CMV promoter drives production of a mRNA containing the heavy chain gene and the light chain gene attached by the IRES. Ribosomes attach to the mRNA at the CAP site and at the IRES sequence. This allows both heavy and light chain protein to be produced from a single mRNA. The mRNA expression from the LTR as well as from the CMV promoter is terminated and poly adenylated in the 3' LTR.

The IRES sequence (SEQ ID NO:3) comprises a fusion of the IRES from the plasmid pLXIN (Clontech) and the bovine alpha-lactalbumin signal peptide. The initial ATG of the signal peptide was attached to the IRES to allow the most efficient translation initiation from the IRES. The 3' end of the signal peptide provides a multiple cloning site allowing easy attachment of any protein of interest to create a fusion protein with the signal peptide. The IRES sequence can serve as a translational enhancer as well as creating a second translation initiation site that allows two proteins to be produced from a single mRNA.

The LL2 light chain gene was attached to the IRES α-lactalbumin signal peptide as follows. The LL2 light chain was PCR amplified from the vector pCRLL2 using the following primers.

```
Primer 1:
5' CTACAGGTGTCCACGTCGACATCCAGC    (SEQ ID NO: 16)
TGACCCAG 3'
```

-continued

```
Primer 2:
5' CTGCAGAATAGATCTCTAACACTCTCC    (SEQ ID NO: 17)

CCTGTTG 3'
```

These primers add a HincII site right at the start of the coding region for mature LL2 light chain. Digestion of the PCR product with HincII gives a blunt end fragment starting with the initial GAC encoding mature LL2 on the 5' end. Primer 2 adds a BglII site to the 3' end of the gene right after the stop codon. The resulting PCR product was digested with HincII and BglII and cloned directly into the IRES-Signal Peptide plasmid that was digested with NaeI and BglII.

The Kozak sequence of the LL2 heavy chain gene was then modified. The vector pCRMN14HC was digested with XhoI and AvrII to remove about a 400 bp fragment. PCR was then used to amplify the same portion of the LL2 heavy chain construct that was removed by the XhoI-AvrII digestion. This amplification also mutated the 5' end of the gene to add a better Kozak sequence to the clone. The Kozak sequence was modified to resemble the typical IgG Kozak sequence. The PCR primers are shown below.

```
Primer 1:
5' CAGTGTGATCTCGAGAATTCAGGACC    (SEQ ID NO: 18)

TCACCATGGGATGGAGCTGTATCAT 3'

Primer 2:
5' AGGCTGTATTGGTGGATTCGTCT 3'    (SEQ ID NO: 19)
```

The PCR product was digested with XhoI and AvrII and inserted back into the previously digested plasmid backbone.

The "good" Kozak sequence was then added to the light chain gene. The "good" Kozak LL2 heavy chain gene construct was digested with EcoRI and the heavy chain gene containing fragment was isolated. The IRES α-Lactalbumin Signal Peptide LL2 light chain gene construct was also digested with EcoRI. The heavy chain gene was then cloned into the EcoRI site of IRES light chain construct. This resulted in the heavy chain gene being placed at the 5' end of the IRES sequence.

Next, a multiple cloning site was added into the LNCX retroviral backbone plasmid. The LNCX plasmid was digested with HindIII and ClaI. Two oligonucleotide primers were produced and annealed together to create an double stranded DNA multiple cloning site. The following primers were annealed together.

```
Primer 1:
5' AGCTTCTCGAGTTAACAGATCTAGGCC    (SEQ ID NO: 20)

TCCTAGGTCGACAT 3'

Primer 2:
5' CGATGTCGACCTAGGAGGCCTAGATCT    (SEQ ID NO: 21)

GTTAACTCGAGA 3'
```

After annealing, the multiple cloning site was ligated into LNCX to create LNC-MCS.

Next, the double chain gene fragment was ligated into the retroviral backbone gene construct. The double chain gene construct created above was digested with SalI and BglII and the double chain containing fragment was isolated. The retroviral expression plasmid LNC-MCS was digested with XhoI and BglII. The double chain fragment was then cloned into the LNC-MCS retroviral expression backbone.

Next, an RNA splicing problem in the construct was corrected. The construct was digested with NsiI. The resulting fragment was then partially digested with EcoRI. The fragments resulting from the partial digest that were approximately 9300 base pairs in size were gel purified. A linker was created to mutate the splice donor site at the 3' end of the LL2 heavy chain gene. The linker was again created by annealing two oligonucleotide primers together to form the double stranded DNA linker. The two primers used to create the linker are shown below.

```
Primer 1:
5'CGAGGCTCTGCACAACCACTACACGCAG    (SEQ ID NO: 22)

AAGAGCCTCTCCCTGTCTCCCGGGAAATGA

AAGCCG 3'

Primer 2:
5'AATTCGGCTTTCATTTCCCGGGAGACAG    (SEQ ID NO: 23)

GGAGAGGCTCTTCTGCGTGTAGTGGTTGTG

CAGAGCCTCGTGCA 3'
```

After annealing the linker was substituted for the original NsiI/EcoRI fragment that was removed during the partial digestion.

C. MMTV MN14

The MMTV MN14 (SEQ ID NO:6) construct comprises the following elements, arranged in 5' to 3' order: 5' MMTV promoter; double mutated PPE sequence; MN 14 antibody heavy chain; IRES from encephalomyocarditis virus; bovine αLA signal peptide MN 14 antibody light chain; WPRE sequence; and 3' MoMuLV LTR. In addition to the sequences described in SEQ ID NO:6, the MMTV MN14 vector further comprises a MoMuLV LTR, MoMuLV extended viral packaging signal; neomycin phosphotransferase gene located 5' of the MMTV promoter (these additional elements are provided in SEQ ID NO: 7).

This construct uses the 5' MoMuLV LTR to control production of the neomycin phosphotransferase gene. The expression of MN14 antibody is controlled by the MMTV promoter (Pharmacia). The MN14 heavy chain gene and light chain gene are attached together by an IRES/bovine α-LA signal peptide sequence (SEQ ID NO: 3). The MMTV promoter drives production of a mRNA containing the heavy chain gene and the light chain gene attached by the IRES/bovine α-LA signal peptide sequence. Ribosomes attach to the mRNA at the CAP site and at the IRES/bovine α-LA signal peptide sequence. This allows both heavy and light chain protein to be produced from a single mRNA. In addition, there are two genetic elements contained within the mRNA to aid in export of the mRNA from the nucleus to the cytoplasm and aid in poly-adenylation of the mRNA. The PPE sequence is contained between the RNA CAP site and the start of the MN14 protein coding region, the WPRE is contained between the end of MN14 protein coding and the poly-adenylation site. The mRNA expression from the LTR as well as from the MMTV promoter is terminated and poly-adenylated in the 3' LTR.

ATG sequences within the PPE element (SEQ ID NO:2) were mutated to prevent potential unwanted translation initiation. Two copies of this mutated sequence were used in a head to tail array. This sequence is placed just downstream of the promoter and upstream of the Kozak sequence and signal peptide-coding region. The WPRE is isolated from woodchuck hepatitis virus and also aids in the export of mRNA from the nucleus and creating stability in the mRNA. If this sequence is included in the 3' untranslated region of the RNA, level of protein expression from this RNA increases up to 10-fold.

D. α-LA MN14

The α-LA MN14 (SEQ ID NO:7) construct comprises the following elements, arranged in 5' to 3' order: 5' MoMuLV LTR, MoMuLV extended viral packaging signal, neomycin phosphotransferase gene, bovine/human alpha-lactalbumin hybrid promoter, double mutated PPE element, MN14 heavy chain signal peptide, MN14 antibody heavy chain, IRES from encephalomyocarditis virus/bovine αLA signal peptide, MN14 antibody light chain, WPRE sequence; and 3' MoMuLV LTR.

This construct uses the 5' MoMuLV LTR to control production of the neomycin phosphotransferase gene. The expression of MN14 antibody is controlled by the hybrid α-LA promoter (SEQ ID NO:1). The MN14 heavy chain gene and light chain gene are attached together by an IRES sequence/bovine α-LA signal peptide (SEQ ID NO:3). The α-LA promoter drives production of a mRNA containing the heavy chain gene and the light chain gene attached by the IRES. Ribosomes attach to the mRNA at the CAP site and at the IRES sequence. This allows both heavy and light chain protein to be produced from a single mRNA.

In addition, there are two genetic elements contained within the mRNA to aid in export of the mRNA from the nucleus to the cytoplasm and aid in poly-adenylation of the mRNA. The mutated PPE sequence (SEQ ID NO:2) is contained between the RNA CAP site and the start of the MN14 protein coding region. ATG sequences within the PPE element (SEQ ID NO:2) were mutated to prevent potential unwanted translation initiation. Two copies of this mutated sequence were used in a head to tail array. This sequence is placed just downstream of the promoter and upstream of the Kozak sequence and signal peptide-coding region. The WPRE was isolated from woodchuck hepatitis virus and also aids in the export of mRNA from the nucleus and creating stability in the mRNA. If this sequence is included in the 3' untranslated region of the RNA, level of protein expression from this RNA increases up to 10-fold. The WPRE is contained between the end of MN14 protein coding and the poly-adenylation site. The mRNA expression from the LTR as well as from the bovine/human alpha-lactalbumin hybrid promoter is terminated and poly adenylated in the 3' LTR.

The bovine/human alpha-lactalbumin hybrid promoter (SEQ ID NO:1) is a modular promoter/enhancer element derived from human and bovine alpha-lactalbumin promoter sequences. The human portion of the promoter is from +15 relative to transcription start point (tsp) to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine.

For construction of the bovine/human α-lactalbumin promoter, human genomic DNA was isolated and purified. A portion of the human α-lactalbumin promoter was PCR amplified using the following two primers:

```
Primer 1:
5'AAAGCATATGTTCTGGGCCTTGTTACAT    (SEQ ID NO: 24)
GGCTGGATTGGTT 3'

Primer 2:
5'TGAATTCGGCGCCCCCAAGAACCTGAAA    (SEQ ID NO: 25)
TGGAAGCATCACTCAGTTTCATATAT 3'
```

This two primers created a NdeI site on the 5' end of the PCR fragment and a EcoRI site on the 3' end of the PCR fragment.

The human PCR fragment created using the above primers was double digested with the restriction enzymes NdeI and EcoRI. The plasmid pKBaP-1 was also double digested with NdeI and EcoRI. The plasmid pKBaP-1 contains the bovine α-lactalbumin 5' flanking region attached to a multiple cloning site. This plasmid allows attachment of various genes to the bovine α-lactalbumin promoter.

Subsequently, the human fragment was ligated/substituted for the bovine fragment of the promoter that was removed from the pKBaP-1 plasmid during the double digestion. The resulting plasmid was confirmed by DNA sequencing to be a hybrid of the Bovine and Human α-lactalbumin promoter/regulatory regions.

Attachment of the MN14 light chain gene to the IRES α-lactalbumin signal peptide was accomplished as follows. The MN14 light chain was PCR amplified from the vector pCRMN14LC using the following primers.

```
Primer 1:
5' CTACAGGTGTCCACGTCGACATCCAGC    (SEQ ID NO: 26)
TGACCCAG 3'

Primer 2:
5' CTGCAGAATAGATCTCTAACACTCTCC    (SEQ ID NO: 27)
CCTGTTG 3'
```

These primers add a HincII site right at the start of the coding region for mature MN14 light chain. Digestion of the PCR product with HincII gives a blunt end fragment starting with the initial GAC encoding mature MN14 on the 5' end. Primer 2 adds a BglII site to the 3' end of the gene right after the stop codon. The resulting PCR product was digested with HincII and BglII and cloned directly into the IRES-Signal Peptide plasmid that was digested with NaeI and BglII.

Next, the vector pCRMN14HC was digested with XhoI and NruI to remove about a 500 bp fragment. PCR was then used to amplify the same portion of the MN14 heavy chain construct that was removed by the XhoI-NruI digestion. This amplification also mutated the 5' end of the gene to add a better Kozak sequence to the clone. The Kozak sequence was modified to resemble the typical IgG Kozak sequence. The PCR primers are shown below.

```
Primer 1:
5'CAGTGTGATCTCGAGAATTCAGGACCTC    (SEQ ID NO: 28)
ACCATGGGATGGAGCTGTATCAT 3'

Primer 2:
5'GTGTCTTCGGGTCTCAGGCTGT 3'        (SEQ ID NO: 29)
```

The PCR product was digested with XhoI and NruI and inserted back into the previously digested plasmid backbone.

Next, the "good" Kozak MN14 heavy chain gene construct was digested with EcoRI and the heavy chain gene containing fragment was isolated. The IRES α-Lactalbumin Signal Peptide MN14 light chain gene construct was also digested with EcoRI. The heavy chain gene was then cloned into the EcoRI site of IRES light chain construct. This resulted in the heavy chain gene being placed at the 5' end of the IRES sequence.

A multiple cloning site was then added to the LNCX retroviral backbone plasmid. The LNCX plasmid was digested with HindIII and ClaI. Two oligonucleotide primers were produced and annealed together to create an double stranded DNA multiple cloning site. The following primers were annealed together.

```
Primer 1:
5' AGCTTCTCGAGTTAACAGATCTAGGCC    (SEQ ID NO: 30)

TCCTAGGTCGACAT 3'

Primer 2:
5' CGATGTCGACCTAGGAGGCCTAGATCT    (SEQ ID NO: 31)

GTTAACTCGAGA 3'
```

After annealing the multiple cloning site was ligated into LNCX to create LNC-MCS.

The double chain gene fragment was then inserted into a retroviral backbone gene construct. The double chain gene construct created in step 3 was digested with SalI and BglII and the double chain containing fragment was isolated. The retroviral expression plasmid LNC-MCS was digested with XhoI and BglII. The double chain fragment was then cloned into the LNC-MCS retroviral expression backbone.

Next, a RNA splicing problem in the construct was repaired. The construct was digested with NsiI. The resulting fragment was then partially digested with EcoRI. The fragments resulting from the partial digest that were approximately 9300 base pairs in size, were gel purified. A linker was created to mutate the splice donor site at the 3' end of the MN14 heavy chain gene. The linker was again created by annealing two oligonucleotide primers together to form the double stranded DNA linker. The two primers used to create the linker are shown below.

```
Primer 1:                                                      (SEQ ID NO: 32)
5' CGAGGCTCTGCACAACCACTACACGCAGAAGAGCCTCTCCCTGTCTCCCGGGAAAT

GAAAGCCG 3'

Primer 2:                                                      (SEQ ID NO: 33)
5' AATTCGGCTTTCATTTCCCGGGAGACAGGGAGAGGCTCTTCTGCGTGTAGTGGTTG

TGCAGAGCCTCGTGCA 3'
```

After annealing the linker was substituted for the original NsiI/EcoRI fragment that was removed during the partial digestion.

Next, the mutated double chain fragment was inserted into the α-Lactalbumin expression retroviral backbone LN α-LA-Mertz-MCS. The gene construct produced above was digested with BamHI and BglII and the mutated double chain gene containing fragment was isolated. The LN α-LA-Mertz-MCS retroviral backbone plasmid was digested with BglII. The BamHI/BglII fragment was then inserted into the retroviral backbone plasmid.

A WPRE element was then inserted into the gene construct. The plasmid BluescriptII SK+ WPRE-B11 was digested with BamHI and HincII to remove the WPRE element and the element was isolated. The vector created above was digested with BglII and HpaI. The WPRE fragment was ligated into the BglII and HpaI sites to create the final gene construct.

E. α-LA Bot

The α-LA Bot (SEQ ID NO:8, botulinum toxin antibody) construct comprises the following elements, arranged in 5' to 3' order: bovine/human alpha-lactalbumin hybrid promoter, mutated PPE element, cc49 signal peptide, botulinum toxin antibody light chain, IRES from encephalomyocarditis virus/bovine α-LA signal peptide, botulinum toxin antibody heavy chain, WPRE sequence, and 3' MoMuLV LTR. In addition, the α-LA botulinum toxin antibody vector further comprises a 5' MoMuLV LTR, a MoMuLV extended viral packaging signal, and a neomycin phosphotransferase gene (these additional elements are provided in SEQ ID NO: 7).

This construct uses the 5' MoMuLV LTR to control production of the neomycin phosphotransferase gene. The expression of botulinum toxin antibody is controlled by the hybrid a-LA promoter. The botulinum toxin antibody light chain gene and heavy chain gene are attached together by an IRES/bovine α-LA signal peptide sequence. The bovine/human alpha-lactalbumin hybrid promoter drives production of a mRNA containing the light chain gene and the heavy chain gene attached by the IRES. Ribosomes attach to the mRNA at the CAP site and at the IRES sequence. This allows both light and heavy chain protein to be produced from a single mRNA.

In addition, there are two genetic elements contained within the mRNA to aid in export of the mRNA from the nucleus to the cytoplasm and aid in poly-adenylation of the mRNA. The mutated PPE sequence (SEQ ID NO:2) is contained between the RNA CAP site and the start of the MN14 protein coding region. ATG sequences within the PPE element (SEQ ID NO:2) were mutated to prevent potential unwanted translation initiation. Two copies of this mutated sequence were used in a head to tail array. This sequence was placed just downstream of the promoter and upstream of the Kozak sequence and signal peptide-coding region. The WPRE was isolated from woodchuck hepatitis virus and also aids in the export of mRNA from the nucleus and creating stability in the mRNA. If this sequence is included in the 3' untranslated region of the RNA, level of protein expression from this RNA increases up to 10-fold. The WPRE is contained between the end of MN14 protein coding and the poly-adenylation site. The mRNA expression from the LTR as well as from the bovine/human alpha-lactalbumin hybrid promoter is terminated and poly adenylated in the 3' LTR.

The bovine/human α-lactalbumin hybrid promoter (SEQ ID NO:1) is a modular promoter/enhancer element derived from human and bovine α-lactalbumin promoter sequences. The human portion of the promoter is from +15 relative to transcription start point to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine. Likewise, the construct contains control elements present in the bovine but not in the human.

F. LSRNL

The LSRNL (SEQ ID NO:9) construct comprises the following elements, arranged in 5' to 3' order: 5' MoMuLV LTR, MoMuLV viral packaging signal; hepatitis B surface antigen; RSV promoter; neomycin phosphotransferase gene; and 3' MoMuLV LTR.

This construct uses the 5' MoMuLV LTR to control production of the Hepatitis B surface antigen gene. The expression of the neomycin phosphotransferase gene is controlled by the RSV promoter. The mRNA expression from the LTR as well as from the RSV promoter is terminated and poly adenylated in the 3' LTR.

G. α-LA cc49IL2

The α-LA cc49IL2 (SEQ ID NO:10; the cc49 antibody is described in U.S. Pat. Nos. 5,512,443; 5,993,813; and 5,892,019; each of which is herein incorporated by reference) construct comprises the following elements, arranged in 5' to 3' order: 5' bovine/human α-lactalbumin hybrid promoter; cc49-IL2 coding region; and 3' MoMuLV LTR. This gene construct expresses a fusion protein of the single chain antibody cc49 attached to Interleukin-2. Expression of the fusion protein is controlled by the bovine/human α-lactalbumin hybrid promoter.

The bovine/human α-lactalbumin hybrid promoter (SEQ ID NO:1) is a modular promoter/enhancer element derived from human and bovine alpha-lactalbumin promoter sequences. The human portion of the promoter is from +15 relative to transcription start point to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine. Likewise, the construct contains control elements present in the bovine but not in the human. The 3' viral LTR provide the poly-adenylation sequence for the mRNA.

H. α-LA YP

The α-LA YP (SEQ ID NO: 11) construct comprises the following elements, arranged in 5' to 3' order: 5' bovine/human alpha-lactalbumin hybrid promoter; double mutated PPE sequence; bovine αLA signal peptide; *Yersenia pestis* antibody heavy chain Fab coding region; EMCV IRES/bovine α-LA signal peptide; *Yersenia pestis* antibody light chain Fab coding region; WPRE sequence; 3' MoMuLV LTR.

This gene construct will cause the expression of *Yersenia pestis* mouse Fab antibody. The expression of the gene construct is controlled by the bovine/human α-lactalbumin hybrid promoter. The PPE sequence and the WPRE sequence aid in moving the mRNA from the nucleus to the cytoplasm. The IRES sequence allows both the heavy and the light chain genes to be translated from the same mRNA. The 3' viral LTR provides the poly-adenylation sequence for the mRNA.

In addition, there are two genetic elements contained within the mRNA to aid in export of the mRNA from the nucleus to the cytoplasm and aid in poly-adenylation of the mRNA. The mutated PPE sequence (SEQ ID NO:2) is contained between the RNA CAP site and the start of the MN14 protein coding region. ATG sequences within the PPE element (SEQ ID NO:2) were mutated (bases 4, 112, 131, and 238 of SEQ ID NO: 2 were changed from a G to a T) to prevent potential unwanted translation initiation. Two copies of this mutated sequence were used in a head to tail array. This sequence was placed just downstream of the promoter and upstream of the Kozak sequence and signal peptide-coding region. The WPRE was isolated from woodchuck hepatitis virus and also aids in the export of mRNA from the nucleus and creating stability in the mRNA. If this sequence is included in the 3' untranslated region of the RNA, level of protein expression from this RNA increases up to 10-fold. The WPRE is contained between the end of MN14 protein coding and the poly-adenylation site. The mRNA expression from the LTR as well as from the bovine/human alpha-lactalbumin hybrid promoter is terminated and poly adenylated in the 3' LTR.

The bovine/human alpha-lactalbumin hybrid promoter (SEQ ID NO:1) is a modular promoter/enhancer element derived from human and bovine alpha-lactalbumin promoter sequences. The human portion of the promoter is from +15 relative to transcription start point to −600 relative to the tsp. The bovine portion is then attached to the end of the human portion and corresponds to −550 to −2000 relative to the tsp. The hybrid was developed to remove poly-adenylation signals that were present in the bovine promoter and hinder retroviral RNA production. It was also developed to contain genetic control elements that are present in the human gene, but not the bovine. Likewise, the construct contains control elements present in the bovine but not in the human.

EXAMPLE 2

Generation of Cell Lines Stably Expressing the MoMLV gag and pol Proteins

Examples 2-5 describe the production of pseudotyped retroviral vectors. These methods are generally applicable to the production of the vectors described above. The expression of the fusogenic VSV G protein on the surface of cells results in syncytium formation and cell death. Therefore, in order to produce retroviral particles containing the VSV G protein as the membrane-associated protein a two-step approach was taken. First, stable cell lines expressing the gag and pol proteins from MoMLV at high levels were generated (e.g., 293GP$^{SD}$ cells). The stable cell line which expresses the gag and pol proteins produces noninfectious viral particles lacking a membrane-associated protein (e.g., an envelope protein). The stable cell line was then co-transfected, using the calcium phosphate precipitation, with VSV-G and gene of interest plasmid DNAs. The pseudotyped vector generated was used to infect $_{293}$GP$^{SD}$ cells to produce stably transformed cell lines. Stable cell lines can be transiently transfected with a plasmid capable of directing the high level expression of the VSV G protein (see below). The transiently transfected cells produce VSV G-pseudotyped retroviral vectors which can be collected from the cells over a period of 3 to 4 days before the producing cells die as a result of syncytium formation.

The first step in the production of VSV G-pseudotyped retroviral vectors, the generation of stable cell lines expressing the MoMLV gag and pol proteins is described below. The human adenovirus Ad-5-transformed embryonal kidney cell line 293 (ATCC CRL 1573) was cotransfected with the pCMVgag-pol and the gene encoding for phleomycin. pCMV gag-pol contains the MoMLV gag and pol genes under the control of the CMV promoter (pCMV gag-pol is available from the ATCC).

The plasmid DNA was introduced into the 293 cells using calcium phosphate co-precipitation (Graham and Van der Eb, Virol. 52:456 [1973]). Approximately $5\times10^5$ 293 cells were plated into a 100 mm tissue culture plate the day before the DNA co-precipitate was added. Stable transformants were selected by growth in DMEM-high glucose medium containing 10% FCS and 10 µg/ml phleomycin (selective medium). Colonies which grew in the selective medium were screened for extracellular reverse transcriptase activity (Goff et al., J. Virol. 38:239 [1981]) and intracellular p30gag expression. The presence of p30gag expression was determined by Western blotting using a goat-anti p30 antibody (NCI antiserum 77S000087). A clone which exhibited stable expression of the retroviral genes was selected. This clone was named 293GP$^{SD}$ (293 gag-pol-San Diego). The 293GP$^{SD}$ cell line, a derivative of the human Ad-5-transformed embryonal kidney cell line 293, was grown in DMEM-high glucose medium containing 10% FCS.

EXAMPLE 3

Preparation of Pseudotyped Retroviral Vectors Bearing the G Glycoprotein of VSV

In order to produce VSV G protein pseudotyped retrovirus the following steps were taken. The 293GP$^{SD}$ cell line was co-transfected with VSV-G plasmid and DNA plasmid of interest. This co-transfection generates the infectious particles used to infect 293GP$^{SD}$ cells to generate the packaging cell lines. This Example describes the production of pseudotyped LNBOTDC virus. This general method may be used to produce any of the vectors described in Example 1.

a) Cell Lines and Plasmids

The packaging cell line, 293GP$^{SD}$ was grown in alpha-MEM-high glucose medium containing 10% FCS The titer of the pseudo-typed virus may be determined using either 208F cells (Quade, Virol. 98:461 [1979]) or NIH/3T3 cells (ATCC CRL 1658); 208F and NIH/3T3 cells are grown in DMEM-high glucose medium containing 10% CS.

The plasmid LNBOTDC contains the gene encoding BOTD under the transcriptional control of cytomegalovirus intermediate-early promoter followed by the gene encoding neomycin phosphotransferase (Neo) under the transcriptional control of the LTR promoter. The plasmid pHCMV-G contains the VSV G gene under the transcriptional control of the human cytomegalovirus intermediate-early promoter (Yee et al., Meth. Cell Biol. 43:99 [1994]).

b) Production of Stable Packaging Cell Lines, Pseudotyped Vector and Titering of Pseudotyped LNBOTDC Vector LNBOTDC DNA (SEQ ID NO: 13) was co-transfected with pHCMV-G DNA into the packaging line 293GP$^{SD}$ to produce LNBOTDC virus. The resulting LNBOTDC virus was then used to infect 293GP$^{SD}$ cells to transform the cells. The procedure for producing pseudotyped LNBOTDC virus was carried out as described (Yee et al., Meth. Cell Biol. 43:99 [1994].

This is a retroviral gene construct that upon creation of infectious replication defective retroviral vector will cause the insertion of the sequence described above into the cells of interest. Upon insertion the CMV regulatory sequences control the expression of the botulinum toxin antibody heavy and light chain genes. The IRES sequence allows both the heavy and the light chain genes to be translated from the same mRNA. The 3' viral LTR provides the poly-adenylation sequence for the mRNA.

Both heavy and light chain protein for botulinum toxin antibody are produced from this signal mRNA. The two proteins associated to form active botulinum toxin antibody. The heavy and light chain proteins also appear to be formed in an equal molar ratio to each other.

Briefly, on day 1, approximately $5\times10^4$ 293GP$^{SD}$ cells were placed in a 75 cm$^2$ tissue culture flask. On the following day (day 2), the 293GP$^{SD}$ cells were transfected with 25 µg of pLNBOTDC plasmid DNA and 25 µg of VSV-G plasmid DNA using the standard calcium phosphate co-precipitation procedure (Graham and Van der Eb, Virol. 52:456 [1973]). A range of 10 to 40 µg of plasmid DNA may be used. Because 293GP$^{SD}$ cells may take more than 24 hours to attach firmly to tissue culture plates, the 293GP$^{SD}$ cells may be placed in 75 cm$^2$ flasks 48 hours prior to transfection. The transfected 293GP$^{SD}$ cells provide pseudotyped LNBOTDC virus.

On day 3, approximately $1\times10^5$ 293GP$^{SD}$ cells were placed in a 75 cm$^2$ tissue culture flask 24 hours prior to the harvest of the pseudotyped virus from the transfected 293GP$^{SD}$ cells. On day 4, culture medium was harvested from the transfected 293GP$^{SD}$ cells 48 hours after the application of the pLNBOTDC and VSV-G DNA. The culture medium was filtered through a 0.45 µm filter and polybrene was added to a final concentration of 8 µg/ml. The culture medium containing LNBOTDC virus was used to infect the 293GP$^{SD}$ cells as follows. The culture medium was removed from the 293GP$^{SD}$ cells and was replaced with the LNBOTDC virus containing culture medium. Polybrene was added to the medium following addition to cells. The virus containing medium was allowed to remain on the 293GP$^{SD}$ cells for 24 hours. Following the 16 hour infection period (on day 5), the medium was removed from the 293GP$^{SD}$ cells and was replaced with fresh medium containing 400 µg/ml G418 (GIBCO/BRL). The medium was changed approximately every 3 days until G418-resistant colonies appeared approximately two weeks later.

The G418-resistant 293 colonies were plated as single cells in 96 wells. Sixty to one hundred G418-resistant colonies were screened for the expression of the BOTDC antibody in order to identify high producing clones. The top 10 clones in 96-well plates were transferred 6-well plates and allowed to grow to confluency.

The top 10 clones were then expanded to screen for high titer production. Based on protein expression and titer production, 5 clonal cell lines were selected. One line was designated the master cell bank and the other 4 as backup cell lines. Pseudotyped vector was generated as follows. Approximately $1\times10^6$ 293GP$^{SD}$/LNBOTDC cells were placed into a 75 cm$^2$ tissue culture flask. Twenty-four hours later, the cells were transfected with 25 µg of pHCMV-G plasmid DNA using calcium phosphate co-precipitation. Six to eight hours after the calcium-DNA precipitate was applied to the cells, the DNA solution was replaced with fresh culture medium (lacking G418). Longer transfection times (overnight) were found to result in the detachment of the majority of the 293GP$^{SD}$/LNBOTDC cells from the plate and are therefore avoided. The transfected $293GP^{SD}$/LN-BOTDC cells produce pseudotyped LNBOTDC virus.

The pseudotyped LNBOTDC virus generated from the transfected $293GP^{SD}$/LNBOTDC cells can be collected at least once a day between 24 and 96 hr after transfection. The highest virus titer was generated approximately 48 to 72 hr after initial pHCMV-G transfection. While syncytium formation became visible about 48 hr after transfection in the majority of the transfected cells, the cells continued to generate pseudotyped virus for at least an additional 48 hr as long as the cells remained attached to the tissue culture plate. The collected culture medium containing the VSV G-pseudotyped LNBOTDC virus was pooled, filtered through a 0.45 μm filter and stored at −80° C. or concentrated immediately and then stored at −80° C.

The titer of the VSV G-pseudotyped LNBOTDC virus was then determined as follows. Approximately $5\times10^4$ rat 208F fibroblasts cells were plated into 6 well plates. Twenty-fours hours after plating, the cells were infected with serial dilutions of the LNBOTDC virus-containing culture medium in the presence of 8 μg/ml polybrene. Twenty four hours after infection with virus, the medium was replaced with fresh medium containing 400 μg/ml G418 and selection was continued for 14 days until G418-resistant colonies became visible. Viral titers were typically about 0.5 to $5.0\times10^6$ colony forming units (cfu)/ml. The titer of the virus stock could be concentrated to a titer of greater than $10^9$ cfu/ml as described below.

EXAMPLE 4

Concentration of Pseudotyped Retroviral Vectors

The VSV G-pseudotyped LNBOTDC viruses were concentrated to a high titer by one cycle of ultracentrifugation. However, two cycles can be performed for further concentration. The frozen culture medium collected as described in Example 2 which contained pseudotyped LNBOTDC virus was thawed in a 37° C. water bath and was then transferred to Oakridge centrifuge tubes (50 ml Oakridge tubes with sealing caps, Nalge Nunc International) previously sterilized by autoclaving. The virus was sedimented in a JA20 rotor (Beckman) at 48,000×g (20,000 rpm) at 4° C. for 120 min. The culture medium was then removed from the tubes in a biosafety hood and the media remaining in the tubes was aspirated to remove the supernatent. The virus pellet was resuspended to 0.5 to 1% of the original volume of culture medium DMEM. The resuspended virus pellet was incubated overnight at 4° C. without swirling. The virus pellet could be dispersed with gentle pipetting after the overnight incubation without significant loss of infectious virus. The titer of the virus stock was routinely increased 100- to 300-fold after one round of ultracentrifugation. The efficiency of recovery of infectious virus varied between 30 and 100%.

The virus stock was then subjected to low speed centrifugation in a microfuge for 5 min at 4° C. to remove any visible cell debris or aggregated virions that were not resuspended under the above conditions. It was noted that if the virus stock is not to be used for injection into oocytes or embryos, this centrifugation step may be omitted.

The virus stock can be subjected to another round of ultracentrifugation to further concentrate the virus stock. The resuspended virus from the first round of centrifugation is pooled and pelleted by a second round of ultracentrifugation which is performed as described above. Viral titers are increased approximately 2000-fold after the second round of ultracentrifugation (titers of the pseudotyped LNBOTDC virus are typically greater than or equal to $1\times10^9$ cfu/ml after the second round of ultracentrifugation).

The titers of the pre- and post-centrifugation fluids were determined by infection of 208F cells (NIH 3T3 or bovine mammary epithelial cells can also be employed) followed by selection of G418-resistant colonies as described above in Example 2.

EXAMPLE 5

Preparation of Pseudotyped Retrovirus For Infection of Host Cells

The concentrated pseudotyped retroviruses were resuspended in 0.1×HBS (2.5 mM HEPES, pH 7.12, 14 mM NaCl, 75 μM $Na_2HPO_4.H_2O$) and 18 μl aliquots were placed in 0.5 ml vials (Eppendorf) and stored at −80° C. until used. The titer of the concentrated vector was determined by diluting 1 μl of the concentrated virus $10^{-7}$- or $10^{-8}$-fold with 0.1×HBS. The diluted virus solution was then used to infect 208F and bovine mammary epithelial cells and viral titers were determined as described in Example 2.

EXAMPLE 6

Expression of MN14 by Host Cells

This Example describes the production of antibody MN14 from cells transfected with a high number of integrating vectors. Pseudotyped vector were made from the packaging cell lines for the following vectors: CMV MN14, α-LA MN14, and MMTV MN14. Rat fibroblasts (208F cells), MDBK cells (bovine kidney cells), and bovine mammary epithelial cells were transfected at a multiplicity of infection of 1000. One thousand cells were plated in a T25 flask and $10^6$ colony forming units (CFU's) of vector in 3 ml media was incubated with the cells. The duration of the infection was 24 hr, followed by a media change. Following transfection, the cells were allowed to grow and become confluent.

The cell lines were grown to confluency in T25 flasks and 5 ml of media was changed daily. The media was assayed daily for the presence of MN14. All of the MN14 produced is active (an ELISA to detect human IgG gave the exact same values as the CEA binding ELISA) and Western blotting has shown that the heavy and light chains are produced at a ratio that appears to be a 1:1 ratio. In addition, a non-denaturing Western blot indicated that what appeared to be 100% of the antibody complexes were correctly formed (See FIG. 1: Lane 1, 85 ng control Mn14; Lane 2, bovine mammary cell line, α-LA promoter; Lane 3, bovine mammary cell line, CMV promoter; Lane 4, bovine kidney cell line, α-LA promoter; Lane 5, bovine kidney cell line, CMV promoter; Lane 6, 208 cell line, α-LA promoter; Lane 7, 208 cell line, CMV promoter)).

FIG. 2 is a graph showing the production of MN14 over time for four cell lines. The Y axis shows MN14 production in ng/ml of media. The X-axis shows the day of media collection for the experiment. Four sets of data are shown on the graph. The comparisons are between the CMV and α-LA promoter and between the 208 cells and the bovine mammary cells. The bovine mammary cell line exhibited the highest expression, followed by the 208F cells and MDBK cells. With respect to the constructs, the CMV driven construct demonstrated the highest level of expression, followed by the α-LA driven gene construct and the MMTV construct. At 2 weeks, the level of daily production of the CMV construct was 4.5 µg/ml of media (22.5 mg/day in a T25 flask). The level of expression subsequently increased slowly to 40 µg/day as the cells became very densely confluent over the subsequent week. 2.7 L of media from an α-lac-MN14 packaging cell line was processed by affinity chromatography to produce a purified stock of MN14.

Figure 3:
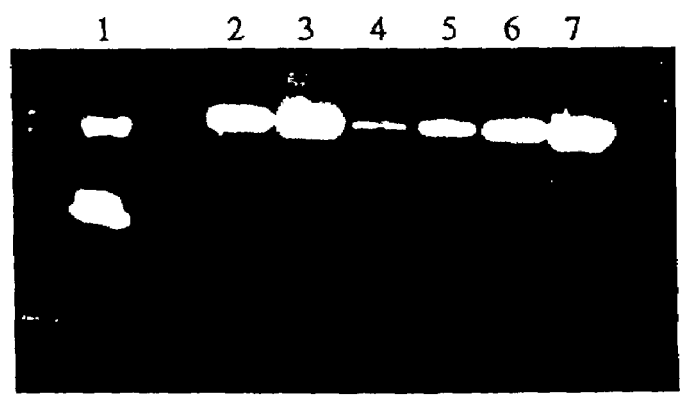
FIG. 3 is a Western blot of a 15% PAGE run under non-denaturing conditions and probed with anti-human IgG (Fc) and anti-human IgG (Kappa).

FIG. 3 is a western blot of a 15% SDS-PAGE gel run under denaturing conditions in order to separate the heavy and light chains of the MN14 antibody. Lane 1 shows MN14 from bovine mammary cell line, hybrid α-LA promoter; lane 2 shows MN14 from bovine mammary cell line, CMV promoter; lane 3 shows MN14 from bovine kidney cell line, hybrid αLA promoter; lane 4 shows MN14 from bovine kidney cell line, CMV promoter; lane 5 shows MN14 from rat fibroblast cell line, hybrid α-LA promoter; lane 6 shows MN14 from rat fibroblast, CMV promoter. In agreement with FIG. 1 above, the results show that the heavy and light chains are produced in a ratio of approximately 1:1.

EXAMPLE 7

Quantitation of Protein Produced Per Cell

This Example describes the quantitation of the amount of protein produced per cell in cell cultures produced according to the invention. Various cells (208F cells, MDBK cells, and bovine mammary cells) were plated in 25 cm² culture dishes at 1000 cells/dish. Three different vectors were used to infect the three cells types (CMV-MN14, MMTV-MN14, and α-LA-MN14) at an MOI of 1000 (titers: $2.8 \times 10^6$, $4.9 \times 10^6$, and $4.3 \times 10^6$, respectively). Media was collected approximately every 24 hours from all cells. Following one month of media collection, the 208F and MDBK cells were discarded due to poor health and low MN14 expression. The cells were passaged to T25 flasks and collection of media from the bovine mammary cells was continued for approximately 2 months with continued expression of MN14. After two months in T25 flasks, the cells with CMV promoters were producing 22.5 pg/cell/day and the cells with α-LA promoters were producing 2.5 pg MN14/cell/day.

After 2 months in T25 flasks, roller bottles (850 cm²) were seeded to scale-up production and to determine if MN14 expression was stable following multiple passages. Two roller bottles were seeded with bovine mammary cells expressing MN14 from a CMV promoter and two roller bottles were seeded with bovine mammary cells expressing MN14 from the α-LA promoter. The cultures reached confluency after approximately two weeks and continue to express MN14. Roller bottle expression is shown in Table 1 below.

TABLE 1

Production of MN14 in Roller Bottles

| Cell Line | Promoter | MN14 Production/ Week (µg/ml) | MN14 Production/ Week - Total (µg/ml) |
|---|---|---|---|
| Bovine mammary | CMV | 2.6 | 1 - 520 |
| Bovine mammary | CMV | 10.6 | 2 - 2120 |
| Bovine mammary | CMV | 8.7 | 3 - 1740 |
| Bovine mammary | CMV | 7.8 | 4 - 1560 |

TABLE 1-continued

Production of MN14 in Roller Bottles

| Cell Line | Promoter | MN14 Production/ Week (µg/ml) | MN14 Production/ Week - Total (µg/ml) |
|---|---|---|---|
| Bovine mammary | α-LA | 0.272 | 1 - 54.4 |
| Bovine mammary | α-LA | 2.8 | 2 - 560 |
| Bovine mammary | α-LA | 2.2 | 3 - 440 |
| Bovine mammary | α-LA | 2.3 | 4 - 460 |

EXAMPLE 8

Expression of LL2 Antibody

This Example demonstrates the expression of antibody LL2 by bovine mammary cells and 293 human kidney fibroblast cells. Bovine mammary cells were infected with vector CMV LL2 ($7.85 \times 10^7$ CFU/ml) at MOI's of 1000 and 10,000 and plated in 25 cm² culture dishes. None of the cells survived transfection at the MOI of 10,000. At 20% confluency, 250 ng/ml of LL2 was present in the media. Active LL2 antibody was produced by both cell types. Non-denaturing and denaturing western analysis demonstrated that all the antibody produced is active and correctly assembled in approximately a 1:1 ratio of heavy:light chain.

EXAMPLE 9

Expression of Bot Antibody by Bovine Mammary Cells

This Example demonstrates the expression of botulinum toxin antibody in bovine mammary cells. Bovine mammary cells were infected with vector α-LA Bot ($2.2 \times 10^2$ CFU/ml) and plated in 25 cm² culture dishes. At 100% confluency, 6 ng/ml of botulinum toxin antibody was present in the media.

EXAMPLE 10

Expression of Hepatitis B Surface Antigen by Bovine Mammary Cells

This Example demonstrates the expression of Hepatitis B Surface Antigen antibody in bovine mammary cells. Bovine mammary cells were infected with vector LSRNL (350 CFU/ml) and plated in 25 cm² culture dishes. At 100% confluency, 20 ng/ml of Hepatitis B Surface Antigen was present in the media.

EXAMPLE 11

Expression of cc49IL2 Antigen Binding Protein

This Example demonstrates the expression of cc49IL2 in bovine mammary cells and human kidney fibroblast cells. Bovine mammary cells were infected with vector LSRNL ($3.1 \times 10^5$ CFU/ml) at a MOI of 1000 and plated in 25 cm² culture dishes. At 100% confluency, 10 µg/ml of cc49IL2 was present in the media. Human kidney fibroblast (293 cells were infected with the α-LA cc49IL2 vector. Active cc49-IL2 fusion protein was produced by the cells.

EXAMPLE 12

Production of YP Antibody

This Example demonstrates the production of *Yersinea pestis* antibody by bovine mammary epithelial cells and human kidney fibroblast cells (293 cells). Cells lines were infected with the α-LA YP vector. Both of the cell lines produced YP antibody. All of the antibody is active and the heavy and light chains are produced in a ratio approximating 1:1.

EXAMPLE 13

Expression of Multiple Proteins by Bovine Mammary Cells

This Example demonstrates the expression of multiple proteins in bovine mammary cells. Mammary cells producing MN14 (infected with CMV-MN14 vector) were infected with cc49IL2 vector ($3.1\times10^5$ CFU/ml) at an MOI of 1000, and 1000 cells were plated in 25 $cm^2$ culture plates. At 100% confluency, the cells expressed MN14 at 2.5 μg/ml and cc49IL2 at 5 μg/ml.

EXAMPLE 14

Expression of Multiple Proteins by Bovine Mammary Cells

This Example demonstrates the expression of multiple proteins in bovine mammary cells. Mammary cells producing MN14 (infected with CMV-MN14 vector) were infected with LSNRL vector (100 CFU/ml) at an MOI of 1000, and 1000 cells were plated in 25 $cm^2$ culture plates. At 100% confluency, the cells expressed MN14 at 2.5 μg/ml and hepatitis surface antigen at 150 ng/ml.

EXAMPLE 15

Expression of Multiple Proteins by Bovine Mammary Cells

This Example demonstrates the expression of multiple proteins in bovine mammary cells. Mammary cells producing hepatitis B surface antigen (infected with LSRNL vector) were infected with cc49IL2 vector at an MOI of 1000, and 1000 cells were plated in 25 $cm^2$ culture plates. At 100% confluency, the cells expressed MN14 at 2.4 and hepatitis B surface antigen at 13.

EXAMPLE 16

Expression of Hepatitis B Surface Antigen and Bot Antibody in Bovine Mammary Cells This Example demonstrates the culture of transfected cells in roller bottle cultures. 208F cells and bovine mammary cells were plated in 25 $cm^2$ culture dishes at 1000 cells/25 $cm^2$. LSRNL or α-LA Bot vectors were used to infect each cell line at a MOI of 1000. Following one month of culture and media collection, the 208F cells were discarded due to poor growth and plating. Likewise, the bovine mammary cells infected with α-LA Bot were discarded due to low protein expression. The bovine mammary cells infected with LSRNL were passaged to seed roller bottles (850 $cm^2$). Approximately 20 ng/ml hepatitis type B surface antigen was produced in the roller bottle cultures.

EXAMPLE 17

Expression and Assay of G-protein Coupled Receptors

This example describes the expression of a G-Protein Coupled Receptor protein (GPCR) from a retroviral vector. This example also describes the expression of a signal protein from an IRES as a marker for expression of a difficult to assay protein or a protein that has no assay such as a GPCR. The gene construct (SEQ ID NO: 34; FIG. 17) comprises a G-protein-coupled receptor followed by the IRES-signal peptide-antibody light chain cloned into the MCS of pLBCX retroviral backbone. Briefly, a PvuII/PvuII fragment (3057 bp) containing the GPCR-IRES-antibody light chain was cloned into the StuI site of pLBCX. pLBCX contains the EM7 (T7) promoter, Blasticidin gene and SV40 polyA in place of the Neomycin resistance gene from pLNCX.

The gene construct was used to produce a replication defective retroviral packaging cell line and this cell line was used to produce replication defective retroviral vector. The vector produced from this cell line was then used to infect 293GP cells (human embryonic kidney cells). After infection, the cells were placed under Blasticidin selection and single cell Blasticidin resistant clones were isolated. The clones were screened for expression of antibody light chain. The top 12 light chain expressing clones were selected. These 12 light chain expressing clones were then screened for expression of the GPCR using a ligand binding assay. All twelve of the samples also expressed the receptor protein. The clonal cell lines and there expression are shown in Table 2.

TABLE 2

| Cell Clone Number | Antibody Light Chain Expression | GPCR Expression |
|---|---|---|
| 4 | + | + |
| 8 | + | + |
| 13 | + | + |
| 19 | + | + |
| 20 | + | + |
| 22 | + | + |
| 24 | + | + |
| 27 | + | + |
| 30 | + | + |
| 45 | + | + |
| 46 | + | + |
| 50 | + | + |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, protein fermentation, biochemistry, or related fields are intended to be within the scope of the following claims.

What is claimed is:

1. A vector comprising a nucleic acid sequence selected from the group consisting of SEQ ID NO:2 and variants of SEQ ID NO:2, wherein said variants are identical to SEQ ID NO:2 with the exception that positions 4, 112, and 238 of said variant of SEQ ID NO:2 are not guanine, and wherein said nucleic acid sequence facilitates high levels of expression of proteins without the need for incorporating introns into nucleic acids encoding said proteins.

2. The vector of claim 1, wherein said vector is a retroviral vector.

3. An isolated host cell comprising the vector of claim 1.

4. The vector of claim 1, wherein said vector comprises multiple copies of said nucleic acid sequence.

* * * * *

SEQUENCE LISTING

<160> NUMBER OF SEQ ID NOS: 36

<210> SEQ ID NO 1
<211> LENGTH: 2101
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| gatcagtcct | gggtggtcat | tgaaaggact | gatgctgaag | ttgaagctcc | aatactttgg | 60 |
| ccacctgatg | cgaagaactg | actcatgtga | taagaccctg | atactgggaa | agattgaagg | 120 |
| caggaggaga | agggatgaca | gaggatggaa | gagttggatg | gaatcaccaa | ctcgatggac | 180 |
| atgagtttga | gcaagcttcc | aggagttggt | aatgggcagg | gaagcctggc | gtgctgcagt | 240 |
| ccatggggtt | gcaaagagtt | ggacactact | gagtgactga | actgaactga | tagtgtaatc | 300 |
| catggtacag | aatataggat | aaaaaagagg | aagagtttgc | cctgattctg | aagagttgta | 360 |
| ggatataaaa | gtttagaata | cctttagttt | ggaagtctta | aattatttac | ttaggatggg | 420 |
| tacccactgc | aatataagaa | atcaggcttt | agagactgat | gtagagagaa | tgagccctgg | 480 |
| cataccagaa | gctaacagct | attggttata | gctgttataa | ccaatatata | accaatatat | 540 |
| tggttatata | gcatgaagct | tgatgccagc | aatttgaagg | aaccatttag | aactagtatc | 600 |
| ctaaactcta | catgttccag | gacactgatc | ttaaagctca | ggttcagaat | cttgttttat | 660 |
| aggctctagg | tgtatattgt | ggggcttccc | tggtggctca | gatggtaaag | tgtctgcctg | 720 |
| caatgtgggt | gatctgggtt | cgatccctgg | cttgggaaga | tccctggag | aaggaaatgg | 780 |
| caacccactc | tagtactctt | acctggaaaa | ttccatggac | agaggagcct | tgtaagctac | 840 |
| agtccatggg | attgcaaaga | gttgaacaca | actgagcaac | taagcacagc | acagtacagt | 900 |
| atacacctgt | gaggtgaagt | gaagtgaagg | ttcaatgcag | ggtctcctgc | attgcagaaa | 960 |
| gattctttac | catctgagcc | accagggaag | cccaagaata | ctggagtggg | tagcctattc | 1020 |
| cttctccagg | ggatcttccc | atcccaggaa | ttgaactgga | gtctcctgca | tttcaggtgg | 1080 |
| attcttcacc | agctgaacta | ccaggtggat | actactccaa | tattaaagtg | cttaaagtcc | 1140 |
| agttttccca | cctttcccaa | aaaggttggg | tcactctttt | ttaaccttct | gtggcctact | 1200 |
| ctgaggctgt | ctacaagctt | atatatttat | gaacacattt | attgcaagtt | gttagtttta | 1260 |
| gatttacaat | gtggtatctg | gctatttagt | ggtattggtg | gttggggatg | gggaggctga | 1320 |
| tagcatctca | gagggcagct | agatactgtc | atacacactt | ttcaagttct | ccattttgt | 1380 |
| gaaatagaaa | gtctctggat | ctaagttata | tgtgattctc | agtctctgtg | gtcatattct | 1440 |
| attctactcc | tgaccactca | acaaggaacc | aagatatcaa | gggacacttg | ttttgtttca | 1500 |
| tgcctgggtt | gagtgggcca | tgacatatgt | tctgggcctt | gttacatggc | tggattggtt | 1560 |
| ggacaagtgc | cagctctgat | cctgggactg | tggcatgtga | tgacatacac | cccctctcca | 1620 |
| cattctgcat | gtctctaggg | gggaaggggg | aagctcggta | tagaaccttt | attgtatttt | 1680 |
| ctgattgcct | cacttcttat | attgcccccca | tgcccttctt | tgttcctcaa | gtaaccagag | 1740 |
| acagtgcttc | ccagaaccaa | ccctacaaga | aacaaaggc | taaacaaagc | caaatggaa | 1800 |
| gcaggatcat | ggtttgaact | cttctctggcc | agagaacaat | acctgctatg | gactagatac | 1860 |
| tgggagaggg | aaaggaaaag | tagggtgaat | tatggaagga | agctggcagg | ctcagcgttt | 1920 |
| ctgtcttggc | atgaccagtc | tctcttcatt | ctcttcctag | atgtagggct | tggtaccaga | 1980 |

```
gcccctgagg ctttctgcat gaatataaat atatgaaact gagtgatgct tccatttcag    2040
gttcttgggg gcgccgaatt cgagctcggt acccggggat ctcgagggggg ggcccggtac    2100 c                                                                      2101

<210> SEQ ID NO 2
<211> LENGTH: 245
<212> TYPE: DNA
<213> ORGANISM: Artificial Sequence
<220> FEATURE:
<223> OTHER INFORMATION: Synthetic

<400> SEQUENCE: 2
gattacttac tggcaggtgc tgggggcttc cgagacaatc gcgaacatct acaccacaca      60
acaccgcctc gaccagggtg agatatcggc cggggacgcg gcggtggtaa ttacaagcga     120
ggatccgatt acttactggc aggtgctggg ggcttccgag acaatcgcga acatctacac     180
cacacaacac cgcctcgacc agggtgagat atcggccggg gacgcggcgg tggtaattac     240
aagcg                                                                 245

<210> SEQ ID NO 3
<211> LENGTH: 680
<212> TYPE: DNA
<213> ORGANISM: Artificial Sequence
<220> FEATURE:
<223> OTHER INFORMATION: Synthetic

<400> SEQUENCE: 3
ggaattcgcc cctctccctc cccccccct aacgttactg gccgaagccg cttggaataa       60
ggccggtgtg cgtttgtcta tatgttattt tccaccatat tgccgtcttt tggcaatgtg     120
agggcccgga aacctggccc tgtcttcttg acgagcattc ctaggggtct ttcccctctc     180
gccaaaggaa tgcaaggtct gttgaatgtc gtgaaggaag cagttcctct ggaagcttct     240
tgaagacaaa caacgtctgt agcgaccctt tgcaggcagc ggaaccccc  acctggcgac     300 aggtgcctct gcggccaaaa gccacgtgta taagatacac ctgcaaaggc ggcacaaccc     360
cagtgccacg ttgtgagttg atagttgtg  gaaagagtca atggctctc  ctcaagcgta     420 ttcaacaagg ggctgaagga tgcccagaag gtacccccatt gtatgggatc tgatctgggg     480
cctcggtgca catgctttac atgtgtttag tcgaggttaa aaaaacgtct aggccccccg     540
aaccacgggg acgtggtttt cctttgaaaa acacgatgat aatatggcct ctttgtctc      600 tctgctcctg gtaggcatcc tattccatgc cacccaggcc ggcgccatgg gatatctaga     660
tctcgagctc gcgaaagctt                                                 680

<210> SEQ ID NO 4
<211> LENGTH: 4207
<212> TYPE: DNA
<213> ORGANISM: Artificial Sequence
<220> FEATURE:
<223> OTHER INFORMATION: Synthetic

<400> SEQUENCE: 4
cggatccggc cattagccat attattcatt ggttatatag cataaatcaa tattggctat       60
tggccattgc atacgttgta tccatatcat aatatgtaca tttatattgg ctcatgtcca     120
acattaccgc catgttgaca ttgattattg actagttatt aatagtaatc aattacgggg     180
tcattagttc atagcccata tatggagttc cgcgttacat aacttacggt aaatggcccg     240
```

```
cctggctgac cgcccaacga cccccgccca ttgacgtcaa taatgacgta tgttcccata    300
gtaacgccaa tagggacttt ccattgacgt caatgggtgg agtatttacg gtaaactgcc    360
cacttggcag tacatcaagt gtatcatatg ccaagtacgc ccctattga cgtcaatgac     420 ggtaaatggc ccgcctggca ttatgcccag tacatgacct tatgggactt tcctacttgg    480
cagtacatct acgtattagt catcgctatt accatggtga tgcggttttg gcagtacatc    540
aatgggcgtg gatagcggtt tgactcacgg ggatttccaa gtctccaccc cattgacgtc    600
aatgggagtt tgttttggca ccaaaatcaa cgggactttc caaaatgtcg taacaactcc    660
gccccattga cgcaaatggg cggtaggcat gtacggtggg aggtctatat aagcagagct    720
cgtttagtga accgtcagat cgcctggaga cgccatccac gctgttttga cctccataga    780
agacaccggg accgatccag cctccgcggc cccaagcttc tcgacggatc cccgggaatt    840
caggacctca ccatgggatg gagctgtatc atcctcttct tggtagcaac agctacaggt    900
gtccactccg aggtccaact ggtggagagc ggtggaggtg ttgtgcaacc tggccggtcc    960
ctgcgcctgt cctgctccgc atctggcttc gatttcacca catattggat gagttgggtg    1020
agacaggcac ctggaaaagg tcttgagtgg attggagaaa ttcatccaga tagcagtacg    1080
attaactatg cgccgtctct aaaggataga tttacaatat cgcgagacaa cgccaagaac    1140
acattgttcc tgcaaatgga cagcctgaga cccgaagaca ccggggtcta ttttgtgca     1200 agcctttact tcggcttccc ctggtttgct tattggggcc aagggacccc ggtcaccgtc    1260
tcctcagcct ccaccaaggg cccatcggtc ttccccctgg cacccctcc caagagcacc     1320 tctgggggca gcggccct gggctgcctg gtcaaggact acttccccga accggtgacg      1380
gtgtcgtgga actcaggcgc cctgaccagc ggcgtgcaca ccttcccggc tgtcctacag    1440
tcctcaggac tctactccct cagcagcgtg gtgaccgtgc cctccagcag cttgggcacc    1500
cagacctaca tctgcaacgt gaatcacaag cccagcaaca ccaaggtgga caagagagtt    1560
gagcccaaat cttgtgacaa aactcacaca tgcccaccgt gcccagcacc tgaactcctg    1620
gggggaccgt cagtcttcct cttccccca aaacccaagg acaccctcat gatctcccgg     1680 accccctgagg tcacatgcgt ggtggtggac gtgagccacg aagaccctga ggtcaagttc    1740
aactggtacg tggacggcgt ggaggtgcat aatgccaaga caaagccgcg ggaggagcag    1800
tacaacagca cgtaccgtgt ggtcagcgtc ctcaccgtcc tgcaccagga ctggctgaat    1860
ggcaaggagt acaagtgcaa ggtctccaac aaagccctcc cagcccccat cgagaaaacc    1920
atctccaaag ccaaagggca gccccgagaa ccacaggtgt acaccctgcc cccatcccgg    1980
gaggagatga ccaagaacca ggtcagcctg acctgcctgg tcaaaggctt ctatcccagc    2040
gacatcgccg tggagtggga gagcaatggg cagccggaga caactacaa gaccacgcct     2100 cccgtgctgg actccgacgg ctccttcttc ctctatagca agctcaccgt ggacaagagc    2160
aggtggcagc aggggaacgt cttctcatgc tccgtgatgc acgaggctct gcacaaccac    2220
tacacgcaga gagcctctc cctgtctccc gggaaatgaa agccgaattc gcccctctcc     2280 ctccccccc cctaacgtta ctggccgaag ccgcttggaa taaggccggt gtgcgtttgt     2340
ctatatgtta ttttccacca tattgccgtc ttttggcaat gtgagggccc ggaaacctgg    2400
ccctgtcttc ttgacgagca ttcctagggg tctttcccct ctcgccaaag gaatgcaagg    2460
tctgttgaat gtcgtgaagg aagcagttcc tctggaagct tcttgaagac aaacaacgtc    2520
tgtagcgacc ctttgcaggc agcggaaccc cccacctggc gacaggtgcc tctgcggcca    2580
aaagccacgt gtataagata cacctgcaaa ggcggcacaa ccccagtgcc acgttgtgag    2640
```

```
ttggatagtt gtggaaagag tcaaatggct ctcctcaagc gtattcaaca aggggctgaa    2700
ggatgcccag aagtacccc attgtatggg atctgatctg gggcctcggt gcacatgctt     2760
tacatgtgtt tagtcgaggt taaaaaaacg tctaggcccc ccgaaccacg gggacgtggt    2820
tttcctttga aaacacgat gataatatgg cctcctttgt ctctctgctc ctggtaggca     2880
tcctattcca tgccacccag gccgacatcc agctgaccca gagcccaagc agcctgagcg    2940
ccagcgtggg tgacagagtg accatcacct gtaaggccag tcaggatgtg ggtacttctg    3000
tagcctggta ccagcagaag ccaggtaagg ctccaaagct gctgatctac tggacatcca    3060
cccggcacac tggtgtgcca agcagattca gcggtagcgg tagcggtacc gacttcacct    3120
tcaccatcag cagcctccag ccagaggaca tcgccaccta ctactgccag caatatagcc    3180
tctatcggtc gttcggccaa gggaccaagg tggaaatcaa acgaactgtg ctgcaccat     3240 ctgtcttcat cttcccgcca tctgatgagc agttgaaatc tggaactgcc tctgttgtgt    3300
gcctgctgaa taacttctat cccagagagg ccaaagtaca gtggaaggtg gataacgccc    3360
tccaatcggg taactcccag gagagtgtca cagagcagga cagcaaggac agcacctaca    3420
gcctcagcag caccctgacg ctgagcaaag cagactacga gaaacacaaa gtctacgcct    3480
gcgaagtcac ccatcagggc ctgagctcgc ccgtcacaaa gagcttcaac aggggagagt    3540
gttagagatc taggcctcct aggtcgacat cgataaaata aaagatttta tttagtctcc    3600
agaaaaaggg gggaatgaaa gaccccacct gtaggtttgg caagctagct taagtaacgc    3660
cattttgcaa ggcatggaaa atacataac tgagaataga gaagttcaga tcaaggtcag    3720
gaacagatgg aacagctgaa tatgggccaa acaggatatc tgtggtaagc agttcctgcc    3780
ccggctcagg gccaagaaca gatggaacag ctgaatatgg ccaaacagg atatctgtgg    3840 taagcagttc ctgccccggc tcagggccaa gaacagatgg tccccagatg cggtccagcc    3900
ctcagcagtt tctagagaac catcagatgt ttccagggtg ccccaaggac ctgaaatgac    3960
cctgtgcctt atttgaacta accaatcagt tcgcttctcg cttctgttcg cgcgcttctg    4020
ctccccgagc tcaataaaag agcccacaac ccctcactcg gggcgccagt cctccgattg    4080
actgagtcgc ccgggtaccc gtgtatccaa taaaccctct tgcagttgca tccgacttgt    4140
ggtctcgctg ttccttggga gggtctcctc tgagtgattg actacccgtc agcggggtc    4200 tttcatt                                                              4207
```

<210> SEQ ID NO 5
<211> LENGTH: 4210
<212> TYPE: DNA
<213> ORGANISM: Artificial Sequence
<220> FEATURE:
<223> OTHER INFORMATION: Synthetic

<400> SEQUENCE: 5

```
ggatccggcc attagccata ttattcattg gttatatagc ataaatcaat attggctatt    60
ggccattgca tacgttgtat ccatatcata atatgtacat ttatattggc tcatgtccaa    120
cattaccgcc atgttgacat tgattattga ctagttatta atagtaatca attacggggt    180
cattagttca tagcccatat atggagttcc gcgttacata acttacggta aatggcccgc    240
ctggctgacc gcccaacgac ccccgcccat tgacgtcaat aatgacgtat gttcccatag    300
taacgccaat agggactttc cattgacgtc aatgggtgga gtatttacgg taaactgccc    360
acttggcagt acatcaagtg tatcatatgc caagtacgcc ccctattgac gtcaatgacg    420
```

```
gtaaatggcc cgcctggcat tatgcccagt acatgacctt atgggacttt cctacttggc      480
agtacatcta cgtattagtc atcgctatta ccatggtgat gcggttttgg cagtacatca      540
atgggcgtgg atagcggttt gactcacggg gatttccaag tctccacccc attgacgtca      600
atgggagttt gttttggcac caaaatcaac gggactttcc aaaatgtcgt aacaactccg      660
ccccattgac gcaaatgggc ggtaggcatg tacggtggga ggtctatata agcagagctc      720
gtttagtgaa ccgtcagatc gcctggagac gccatccacg ctgttttgac ctccatagaa      780
gacaccggga ccgatccagc ctccgcggcc ccaagcttct cgacggatcc ccgggaattc      840
aggacctcac catgggatgg agctgtatca tcctcttctt ggtagcaaca gctacaggtg      900
tccactccca ggtccagctg gtccaatcag gggctgaagt caagaaacct gggtcatcag      960
tgaaggtctc ctgcaaggct tctggctaca ccttactag ctactggctg cactgggtca     1020
ggcaggcacc tggacagggt ctggaatgga ttggatacat taatcctagg aatgattata     1080
ctgagtacaa tcagaacttc aaggacaagg ccacaataac tgcagacgaa tccaccaata     1140
cagcctacat ggagctgagc agcctgaggt ctgaggacac ggcattttat ttttgtgcaa     1200
gaagggatat tactacgttc tactggggcc aaggcaccac ggtcaccgtc tcctcagcct     1260
ccaccaaggg cccatcggtc ttccccctgg caccctcctc caagagcacc tctggggca      1320 cagcggccct gggctgcctg gtcaaggact acttccccga accggtgacg gtgtcgtgga     1380
actcaggcgc cctgaccagc ggcgtgcaca ccttcccggc tgtcctacag tcctcaggac     1440
tctactccct cagcagcgtg gtgaccgtgc cctccagcag cttgggcacc cagacctaca     1500
tctgcaacgt gaatcacaag cccagcaaca ccaaggtgga caagagagtt gagcccaaat     1560
cttgtgacaa aactcacaca tgcccaccgt gcccagcacc tgaactcctg ggggaccgt      1620 cagtcttcct cttccccca aaacccaagg acaccctcat gatctcccgg acccctgagg     1680
tcacatgcgt ggtggtggac gtgagccacg aagaccctga ggtcaagttc aactggtacg     1740
tggacggcgt ggaggtgcat aatgccaaga caaagccgcg ggaggagcag tacaacagca     1800
cgtaccgtgt ggtcagcgtc ctcaccgtcc tgcaccagga ctggctgaat ggcaaggagt     1860
acaagtgcaa ggtctccaac aaagccctcc cagcccccat cgagaaaacc atctccaaag     1920
ccaaagggca gccccgagaa ccacaggtgt acaccctgcc cccatcccgg gaggagatga     1980
ccaagaacca ggtcagcctg acctgcctgg tcaaaggctt ctatcccagc gacatcgccg     2040
tggagtggga gagcaatggg cagccggaga acaactacaa gaccacgcct cccgtgctgg     2100
actccgacgg ctccttcttc ctctatagca agctcaccgt ggacaagagc aggtggcagc     2160
aggggaacgt cttctcatgc tccgtgatgc acgaggctct gcacaaccac tacacgcaga     2220
agagcctctc cctgtctccc gggaaatgaa agccgaattc gccctctcc ctcccccccc     2280 cctaacgtta ctggccgaag ccgcttggaa taaggccggt gtgcgtttgt ctatatgtta     2340
ttttccacca tattgccgtc ttttggcaat gtgagggccc ggaaacctgg ccctgtcttc     2400
ttgacgagca ttcctagggg tctttcccct ctcgccaaag gaatgcaagg tctgttgaat     2460
gtcgtgaagg aagcagttcc tctggaagct tcttgaagac aaacaacgtc tgtagcgacc     2520
ctttgcaggc agcggaaccc cccacctggc gacaggtgcc tctgcggcca aaagccacgt     2580
gtataagata cacctgcaaa ggcggcacaa ccccagtgcc acgttgtgag ttggatagtt     2640
gtggaaagag tcaaatggct ctcctcaagc gtattcaaca aggggctgaa ggatgcccag     2700
aaggtacccc attgtatggg atctgatctg gggcctcggt gcacatgctt acatgtgttt     2760
tagtcgaggt taaaaaaacg tctaggcccc ccgaaccacg gggacgtggt tttcctttga     2820
```

```
aaaacacgat gataatatgg cctcctttgt ctctctgctc ctggtaggca tcctattcca    2880
tgccacccag gccgacatcc agctgaccca gtctccatca tctctgagcg catctgttgg    2940
agatagggtc actatgagct gtaagtccag tcaaagtgtt ttatacagtg caaatcacaa    3000
gaactacttg gcctggtacc agcagaaacc agggaaagca cctaaactgc tgatctactg    3060
ggcatccact agggaatctg gtgtcccttc gcgattctct ggcagcggat ctgggacaga    3120
ttttactttc accatcagct ctcttcaacc agaagacatt gcaacatatt attgtcacca    3180
atacctctcc tcgtggacgt tcggtggagg gaccaaggtg cagatcaaac gaactgtggc    3240
tgcaccatct gtcttcatct tcccgccatc tgatgagcag ttgaaatctg gaactgcctc    3300
tgttgtgtgc ctgctgaata acttctatcc cagagaggcc aaagtacagt ggaaggtgga    3360
taacgccctc caatcgggta actcccagga gagtgtcaca gagcaggaca gcaaggacag    3420
cacctacagc ctcagcagca ccctgacgct gagcaaagca gactacgaga aacacaaagt    3480
ctacgcctgc gaagtcaccc atcagggcct gagctcgccc gtcacaaaga gcttcaacag    3540
gggagagtgt tagagatcta ggcctcctag gtcgacatcg ataaaataaa agattttatt    3600
tagtctccag aaaaagggg gaatgaaaga ccccacctgt aggtttggca agctagctta    3660
agtaacgcca ttttgcaagg catggaaaaa tacataactg agaatagaga agttcagatc    3720
aaggtcagga acagatggaa cagctgaata tgggccaaac aggatatctg tggtaagcag    3780
ttcctgcccc ggctcagggc caagaacaga tggaacagct gaatatgggc caaacaggat    3840
atctgtggta agcagttcct gccccggctc agggccaaga acagatggtc ccagatgcg    3900 gtccagccct cagcagtttc tagagaacca tcagatgttt ccagggtgcc caaggacct    3960 gaaatgaccc tgtgccttat ttgaactaac caatcagttc gcttctcgct tctgttcgcg    4020
cgcttctgct ccccgagctc aataaaagag cccacaaccc ctcactcggg gcgccagtcc    4080
tccgattgac tgagtcgccc gggtacccgt gtatccaata aaccctcttg cagttgcatc    4140
cgacttgtgg tctcgctgtt ccttgggagg gtctcctctg agtgattgac tacccgtcag    4200 gtcttttcatt                                                         4210
```

<210> SEQ ID NO 6
<211> LENGTH: 5732
<212> TYPE: DNA
<213> ORGANISM: Artificial Sequence
<220> FEATURE:
<223> OTHER INFORMATION: Synthetic

<400> SEQUENCE: 6

```
cgagcttggc agaaatggtt gaactcccga gagtgtccta cacctagggg agaagcagcc     60
aaggggttgt ttcccaccaa ggacgacccg tctgcgcaca aacggatgag cccatcagac    120
aaagacatat tcattctctg ctgcaaactt ggcatagctc tgctttgcct ggggctattg    180
ggggaagttg cggttcgtgc tcgcagggct ctcacccttg actctttcaa taataactct    240
tctgtgcaag attacaatct aaacaattcg gagaactcga ccttcctcct gaggcaagga    300
ccacagccaa cttcctctta caagccgcat cgattttgtc cttcagaaat agaaataaga    360
atgcttgcta aaaattatat ttttaccaat aagaccaatc caataggtag attattagtt    420
actatgttaa gaaatgaatc attatctttt agtactattt ttactcaaat tcagaagtta    480
gaaatgggaa tagaaaatag aaagagacgc tcaacctcaa ttgaagaaca ggtgcaagga    540
ctattgacca caggcctaga agtaaaaaag ggaaaaaaga gtgttttgt caaaatagga    600
```

```
gacaggtggt ggcaaccagg gacttatagg ggaccttaca tctacagacc aacagatgcc     660
cccttaccat atacaggaag atatgactta aattgggata ggtgggttac agtcaatggc     720
tataaagtgt tatatagatc cctccccttt cgtgaaagac tcgccagagc tagacctcct     780
tggtgtatgt tgtctcaaga aagaaagac gacatgaaac aacaggtaca tgattatatt      840
tatctaggaa caggaatgca cttttgggga aagattttcc ataccaagga ggggacagtg     900
gctggactaa tagaacatta ttctgcaaaa acttatggca tgagttatta tgattagcct     960
tgatttgccc aaccttgcgg ttcccaaggc ttaagtaagt ttttggttac aaactgttct     1020
taaaacaagg atgtgagaca agtggttttcc tgacttggtt tggtatcaaa ggttctgatc    1080
tgagctctga gtgttctatt ttcctatgtt cttttggaat ttatccaaat cttatgtaaa     1140
tgcttatgta aaccaagata taaagagtg ctgatttttt gagtaaactt gcaacagtcc      1200
taacattcac ctcttgtgtg tttgtgtctg ttcgccatcc cgtctccgct cgtcacttat     1260
ccttcacttt ccagagggtc ccccgcaga ccccggcgac cctcaggtcg gccgactgcg      1320
gcagctggcg cccgaacagg gaccctcgga taagtgaccc ttgtctttat ttctactatt     1380
ttgtgttcgt cttgttttgt ctctatcttg tctggctatc atcacaagag cggaacggac     1440
tcacctcagg gaaccaagct agcccggggt cgacggatcc gattacttac tggcaggtgc     1500
tgggggcttc cgagacaatc gcgaacatct acaccacaca acaccgcctc gaccaggtg      1560 agatatcggc cggggacgcg gcggtggtaa ttacaagcga gatccgatta cttactggca     1620
ggtgctgggg gcttccgaga caatcgcgaa catctacacc acacaacacc gcctcgacca     1680
gggtgagata tcggccgggg acgcggcggt ggtaattaca agcgagatcc cgggaattc      1740 aggacctcac catgggatgg agctgtatca tcctcttctt ggtagcaaca gctacaggtg     1800
tccactccga ggtccaactg gtggagagcg gtggaggtgt tgtgcaacct ggccggtccc     1860
tgcgcctgtc ctgctccgca tctggcttcg atttcaccac atattggatg agttgggtga     1920
gacaggcacc tggaaaaggt cttgagtgga ttggagaaat tcatccagat agcagtacga     1980
ttaactatgc gccgtctcta aaggatagat ttacaatatc gcgagacaac gccaagaaca     2040
cattgttcct gcaaatggac agcctgagac ccgaagacac cggggtctat ttttgtgcaa     2100
gcctttactt cggcttcccc tggttttgctt attgggccaa agggacccg gtcaccgtct      2160 cctcagcctc caccaagggc ccatcggtct tccccctggc accctcctcc aagagcacct     2220 ctggggcac agcggccctg ggctgcctgg tcaaggacta cttccccgaa ccggtgacgg       2280
tgtcgtggaa ctcaggcgcc ctgaccagcg gcgtgcacac cttcccggct gtcctacagt     2340
cctcaggact ctactccctc agcagcgtgg tgaccgtgcc ctccagcagc ttgggcaccc     2400
agacctacat ctgcaacgtg aatcacaagc ccagcaacac caaggtggac aagagagttg     2460
agcccaaatc ttgtgacaaa actcacacat gcccaccgtg cccagcacct gaactcctgg     2520
ggggaccgtc agtcttcctc ttccccccaa acccaaggac accctcatg atctcccgga     2580 cccctgaggt cacatgcgtg gtggtggacg tgagccacga agaccctgag gtcaagttca     2640
actggtacgt ggacggcgtg gaggtgcata atgccaagac aaagccgcgg gaggagcagt     2700
acaacagcac gtaccgtgtg gtcagcgtcc tcaccgtcct gcaccaggac tggctgaatg     2760
gcaaggagta caagtgcaag gtctccaaca aagccctccc agcccccatc gagaaaacca     2820
tctccaaagc caaagggcag ccccgagaac cacaggtgta caccctgccc ccatcccggg     2880
aggagatgac caagaaccag gtcagcctga cctgcctggt caaaggcttc tatcccagcg     2940
acatcgccgt ggagtgggag agcaatgggc agccggagaa caactacaag accacgcctc     3000
```

```
ccgtgctgga ctccgacggc tccttcttcc tctatagcaa gctcaccgtg gacaagagca    3060
ggtggcagca ggggaacgtc ttctcatgct ccgtgatgca cgaggctctg cacaaccact    3120
acacgcagaa gagcctctcc ctgtctcccg ggaaatgaaa gccgaattcg cccctctccc    3180 tcccccccc ctaacgttac tggccgaagc cgcttggaat aaggccggtg tgcgtttgtc    3240
tatatgttat tttccaccat attgccgtct tttggcaatg tgagggcccg gaaacctggc    3300
cctgtcttct tgacgagcat tcctaggggt ctttcccctc tcgccaaagg aatgcaaggt    3360
ctgttgaatg tcgtgaagga agcagttcct ctggaagctt cttgaagaca aacaacgtct    3420
gtagcgaccc tttgcaggca gcggaacccc ccacctggcg acaggtgcct ctgcggccaa    3480
aagccacgtg tataagatac acctgcaaag gcggcacaac cccagtgcca cgttgtgagt    3540
tggatagttg tggaaagagt caaatggctc tcctcaagcg tattcaacaa ggggctgaag    3600
gatgcccaga aggtacccca ttgtatggga tctgatctgg ggcctcggtg cacatgcttt    3660
acatgtgttt agtcgaggtt aaaaaaacgt ctaggccccc cgaaccacgg ggacgtggtt    3720
ttcctttgaa aaacacgatg ataatatggc ctcctttgtc tctctgctcc tggtaggcat    3780
cctattccat gccacccagg ccgacatcca gctgacccag agcccaagca gcctgagcgc    3840
cagcgtgggt gacagagtga ccatcacctg taaggccagt caggatgtgg gtacttctgt    3900
agcctggtac cagcagaagc caggtaaggc tccaaagctg ctgatctact ggacatccac    3960
ccggcacact ggtgtgccaa gcagattcag cggtagcggt agcggtaccg acttcacctt    4020
caccatcagc agcctccagc cagaggacat cgccacctac tactgccagc aatatagcct    4080
ctatcggtcg ttcggccaag ggaccaaggt ggaaatcaaa cgaactgtgg ctgcaccatc    4140
tgtcttcatc ttcccgccat ctgatgagca gttgaaatct ggaactgcct ctgttgtgtg    4200
cctgctgaat aacttctatc ccagagaggc caaagtacag tggaaggtgg ataacgccct    4260
ccaatcgggt aactcccagg agagtgtcac agagcaggac agcaaggaca gcacctacag    4320
cctcagcagc accctgacgc tgagcaaagc agactacgag aaacacaaag tctacgcctg    4380
cgaagtcacc catcagggcc tgagctcgcc cgtcacaaag agcttcaaca ggggagagtg    4440
ttagagatcc cccgggctgc aggaattcga tatcaagctt atcgataatc aacctctgga    4500
ttacaaaatt tgtgaaagat tgactggtat tcttaactat gttgctcctt ttacgctatg    4560
tggatacgct gctttaatgc ctttgtatca tgctattgct tcccgtatgg ctttcatttt    4620
ctcctccttg tataaatcct ggttgctgtc tctttatgag gagttgtggc ccgttgtcag    4680
gcaacgtggc gtggtgtgca ctgtgtttgc tgacgcaacc cccactggtt ggggcattgc    4740
caccacctgt cagctccttt ccgggacttt cgctttcccc ctccctattg ccacggcgga    4800
actcatcgcc gcctgccttg cccgctgctg acagggggct cggctgttgg gcactgacaa    4860
ttccgtggtg ttgtcgggga atcatcgtc ctttccttgg ctgctcgcct gtgttgccac    4920
ctggattctg cgcgggacgt ccttctgcta cgtcccttcg ccctcaatc cagcggacct    4980 tccttcccgc ggcctgctgc cggctctgcg gcctcttccg cgtcttcgcc ttcgccctca    5040
gacgagtcgg atctcccttt gggccgcctc cccgcctgat cgataccgtc aacatcgata    5100
aaataaaaga ttttatttag tctccagaaa aaggggggaa tgaaagaccc cacctgtagg    5160
tttggcaagc tagcttaagt aacgccattt tgcaaggcat ggaaaatac ataactgaga    5220 atagagaagt tcagatcaag gtcaggaaca gatggaacag ctgaatatgg gccaaacagg    5280
atatctgtgg taagcagttc ctgccccggc tcagggccaa gaacagatgg aacagctgaa    5340
```

-continued

| | |
|---|---|
| tatgggccaa acaggatatc tgtggtaagc agttcctgcc ccggctcagg gccaagaaca | 5400 |
| gatggtcccc agatgcggtc cagccctcag cagtttctag agaaccatca gatgtttcca | 5460 |
| gggtgcccca aggacctgaa atgaccctgt gccttatttg aactaaccaa tcagttcgct | 5520 |
| tctcgcttct gttcgcgcgc ttctgctccc cgagctcaat aaaagagccc acaacccctc | 5580 |
| actcggggcg ccagtcctcc gattgactga gtcgcccggg tacccgtgta tccaataaac | 5640 |
| cctcttgcag ttgcatccga cttgtggtct cgctgttcct tgggagggtc tcctctgagt | 5700 |
| gattgactac ccgtcagcgg gggtctttca tt | 5732 |

<210> SEQ ID NO 7
<211> LENGTH: 9183
<212> TYPE: DNA
<213> ORGANISM: Artificial Sequence
<220> FEATURE:
<223> OTHER INFORMATION: Synthetic

<400> SEQUENCE: 7

| | |
|---|---|
| aaagacccca cccgtaggtg gcaagctagc ttaagtaacg ccactttgca aggcatggaa | 60 |
| aaatacataa ctgagaatag aaaagttcag atcaaggtca ggaacaaaga aacagctgaa | 120 |
| taccaaacag gatatctgtg gtaagcggtt cctgccccgg ctcagggcca agaacagatg | 180 |
| agacagctga gtgatgggcc aaacaggata tctgtggtaa gcagttcctg ccccggctcg | 240 |
| ggccaagaa cagatggtcc ccagatgcgg tccagccctc agcagtttct agtgaatcat | 300 |
| cagatgtttc cagggtgccc caaggacctg aaaatgaccc tgtaccttat ttgaactaac | 360 |
| caatcagttc gcttctcgct tctgttcgcg cgcttccgct ctccgagctc aataaaagag | 420 |
| cccacaaccc ctcactcggc gcgccagtct tccgatagac tgcgtcgccc gggtacccgt | 480 |
| attcccaata aagcctcttg ctgtttgcat ccgaatcgtg gtctcgctgt tccttgggag | 540 |
| ggtctcctct gagtgattga ctacccacga cgggggtctt tcatttgggg gctcgtccgg | 600 |
| gatttggaga cccctgccca gggaccaccg acccaccacc gggaggtaag ctggccagca | 660 |
| acttatctgt gtctgtccga ttgtctagtc tctatgtttg atgttatgcg cctgcgtctg | 720 |
| tactagttag ctaactagct ctgtatctgg cggacccgtg gtggaactga cgagttctga | 780 |
| acacccggcc gcaaccctgg gagacgtccc agggactttg ggggccgttt ttgtggcccg | 840 |
| acctgaggaa gggagtcgat gtggaatccg accccgtcag gatatgtggt tctggtagga | 900 |
| gacgagaacc taaaacagtt cccgcctccg tctgaatttt tgctttcggt ttggaaccga | 960 |
| agccgcgcgt cttgtctgct gcagcgctgc agcatcgttc tgtgttgtct ctgtctgact | 1020 |
| gtgtttctgt atttgtctga aaattagggc cagactgtta ccactccctt aagtttgacc | 1080 |
| ttaggtcact ggaaagatgt cgagcggatc gctcacaacc agtcggtaga tgtcaagaag | 1140 |
| agacgttggg ttaccttctg ctctgcagaa tggccaacct ttaacgtcgg atggccgcga | 1200 |
| gacggcacct ttaaccgaga cctcatcacc caggttaaga tcaaggtctt ttcacctggc | 1260 |
| ccgcatggac acccagacca ggtcccctac atcgtgacct gggaagcctt ggcttttgac | 1320 |
| cccccctccct gggtcaagcc ctttgtacac cctaagcctc cgcctcctct tcctccatcc | 1380 |
| gccccgtctc tcccccttga acctcctcgt tcgaccccgc ctcgatcctc cctttatcca | 1440 |
| gccctcactc cttctctagg cgccggaatt ccgatctgat caagacagga tgaggatc | 1500 |
| gtttcgcatg attgaacaag atggattgca cgcaggttct ccggccgctt gggtggagag | 1560 |
| gctattcggc tatgactggg cacaacagac aatcggctgc tctgatgccg ccgtgttccg | 1620 |
| gctgtcagcg caggggcgcc cggttctttt tgtcaagacc gacctgtccg gtgccctgaa | 1680 |

-continued

```
tgaactgcag gacgaggcag cgcggctatc gtggctggcc acgacgggcg ttccttgcgc      1740
agctgtgctc gacgttgtca ctgaagcggg aagggactgg ctgctattgg gcgaagtgcc      1800
ggggcaggat ctcctgtcat ctcaccttgc tcctgccgag aaagtatcca tcatggctga      1860
tgcaatgcgg cggctgcata cgcttgatcc ggctacctgc ccattcgacc accaagcgaa      1920
acatcgcatc gagcgagcac gtactcggat ggaagccggt cttgtcgatc aggatgatct      1980
ggacgaagag catcaggggc tcgcgccagc cgaactgttc gccaggctca aggcgcgcat      2040
gcccgacggc gaggatctcg tcgtgaccca tggcgatgcc tgcttgccga atatcatggt      2100
ggaaaatggc cgcttttctg gattcatcga ctgtggccgg ctgggtgtgg cggaccgcta      2160
tcaggacata gcgttggcta cccgtgatat tgctgaagag cttggcggcg aatgggctga      2220
ccgcttcctc gtgctttacg gtatcgccgc tcccgattcg cagcgcatcg ccttctatcg      2280
ccttcttgac gagttcttct gagcgggact ctggggttcg aaatgaccga ccaagcgacg      2340
cccaacctgc catcacgaga tttcgattcc accgccgcct tctatgaaag gttgggcttc      2400
ggaatcgttt tccgggacgc cggctggatg atcctccagc gcggggatct catgctggag      2460
ttcttcgccc accccgggct cgatcccctc gcgagttggt tcagctgctg cctgaggctg      2520
gacgacctcg cggagttcta ccggcagtgc aaatccgtcg gcatccagga aaccagcagc      2580
ggctatccgc gcatccatgc ccccgaactg caggagtggg gaggcacgat ggccgctttg      2640
gtcgaggcgg atcctagaac tagcgaaaat gcaagagcaa agacgaaaac atgccacaca      2700
tgaggaatac cgattctctc attaacatat tcaggccagt tatctgggct aaaagcaga      2760 agtccaaccc agataacgat catatacatg gttctctcca gaggttcatt actgaacact      2820
cgtccgagaa taacgagtgg atcagtcctg ggtggtcatt gaaaggactg atgctgaagt      2880
tgaagctcca atactttggc cacctgatgc gaagaactga ctcatgtgat aagaccctga      2940
tactgggaaa gattgaaggc aggaggagaa gggatgacag aggatggaag agttggatgg      3000
aatcaccaac tcgatggaca tgagtttgag caagcttcca ggagttggta atgggcaggg      3060
aagcctggcg tgctgcagtc catggggttg caaagagttg acactactg agtgactgaa       3120 ctgaactgat agtgtaatcc atggtacaga atataggata aaaagagga agagtttgcc       3180 ctgattctga agagttgtag gatataaaag tttagaatac ctttagtttg gaagtcttaa      3240
attatttact taggatgggt acccactgca atataagaaa tcaggcttta gagactgatg      3300
tagagagaat gagccctggc ataccagaag ctaacagcta ttggttatag ctgttataac      3360
caatatataa ccaatatatt ggttatatag catgaagctt gatgccagca atttgaagga      3420
accatttaga actagtatcc taaactctac atgttccagg acactgatct aaagctcag       3480 gttcagaatc ttgttttata ggctctaggt gtatattgtg gggcttccct ggtggctcag      3540
atggtaaagt gtctgcctgc aatgtgggtg atctgggttc gatccctggc ttgggaagat      3600
cccctggaga aggaaatggc aacccactct agtactctta cctggaaaat tccatggaca      3660
gaggagcctt gtaagctaca gtccatggga ttgcaaagag ttgaacacaa ctgagcaact      3720
aagcacagca cagtacagta tacacctgtg aggtgaagtg aagtgaaggt tcaatgcagg      3780
gtctcctgca ttgcagaaag attctttacc atctgagcca ccaggaagc ccaagaatac       3840 tggagtgggt agcctattcc ttctccaggg gatcttccca tcccaggaat tgaactggag      3900
tctcctgcat ttcaggtgga ttcttcacca gctgaactac caggtggata ctactccaat      3960
attaaagtgc ttaaagtcca gttttcccac ctttcccaaa aaggttgggt cactcttttt      4020
```

```
taaccttctg tggcctactc tgaggctgtc tacaagctta tatatttatg aacacattta    4080
ttgcaagttg ttagttttag atttacaatg tggtatctgg ctatttagtg gtattggtgg    4140
ttggggatgg ggaggctgat agcatctcag agggcagcta gatactgtca tacacacttt    4200
tcaagttctc cattttttgtg aaatagaaag tctctggatc taagttatat gtgattctca    4260
gtctctgtgg tcatattcta ttctactcct gaccactcaa caaggaacca agatatcaag    4320
ggacacttgt tttgtttcat gcctgggttg agtgggccat gacatatgtt ctgggccttg    4380
ttacatggct ggattggttg dacaagtgcc agctctgatc ctgggactgt ggcatgtgat    4440
gacatacacc ccctctccac attctgcatg tctctagggg ggaaggggga agctcggtat    4500
agaaccttta ttgtattttc tgattgcctc acttcttata ttgccccat gcccttcttt     4560
gttcctcaag taaccagaga cagtgcttcc cagaaccaac cctacaagaa acaaagggct    4620
aaacaaagcc aaatgggaag caggatcatg gtttgaactc tttctggcca gagaacaata    4680
cctgctatgg actagatact gggagaggga aaggaaaagt aggtgaatt atggaaggaa     4740
gctggcaggc tcagcgtttc tgtcttggca tgaccagtct ctcttcattc tcttcctaga    4800
tgtagggctt ggtaccagag cccctgaggc tttctgcatg aatataaata tatgaaactg    4860
agtgatgctt ccatttcagg ttcttggggg cgccgaattc gagctcggta cccggggatc    4920
tcgacggatc cgattactta ctggcaggtg ctggggcttt ccgagacaat cgcgaacatc    4980
tacaccacac aacaccgcct cgaccagggt gagatatcgg ccggggacgc ggcggtggta    5040
attacaagcg agatccgatt acttactggc aggtgctggg ggcttccgag acaatcgcga    5100
acatctacac cacacaacac cgcctcgacc agggtgagat atcggccggg gacgcggcgg    5160
tggtaattac aagcgagatc cccgggaatt caggacctca ccatgggatg gagctgtatc    5220
atcctcttct tggtagcaac agctacaggt gtccactccg aggtccaact ggtggagagc    5280
ggtggaggtg ttgtgcaacc tggccggtcc ctgcgcctgt cctgctccgc atctggcttc    5340
gatttcacca catattggat gagttgggtg agacaggcac ctggaaaagg tcttgagtgg    5400
attggagaaa ttcatccaga tagcagtacg attaactatg cgccgtctct aaaggataga    5460
tttacaatat cgcgagacaa cgccaagaac acattgttcc tgcaaatgga cagcctgaga    5520
cccgaagaca ccggggtcta ttttttgtgca agcctttact tcggcttccc ctggtttgct    5580
tattggggcc aagggacccc ggtcaccgtc tcctcagcct ccaccaaggg cccatcggtc    5640
ttcccccctgg cacccctcctc caagagcacc tctgggggca cagcggccct gggctgcctg    5700
gtcaaggact acttccccga accggtgacg gtgtcgtgga actcaggcgc cctgaccagc    5760
ggcgtgcaca ccttcccggc tgtcctacag tcctcaggac tctactccct cagcagcgtg    5820
gtgaccgtgc cctccagcag cttgggcacc cagacctaca tctgcaacgt gaatcacaag    5880
cccagcaaca ccaaggtgga caagagagtt gagcccaaat cttgtgacaa aactcacaca    5940
tgcccaccgt gcccagcacc tgaactcctg ggggaccgt cagtcttcct cttcccccca     6000
aaacccaagg acaccctcat gatctcccgg acccctgagg tcacatgcgt ggtggtggac    6060
gtgagccacg aagaccctga ggtcaagttc aactggtacg tggacggcgt ggaggtgcat    6120
aatgccaaga caaagccgcg ggaggagcag tacaacagca cgtaccgtgt ggtcagcgtc    6180
ctcaccgtcc tgcaccagga ctggctgaat ggcaaggagt acaagtgcaa ggtctccaac    6240
aaagccctcc cagcccccat cgagaaaacc atctccaaag ccaagggca gccccgagaa     6300
ccacaggtgt acaccctgcc cccatcccgg gaggagatga ccaagaacca ggtcagcctg    6360
acctgcctgg tcaaaggctt ctatcccagc gacatcgccg tggagtggga gagcaatggg    6420
```

```
cagccggaga acaactacaa gaccacgcct cccgtgctgg actccgacgg ctccttcttc    6480
ctctatagca agctcaccgt ggacaagagc aggtggcagc aggggaacgt cttctcatgc    6540
tccgtgatgc acgaggctct gcacaaccac tacacgcaga agagcctctc cctgtctccc    6600
gggaaatgaa agccgaattc gcccctctcc ctcccccccc cctaacgtta ctggccgaag    6660
ccgcttggaa taaggccggt gtgcgtttgt ctatatgtta ttttccacca tattgccgtc    6720
ttttggcaat gtgagggccc ggaaacctgg ccctgtcttc ttgacgagca ttcctagggg    6780
tctttcccct ctcgccaaag gaatgcaagg tctgttgaat gtcgtgaagg aagcagttcc    6840
tctggaagct tcttgaagac aaacaacgtc tgtagcgacc ctttgcaggc agcggaaccc    6900
cccacctggc gacaggtgcc tctgcggcca aaagccacgt gtataagata cacctgcaaa    6960
ggcggcacaa ccccagtgcc acgttgtgag ttggatagtt gtggaaagag tcaaatggct    7020
ctcctcaagc gtattcaaca aggggctgaa ggatgcccag aaggtacccc attgtatggg    7080
atctgatctg gggcctcggt gcacatgctt tacatgtgtt tagtcgaggt taaaaaaacg    7140
tctaggcccc ccgaaccacg gggacgtggt tttccttga aaaacacgat gataatatgg    7200
cctcctttgt ctctctgctc ctggtaggca tcctattcca tgccacccag gccgacatcc    7260
agctgaccca gagcccaagc agcctgagcg ccagcgtggg tgacagagtg accatcacct    7320
gtaaggccag tcaggatgtg ggtacttctg tagcctggta ccagcagaag ccaggtaagg    7380
ctccaaagct gctgatctac tggacatcca cccggcacac tggtgtgcca agcagattca    7440
gcggtagcgg tagcggtacc gacttcaccc tcaccatcag cagcctccag ccagaggaca    7500
tcgccaccta ctactgccag caatatagcc tctatcggtc gttcggccaa gggaccaagg    7560
tggaaatcaa acgaactgtg gctgcaccat ctgtcttcat cttcccgcca tctgatgagc    7620
agttgaaatc tggaactgcc tctgttgtgt gcctgctgaa taacttctat cccagagagg    7680
ccaaagtaca gtggaaggtg gataacgccc tccaatcggg taactcccag gagagtgtca    7740
cagagcagga cagcaaggac agcacctaca gcctcagcag caccctgacg ctgagcaaag    7800
cagactacga gaaacacaaa gtctacgcct gcgaagtcac ccatcagggc ctgagctcgc    7860
ccgtcacaaa gagcttcaac aggggagagt gttagagatc cccgggctg caggaattcg    7920 atatcaagct tatcgataat caacctctgg attacaaaat ttgtgaaaga ttgactggta    7980
ttcttaacta tgttgctcct tttacgctat gtggatacgc tgctttaatg cctttgtatc    8040
atgctattgc ttcccgtatg gctttcattt tctcctcctt gtataaatcc tggttgctgt    8100
ctctttatga ggagttgtgg cccgttgtca ggcaacgtgg cgtggtgtgc actgtgtttg    8160
ctgacgcaac ccccactggt tggggcattg ccaccacctg tcagctcctt ccgggactt    8220 tcgctttccc cctccctatt gccacggcgg aactcatcgc cgcctgcctt gcccgctgct    8280
ggacaggggc tcggctgttg ggcactgaca attccgtggt gttgtcgggg aaatcatcgt    8340
cctttccttg gctgctcgcc tgtgttgcca cctggattct gcgcgggacg tccttctgct    8400
acgtcccttc ggccctcaat ccagcggacc ttccttcccg cggcctgctg ccggctctgc    8460
ggcctcttcc gcgtcttcgc cttcgccctc agacgagtcg gatctccctt tgggccgcct    8520
ccccgcctga tcgataccgt caacatcgat aaaataaaag attttattta gtctccagaa    8580
aaagggggga atgaaagacc ccacctgtag gtttggcaag ctagcttaag taacgccatt    8640
ttgcaaggca tggaaaaata caactaagag aatagaaag ttcagatcaa ggtcaggaac    8700
agatggaaca gctgaatatg ggccaaacag gatatctgtg gtaagcagtt cctgccccgg    8760
```

-continued

| | |
|---|---|
| ctcagggcca agaacagatg aacagctga atatgggcca aacaggatat ctgtggtaag | 8820 |
| cagttcctgc cccggctcag ggccaagaac agatggtccc cagatgcggt ccagccctca | 8880 |
| gcagttctta gagaaccatc agatgtttcc agggtgcccc aaggacctga atgaccctg | 8940 |
| tgccttattt gaactaacca atcagttcgc ttctcgcttc tgttcgcgcg cttctgctcc | 9000 |
| ccgagctcaa taaaagagcc cacaaccct cactcggggc gccagtcctc cgattgactg | 9060 |
| agtcgcccgg gtacccgtgt atccaataaa ccctcttgca gttgcatccg acttgtggtc | 9120 |
| tcgctgttcc ttgggagggt ctcctctgag tgattgacta cccgtcagcg ggggtctttc | 9180 |
| att | 9183 |

<210> SEQ ID NO 8
<211> LENGTH: 5711
<212> TYPE: DNA
<213> ORGANISM: Artificial Sequence
<220> FEATURE:
<223> OTHER INFORMATION: Synthetic

<400> SEQUENCE: 8

| | |
|---|---|
| gatcagtcct gggtggtcat tgaaaggact gatgctgaag ttgaagctcc aatactttgg | 60 |
| ccacctgatg cgaagaactg actcatgtga taagaccctg atactgggaa agattgaagg | 120 |
| caggaggaga agggatgaca gaggatggaa gagttggatg gaatcaccaa ctcgatggac | 180 |
| atgagtttga gcaagcttcc aggagttggt aatgggcagg gaagcctggc gtgctgcagt | 240 |
| ccatggggtt gcaaagagtt ggacactact gagtgactga actgaactga tagtgtaatc | 300 |
| catggtacag aatataggat aaaaagagg aagagtttgc cctgattctg aagagttgta | 360 |
| ggatataaaa gtttagaata cctttagttt ggaagtctta aattatttac ttaggatggg | 420 |
| tacccactgc aatataagaa atcaggcttt agagactgat gtagagagaa tgagccctgg | 480 |
| cataccagaa gctaacagct attggttata gctgttataa ccaatatata accaatatat | 540 |
| tggttatata gcatgaagct tgatgccagc aatttgaagg aaccatttag aactagtatc | 600 |
| ctaaactcta catgttccag gacactgatc ttaaagctca ggttcagaat cttgttttat | 660 |
| aggctctagg tgtatattgt ggggcttccc tggtggctca gatggtaaag tgtctgcctg | 720 |
| caatgtgggt gatctgggtt cgatccctgg cttgggaaga tccccctggag aaggaaatgg | 780 |
| caacccactc tagtactctt acctggaaaa ttccatggac agaggagcct tgtaagctac | 840 |
| agtccatggg attgcaaaga gttgaacaca actgagcaac taagcacagc acagtacagt | 900 |
| atacacctgt gaggtgaagt gaagtgaagg ttcaatgcag ggtctcctgc attgcagaaa | 960 |
| gattctttac catctgagcc accagggaag cccaagaata ctggagtggg tagcctattc | 1020 |
| cttctccagg ggatcttccc atcccaggaa ttgaactgga gtctcctgca tttcaggtgg | 1080 |
| attcttcacc agctgaacta ccaggtggat actactccaa tattaaagtg cttaaagtcc | 1140 |
| agttttccca cctttcccaa aaaggttggg tcactctttt ttaaccttct gtggcctact | 1200 |
| ctgaggctgt ctacaagctt atatatttat gaacacattt attgcaagtt gttagttta | 1260 |
| gatttacaat gtggtatctg ctatttagt ggtattggtg gttggggatg gggaggctga | 1320 |
| tagcatctca gagggcagct agatactgtc atacacactt ttcaagttct ccatttttgt | 1380 |
| gaaatagaaa gtctctggat ctaagttata tgtgattctc agtctctgtg gtcatattct | 1440 |
| attctactcc tgaccactca acaaggaacc aagatatcaa gggacacttg ttttgtttca | 1500 |
| tgcctgggtt gagtgggcca tgacatatgt tctgggcctt gttacatggc tggattggtt | 1560 |
| ggacaagtgc cagctctgat cctgggactg tggcatgtga tgacatacac ccctctccca | 1620 |

```
cattctgcat gtctctaggg gggaaggggg aagctcggta tagaaccttt attgtatttt    1680
ctgattgcct cacttcttat attgccccca tgcccttctt tgttcctcaa gtaaccagag    1740
acagtgcttc ccagaaccaa ccctacaaga aacaaagggc taaacaaagc caaatgggaa    1800
gcaggatcat ggtttgaact cttcctggcc agagaacaat acctgctatg gactagatac    1860
tgggagaggg aaaggaaaag tagggtgaat tatggaagga agctggcagg ctcagcgttt    1920
ctgtcttggc atgaccagtc tctcttcatt ctcttcctag atgtagggct tggtaccaga    1980
gcccctgagg cttctgcat  gaatataaat atatgaaact gagtgatgct tccatttcag    2040
gttcttgggg gcgccgaatt cgagctcggt acccggggat ctcgacggat ccgattactt    2100
actggcaggt gctggggct tccgagacaa tcgcgaacat ctacaccaca caacaccgcc     2160
tcgaccaggg tgagatatcg gccggggacg cggcgtggt aattacaagc gagatccgat     2220
tacttactgg caggtgctgg gggcttccga gacaatcgcg aacatctaca ccacacaaca    2280
ccgcctcgac cagggtgaga tatcggccgg ggacgcggcg gtggtaatta agcgagat     2340
ctcgagaagc ttgttgggaa ttcaggccat cgatcccgcc gccaccatgg aatggagctg    2400
ggtctttctc ttcttcctgt cagtaactac aggtgtccac tccgacatcc agatgaccca    2460
gtctccagcc tccctatctg catctgtggg agaaactgtc actatcacat gtcgagcaag    2520
tgggaatatt cacaattatt tagcatggta tcagcagaaa cagggaaaat ctcctcagct    2580
cctggtctat aatgcaaaaa ccttagcaga tggtgtgcca tcaaggttca gtggcagtgg    2640
atcaggaaca caatattctc tcaagatcaa cagcctgcag cctgaagatt tgggagttta    2700
ttactgtcaa cattttga gtactccgtg gacgttcggt ggaggcacca agctggaaat     2760
caaacgggct gatgctgcac caactgtatc catcttccca ccatccagtg agcagttaac    2820
atctggaggt gcctcagtcg tgtgcttctt gaacaacttc taccccaaag acatcaatgt    2880
caagtggaag attgatggca gtgaacgaca aaatggcgtc ctgaacagtt ggactgatca    2940
ggacagcaaa gacagcacct acagcatgag cagcaccctc acattgacca aggacgagta    3000
tgaacgacat aacagctata cctgtgaggc cactcacaag acatcaactt cacccattgt    3060
caagagcttc aacaggaatg agtgttgaaa gcatcgattt cccctgaatt cgcccctctc    3120
cctcccccc cctaacgtt actggccgaa gccgcttgga ataaggcgg tgtgcgtttg      3180
tctatatgtt atttttccacc atattgccgt cttttggcaa tgtgagggcc cggaaacctg    3240
gccctgtctt cttgacgagc attcctaggg gtctttcccc tctcgccaaa ggaatgcaag    3300
gtctgttgaa tgtcgtgaag gaagcagttc ctctggaagc ttcttgaaga caaacaacgt    3360
ctgtagcgac cctttgcagg cagcggaacc ccccacctgg cgacaggtgc ctctgcggcc    3420
aaaagccacg tgtataagat acacctgcaa aggcggcaca accccagtgc cacgttgtga    3480
gttgatagt tgtggaaaga gtcaaatggc tctcctcaag cgtattcaac aaggggctga     3540
aggatgccca gaaggtaccc cattgtatgg gatctgatct ggggcctcgg tgcacatgct    3600
ttacatgtgt ttagtcgagg ttaaaaaaac gtctaggccc cccgaaccac ggggacgtgg    3660
ttttcctttg aaaacacga tgataatatg gcctcctttg tctctctgct cctggtaggc     3720
atcctattcc atgccaccca ggccgaggtt cagcttcagc agtctgggc agagcttgtg     3780
aagccagggg cctcagtcaa gttgtcctgc acagcttctg gcttcaacat taagacacc    3840
tttatgcact gggtgaagca gaggcctgaa cagggcctgg agtggattgg aaggattgat    3900
cctgcgaatg gaatactga atatgacccg aagttccagg gcaaggccac tataacagca    3960
```

-continued

```
gacacatcct caacacagt caacctgcag ctcagcagcc tgacatctga ggacactgcc      4020
gtctattact gtgctagtgg aggggaactg gggtttcctt actggggcca agggactctg      4080
gtcactgtct ctgcagccaa aacgacaccc ccatctgtct atccactggc ccctggatct      4140
gctgcccaaa ctaactccat ggtgaccctg ggatgcctgg tcaagggcta tttccctgag      4200
ccagtgacag tgacctggaa ctctggatcc ctgtccagcg gtgtgcacac cttcccagct      4260
gtcctgcagt ttgacctcta cactctgagc agctcagtga ctgtcccctc cagcacctgg      4320
cccagcgaga ccgtcacctg caacgttgcc caccggcca gcagcaccaa ggtggacaag       4380
aaaattgtgc ccagggattg tactagtgga ggtggaggta gccaccatca ccatcaccat      4440
taatctagag ttaagcggcc gtcgagatct cgacatcgat aatcaacctc tggattacaa      4500
aatttgtgaa agattgactg gtattcttaa ctatgttgct ccttttacgc tatgtggata      4560
cgctgcttta atgcctttgt atcatgctat tgcttcccgt atggctttca ttttctcctc      4620
cttgtataaa tcctggttgc tgtctcttta tgaggagttg tggcccgttg tcaggcaacg      4680
tggcgtggtg tgcactgtgt ttgctgacgc aaccccact ggttggggca ttgccaccac       4740
ctgtcagctc ctttccggga cttcgcttt ccccctccct attgccacgg cggaactcat       4800
cgccgcctgc cttcccgct gctggacagg ggctcggctg ttgggcactg acaattccgt       4860
ggtgttgtcg gggaaatcat cgtcctttcc ttggctgctc cctgtgttg ccacctggat       4920 tctgcgcggg acgtccttct gctacgtccc ttcggccctc aatccagcgg accttccttc      4980
ccgcggcctg ctgccggctc tgcggcctct tccgcgtctt cgccttcgcc tcagacgag       5040 tcggatctcc ctttgggccg cctccccgcc tgatcgataa aataaaagat tttatttagt      5100
ctccagaaaa agggggggaat gaaagacccc acctgtaggt ttggcaagct agcttaagta     5160
acgccatttt gcaaggcatg gaaaaataca taactgagaa tagagaagtt cagatcaagg      5220
tcaggaacag atggaacagc tgaatatggg ccaaacagga tatctgtggt aagcagttcc     5280
tgccccggct cagggccaag aacagatgga acagctgaat atgggccaaa caggatatct     5340
gtggtaagca gttcctgccc cggctcaggg ccaagaacag atggtcccca gatgcggtcc     5400
agccctcagc agtttctaga gaaccatcag atgtttccag ggtgccccaa ggacctgaaa     5460
tgaccctgtg ccttatttga actaaccaat cagttcgctt ctcgcttctg ttcgcgcgct     5520
tctgctcccc gagctcaata aaagagccca caaccctca ctcggggcgc cagtcctccg      5580
attgactgag tcgcccgggt acccgtgtat ccaataaacc ctcttgcagt tgcatccgac     5640
ttgtggtctc gctgttcctt gggagggtct cctctgagtg attgactacc cgtcagcggg     5700
ggtctttcat t                                                          5711
```

<210> SEQ ID NO 9
<211> LENGTH: 5130
<212> TYPE: DNA
<213> ORGANISM: Artificial Sequence
<220> FEATURE:
<223> OTHER INFORMATION: Synthetic

<400> SEQUENCE: 9

```
tttgaaagac cccacccgta ggtggcaagc tagcttaagt aacgccactt tgcaaggcat       60
ggaaaaatac ataactgaga atagaaaagt tcagatcaag gtcaggaaca aagaaacagc      120
tgaataccaa acaggatatc tgtggtaagc ggttcctgcc ccggctcagg gccaagaaca      180
gatgagacag ctgagtgatg ggccaaacag gatatctgtg gtaagcagtt cctgccccgg      240
ctcggggcca agaacagatg gtccccagat gcggtccagc cctcagcagt ttctagtgaa      300
```

-continued

```
tcatcagatg tttccagggt gccccaagga cctgaaaatg accctgtacc ttatttgaac      360
taaccaatca gttcgcttct cgcttctgtt cgcgcgcttc cgctctccga gctcaataaa      420
agagcccaca acccctcact cggcgcgcca gtcttccgat agactgcgtc gcccgggtac      480
ccgtattccc aataaagcct cttgctgttt gcatccgaat cgtggtctcg ctgttccttg      540
ggagggtctc ctctgagtga ttgactaccc acgacggggg tctttcattt ggggctcgt       600
ccgggatttg agacccctg cccagggacc accgacccac caccgggagg taagctggcc      660
agcaacttat ctgtgtctgt ccgattgtct agtgtctatg tttgatgtta tgcgcctgcg      720
tctgtactag ttagctaact agctctgtat ctggcggacc cgtggtggaa ctgacgagtt      780
ctgaacaccc ggccgcaacc ctgggagacg tcccagggac tttgggggcc gttttttgtgg    840
cccgacctga ggaagggagt cgatgtggaa tccgaccccg tcaggatatg tggttctggt     900
aggagacgag aacctaaaac agttcccgcc tccgtctgaa tttttgcttt cggtttggaa     960
ccgaagccgc gcgtcttgtc tgctgcagcc aagcttgggc tgcaggtcga ggactgggga    1020
ccctgcaccg aacatggaga acacaacatc aggattccta ggaccctgc tcgtgttaca    1080
ggcgggtttt ttcttgttga caagaatcct cacaatacca cagagtctag actcgtggtg   1140
gacttctctc aattttctag ggggagcacc cacgtgtcct ggccaaaatt cgcagtcccc    1200
aacctccaat cactcaccaa cctcttgtcc tccaatttgt cctggctatc gctggatgtg    1260
tctgcggcgt tttatcatat tcctcttcat cctgctgcta tgcctcatct tcttgttggt    1320
tcttctggac taccaaggta tgttgcccgt ttgtcctcta cttccaggaa catcaactac    1380
cagcacggga ccatgcaaga cctgcacgat tcctgctcaa ggaacctcta tgtttccctc    1440
ttgttgctgt acaaaacctt cggacggaaa ctgcacttgt attcccatcc catcatcctg    1500
ggctttcgca agattcctat gggagtgggc ctcagtccgt ttctcctggc tcagtttact    1560
agtgccattt gttcagtggt tcgtagggct ttcccccact gtttggcttt cagttatatg    1620
gatgatgtgg tattggggc caagtctgta caacatcttg agtcccttt tacctctatt    1680
accaattttc ttttgtcttt gggtatacat ttaaaccca ataaaaccaa acgttggggc     1740
tactccctta acttcatggg atatgtaatt ggatgttggg gtactttacc gcaagaacat    1800
attgtactaa aaatcaagca atgttttcga aaactgcctg taaatagacc tattgattgg    1860
aaagtatgtc agagacttgt gggtcttttg ggctttgctg cccctttac acaatgtggc   1920
tatcctgcct taatgccttt atatgcatgt atacaatcta agcaggcttt cactttctcg     1980
ccaacttaca aggcctttct gtgtaaacaa tatctgaacc tttaccccgt tgcccggcaa    2040
cggtcaggtc tctgccaagt gtttgctgac gcaaccccca ctggatgggg cttggctatc    2100
ggccatagcc gcatgcgcgg acctttgtgg ctcctctgcc gatccatact gcggaactcc    2160
tagcagcttg ttttgctcgc aggcggtctg gagcgaaact tatcggcacc gacaactctg    2220
ttgtcctctc tcggaaatac acctcctttc catggctgct agggtgtgct gccaactgga    2280
tcccctcagg atatagtagt ttcgcttttg catagggagg gggaaatgta gtcttatgca    2340
atacacttgt agtcttgcaa catggtaacg atgagttagc aacatgcctt acaaggagag    2400
aaaaagcacc gtgcatgccg attggtgaa gtaaggtggt acgatcgtgc cttattagga    2460
aggcaacaga caggtctgac atggattgga cgaaccactg aattccgcat tgcagagata    2520
attgtattta agtgcctagc tcgatacagc aaacgccatt tttgaccatt caccacattg    2580
gtgtgcacct tccaaagctt cacgctgccg caagcactca gggcgcaagg gctgctaaag   2640
```

```
gaagcggaac acgtagaaag ccagtccgca gaaacggtgc tgaccccgga tgaatgtcag    2700
ctactgggct atctggacaa gggaaaacgc aagcgcaaag agaaagcagg tagcttgcag    2760
tgggcttaca tggcgatagc tagactgggc ggttttatgg acagcaagcg aaccggaatt    2820
gccagctggg gcgccctctg gtaaggttgg gaagccctgc aaagtaaact ggatggcttt    2880
cttgccgcca aggatctgat ggcgcagggg atcaagatct gatcaagaga caggatgagg    2940
atcgtttcgc atgattgaac aagatggatt gcacgcaggt tctccggccg cttgggtgga    3000
gaggctattc ggctatgact gggcacaaca gacaatcggc tgctctgatg ccgccgtgtt    3060
ccggctgtca gcgcaggggc gcccggttct ttttgtcaag accgacctgt ccggtgccct    3120
gaatgaactg caggacgagg cagcgcggct atcgtggctg gccacgacgg gcgttccttg    3180
cgcagctgtg ctcgacgttg tcactgaagc gggaagggac tggctgctat tgggcgaagt    3240
gccggggcag gatctcctgt catctcacct tgctcctgcc gagaaagtat ccatcatggc    3300
tgatgcaatg cggcggctgc atacgcttga tccggctacc tgcccattcg accaccaagc    3360
gaaacatcgc atcgagcgag cacgtactcg gatggaagcc ggtcttgtcg atcaggatga    3420
tctggacgaa gagcatcagg ggctcgcgcc agccgaactg ttcgccaggc tcaaggcgcg    3480
catgcccgac ggcgaggatc tcgtcgtgac ccatggcgat gcctgcttgc cgaatatcat    3540
ggtggaaaat ggccgctttt ctggattcat cgactgtggc cggctgggtg tggcggaccg    3600
ctatcaggac atagcgttgg ctacccgtga tattgctgaa gagcttggcg gcgaatgggc    3660
tgaccgcttc ctcgtgcttt acggtatcgc cgctcccgat tcgcagcgca tcgccttcta    3720
tcgccttctt gacgagttct ctgagcggg actctggggt tcgaaatgac cgaccaagcg    3780
acgcccaacc tgccatcacg agatttcgat tccaccgccg ccttctatga aaggttgggc    3840
ttcggaatcg ttttccggga cgccggctgg atgatcctcc agcgcgggga tctcatgctg    3900
gagttcttcg cccacccaa ccctggccct attattgggt ggactaacca tgggggaat     3960 tgccgctgga ataggaacag ggactactgc tctaatggcc actcagcaat tccagcagct    4020
ccaagccgca gtacaggatg atctcaggga ggttgaaaaa tcaatctcta acctagaaaa    4080
gtctctcact tccctgtctg aagttgtcct acagaatcga aggggcctag acttgttatt    4140
tctaaaagaa ggagggctgt gtgctgctct aaaagaagaa tgttgcttct atgcggacca    4200
cacaggacta gtgagagaca gcatggccaa attgagagag aggcttaatc agagacagaa    4260
actgtttgag tcaactcaag gatggtttga gggactgttt aacagatccc cttggtttac    4320
caccttgata tctaccatta tgggaccccct cattgtactc ctaatgattt tgctcttcgg    4380
accctgcatt cttaatcgat tagtccaatt tgttaaagac aggatatcag tggtccaggc    4440
tctagttttg actcaacaat atcaccagct gaagcctata gagtacgagc catagataaa    4500
ataaaagatt ttatttagtc tccagaaaaa gggggaatg aaagacccca cctgtaggtt    4560
tggcaagcta gcttaagtaa cgccattttg caaggcatgg aaaatacat aactgagaat     4620 agagaagttc agatcaaggt caggaacaga tggaacagct gaatatgggc caaacaggat    4680
atctgtggta agcagttcct gccccggctc agggccaaga acagatggaa cagctgaata    4740
tgggccaaac aggatatctg tggtaagcag ttcctgcccc ggctcagggc caagaacaga    4800
tggtccccag atgcggtcca gccctcagca gtttctagag aaccatcaga tgtttccagg    4860
gtgccccaag gacctgaaat gaccctgtgc cttatttgaa ctaaccaatc agttcgcttc    4920
tcgcttctgt tcgcgcgctt ctgctcccg agctcaataa aagagcccac aaccctcac     4980 tcggggcgcc agtcctccga ttgactgagt cgcccgggta cccgtgtatc caataaaccc    5040
```

```
tcttgcagtt gcatccgact tgtggtctcg ctgttccttg ggagggtctc ctctgagtga    5100
ttgactaccc gtcagcgggg gtctttcatt                                     5130

<210> SEQ ID NO 10
<211> LENGTH: 4661
<212> TYPE: DNA
<213> ORGANISM: Artificial Sequence
<220> FEATURE:
<223> OTHER INFORMATION: Synthetic

<400> SEQUENCE: 10
gatcagtcct gggtggtcat tgaaaggact gatgctgaag ttgaagctcc aatactttgg      60
ccacctgatg cgaagaactg actcatgtga taagaccctg atactgggaa agattgaagg     120
caggaggaga agggatgaca gaggatggaa gagttggatg gaatcaccaa ctcgatggac     180
atgagtttga gcaagcttcc aggagttggt aatgggcagg gaagcctggc gtgctgcagt     240
ccatggggtt gcaaagagtt ggacactact gagtgactga actgaactga tagtgtaatc     300
catggtacag aatataggat aaaaaagagg aagagtttgc cctgattctg aagagttgta     360
ggatataaaa gtttagaata cctttagttt ggaagtctta aattatttac ttaggatggg     420
tacccactgc aatataagaa atcaggcttt agagactgat gtagagagaa tgagccctgg     480
cataccagaa gctaacagct attggttata gctgttataa ccaatatata accaatatat     540
tggttatata gcatgaagct tgatgccagc aatttgaagg aaccatttag aactagtatc     600
ctaaactcta catgttccag gacactgatc ttaaagctca ggttcagaat cttgttttat     660
aggctctagg tgtatattgt ggggcttccc tggtggctca gatggtaaag tgtctgcctg     720
caatgtgggt gatctgggtt cgatccctgg cttgggaaga tcccctggag aaggaaatgg     780
caacccactc tagtactctt acctggaaaa ttccatggac agaggagcct tgtaagctac     840
agtccatggg attgcaaaga gttgaacaca actgagcaac taagcacagc acagtacagt     900
atacacctgt gaggtgaagt gaagtgaagg ttcaatgcag gtctcctgc attgcagaaa     960 gattctttac catctgagcc accagggaag cccaagaata ctggagtggg tagcctattc    1020
cttctccagg ggatcttccc atcccaggaa ttgaactgga gtctcctgca tttcaggtgg    1080
attcttcacc agctgaacta ccaggtggat actactccaa tattaaagtg cttaaagtcc    1140
agttttccca ccttttcccaa aaaggttggg tcactctttt ttaaccttct gtggcctact    1200
ctgaggctgt ctacaagctt atatatttat gaacacattt attgcaagtt gttagtttta    1260
gatttacaat gtggtatctg gctatttagt ggtattggtg gttggggatg ggaggctga     1320 tagcatctca gagggcagct agatactgtc atacacactt ttcaagttct ccattttttgt   1380 gaaatagaaa gtctctggat ctaagttata tgtgattctc agtctctgtg gtcatattct    1440
attctactcc tgaccactca acaaggaacc aagatatcaa gggacacttg ttttgtttca    1500
tgcctgggtt gagtgggcca tgacatatgt tctgggcctt gttacatggc tggattggtt    1560
ggacaagtgc cagctctgat cctgggactg tggcatgtga tgacatacac ccctctccca    1620
cattctgcat gtctctaggg gggaaggggg aagctcggta tagaaccttt attgtatttt    1680
ctgattgcct cacttcttat attgccccca tgcccttctt tgttcctcaa gtaaccagag    1740
acagtgcttc ccagaaccaa ccctacaaga aacaaagggc taaacaaagc caaatgggaa    1800
gcaggatcat ggtttgaact cttctggcc agagaacaat acctgctatg gactagatac    1860
tgggagaggg aaaggaaaag tagggtgaat tatggaagga agctggcagg ctcagcgttt    1920
```

```
ctgtcttggc atgaccagtc tctcttcatt ctcttcctag atgtagggct tggtaccaga    1980
gccccctgagg ctttctgcat gaatataaat atatgaaact gagtgatgct tccatttcag   2040
gttcttgggg gcgccgaatt cgagctcggt acccggggat ctcgagaagc tttaaccatg    2100
gaatggagct gggtctttct cttcttcctg tcagtaacta caggtgtcca ctcccaggtt    2160
cagttgcagc agtctgacgc tgagttggtg aaacctgggg cttcagtgaa gatttcctgc    2220
aaggcttctg gctacacctt cactgaccat gcaattcact gggtgaaaca gaaccctgaa    2280
cagggcctgg aatggattgg atatttttct cccggaaatg atgattttaa atacaatgag    2340
aggttcaagg gcaaggccac actgactgca gacaaatcct ccagcactgc ctacgtgcag    2400
ctcaacagcc tgacatctga ggattctgca gtgtatttct gtacaagatc cctgaatatg    2460
gcctactggg gtcaaggaac ctcagtcacc gtctcctcag gaggcggagg cagcggaggc    2520
ggtggctcgg gaggcggagg ctcggacatt gtgatgtcac agtctccatc ctccctacct    2580
gtgtcagttg gcgagaaggt tactttgagc tgcaagtcca gtcagagcct tttatatagt    2640
ggtaatcaaa agaactactt ggcctggtac cagcagaaac cagggcagtc tcctaaactg    2700
ctgatttact gggcatccgc tagggaatct ggggtccctg atcgcttcac aggcagtgga    2760
tctgggacag atttcactct ctccatcagc agtgtgaaga ctgaagacct ggcagtttat    2820
tactgtcagc agtattatag ctatcccctc acgttcggtg ctgggaccaa gctggtgctg    2880
aaacgggccg ccgagcccaa atctcctgac aaaactcaca catgcccacc gtgcccagca    2940
cctgaactcc tggggggacc gtcagtcttc ctcttccccc caaaacccaa ggacaccctc    3000
atgatctccc ggacccctga ggtcacatgc gtggtggtgg acgtgagcca cgaagaccct    3060
gaggtcaagt tcaactggta cgtggacggc gtggaggtgc ataatgccaa gacaaagccg    3120
cgggaggagc agtacaacag cacgtaccgt gtggtcagcg tcctcaccgt cctgcaccag    3180
gactggctga atggcaagga gtacaagtgc aaggtctcca acaaagccct cccagccccc    3240
atcgagaaaa ccatctccaa agccaaaggg cagccccgag aaccacaggt gtacaccctg    3300
cccccatccc gggatgagct gaccaagaac caggtcagcc tgacctgcct ggtcaaaggc    3360
ttctatccca gcgacatcgc cgtggagtgg gagagcaatg ggcagccgga gaacaactac    3420
aagaccacgc ctcccgtgct ggactccgac ggctccttct tcctctacag caagctcacc    3480
gtggacaaga gcaggtggca gcaggggaac gtcttctcat gctccgtgat gcatgaggct    3540
ctgcacaacc actacacgca gaagagcctc tccctgtctc cgggtaaagg aggcggatca    3600
ggaggtggcg cacctacttc aagttctaca agaaaaacac agctacaact ggagcattta    3660
ctgctggatt tacagatgat tttgaatgga attaataatt acaagaatcc caaactcacc    3720
aggatgctca catttaagtt ttacatgccc aagaaggcca cagaactgaa acatcttcag    3780
tgtctagaag aagaactcaa acctctggag gaagtgctaa atttagctca aagcaaaaac    3840
tttcacttaa gacccaggga cttaatcagc aatatcaacg taatagttct ggaactaaag    3900
ggatctgaaa caacattcat gtgtgaatat gctgatgaga cagcaaccat tgtagaattt    3960
ctgaacagat ggattacctt ttgtcaaagc atcatctcaa cactaacttg aagcttgtta    4020
acatcgataa aataaaagat tttatttagt ctccagaaaa agggggaat gaaagacccc    4080
acctgtaggt ttggcaagct agcttaagta acgccatttt gcaaggcatg gaaaaataca    4140
taactgagaa tagagaagtt cagatcaagg tcaggaacag atggaacagc tgaatatggg    4200
ccaaacagga tatctgtggt aagcagttcc tgccccggct cagggccaag aacagatgga    4260
acagctgaat atgggccaaa caggatatct gtggtaagca gttcctgccc cggctcaggg    4320
```

```
ccaagaacag atggtcccca gatgcggtcc agccctcagc agtttctaga gaaccatcag      4380
atgtttccag ggtgccccaa ggacctgaaa tgaccctgtg ccttatttga actaaccaat      4440
cagttcgctt ctcgcttctg ttcgcgcgct tctgctcccc gagctcaata aaagagccca      4500
caacccctca ctcggggcgc cagtcctccg attgactgag tcgcccgggt acccgtgtat      4560
ccaataaacc ctcttgcagt tgcatccgac ttgtggtctc gctgttcctt gggagggtct      4620
cctctgagtg attgactacc cgtcagcggg ggtctttcat t                          4661
```

<210> SEQ ID NO 11
<211> LENGTH: 5691
<212> TYPE: DNA
<213> ORGANISM: Artificial Sequence
<220> FEATURE:
<223> OTHER INFORMATION: Synthetic

<400> SEQUENCE: 11

```
gatcagtcct gggtggtcat tgaaaggact gatgctgaag ttgaagctcc aatactttgg        60
ccacctgatg cgaagaactg actcatgtga taagaccctg atactgggaa agattgaagg       120
caggaggaga agggatgaca gaggatggaa gagttggatg gaatcaccaa ctcgatggac       180
atgagtttga gcaagcttcc aggagttggt aatgggcagg gaagcctggc gtgctgcagt       240
ccatggggtt gcaaagagtt ggacactact gagtgactga actgaactga tagtgtaatc       300
catggtacag aatataggat aaaaagagg aagagtttgc cctgattctg aagagttgta       360
ggatataaaa gtttagaata cctttagttt ggaagtctta aattatttac ttaggatggg       420
tacccactgc aatataagaa atcaggcttt agagactgat gtagagagaa tgagccctgg       480
cataccagaa gctaacagct attggttata gctgttataa ccaatatata accaatatat       540
tggttatata gcatgaagct tgatgccagc aatttgaagg aaccatttag aactagtatc       600
ctaaactcta catgttccag acactgatc ttaaagctca ggttcagaat cttgttttat       660
aggctctagg tgtatattgt ggggcttccc tggtggctca gatggtaaag tgtctgcctg       720
caatgtgggt gatctgggtt cgatccctgg cttgggaaga tccctggag aaggaaatgg       780 caacccactc tagtactctt acctggaaaa ttccatggac agaggagcct tgtaagctac       840
agtccatggg attgcaaaga gttgaacaca actgagcaac taagcacagc acagtacagt       900
atacacctgt gaggtgaagt gaagtgaagg ttcaatgcag ggtctcctgc attgcagaaa       960
gattctttac catctgagcc accagggaag cccaagaata ctggagtggg tagcctattc      1020
cttctccagg ggatcttccc atcccaggaa ttgaactgga gtctcctgca tttcaggtgg      1080
attcttcacc agctgaacta ccaggtggat actactccaa tattaaagtg cttaaagtcc      1140
agttttccca cctttcccaa aaaggttggg tcactctttt ttaaccttct gtggcctact      1200
ctgaggctgt ctacaagctt atatatttat gaacacattt attgcaagtt gttagttta      1260 gatttacaat gtggtatctg gctatttagt ggtattggtg gttggggatg ggaggctga      1320 tagcatctca gagggcagct agatactgtc atacacactt ttcaagttct ccattttgt      1380 gaaatagaaa gtctctggat ctaagttata tgtgattctc agtctctgtg gtcatattct      1440
attctactcc tgaccactca acaaggaacc aagatatcaa gggacacttg ttttgtttca      1500
tgcctgggtt gagtgggcca tgacatatgt tctgggcctt gttacatggc tggattggtt      1560
ggacaagtgc cagctctgat cctgggactg tggcatgtga tgcatacac ccctctccca      1620 cattctgcat gtctctaggg gggaaggggg aagctcggta tagaaccttt attgtattt      1680
```

```
ctgattgcct cacttcttat attgccccca tgcccttctt tgttcctcaa gtaaccagag    1740
acagtgcttc ccagaaccaa ccctacaaga aacaaagggc taaacaaagc caaatgggaa    1800
gcaggatcat ggtttgaact ctttctggcc agagaacaat acctgctatg gactagatac    1860
tgggagaggg aaaggaaaag tagggtgaat tatggaagga agctggcagg ctcagcgttt    1920
ctgtcttggc atgaccagtc tctcttcatt ctcttcctag atgtagggct tggtaccaga    1980 gccctgagg ctttctgcat gaatataaat atatgaaact gagtgatgct tccatttcag     2040
gttcttgggg gcgccgaatt cgagctcggt acccggggat ctcgacggat ccgattactt    2100
actggcaggt gctgggggct tccgagacaa tcgcgaacta ctacaccaca caacaccgcc    2160
tcgaccaggg tgagatatcg gccggggacg cggcggtggt aattacaagc gagatccgat    2220
tacttactgg caggtgctgg gggcttccga gacaatcgcg aacatctaca ccacacaaca    2280
ccgcctcgac cagggtgaga tatcggccgg ggacgcggcg gtggtaatta caagcgagat    2340
ctcgagttaa cagatctagg cctcctaggt cgacggatcc ccgggaattc ggcgccgcca    2400
ccatgatgtc ctttgtctct ctgctcctgg taggcatcct attccatgcc acccaggccc    2460
aggtccaact gcagcagtct gggcctgagc tggtgaagcc tgggacttca gtgaggatat    2520
cctgcaaggc ttctggctac accttcacaa gctactattt acactgggtg aagcagaggc    2580
ctggacaggg acttgagtgg attgcatgga tttatcctgg aaatgttatt actacgtaca    2640
atgagaagtt caagggcaag gccacactga ctgcagacaa atcctccagc acagcctaca    2700
tgcacctcaa cagcctgacc tctgaggact ctgcggtcta tttctgtgca agggtgacc    2760 atgatcttga ctactggggc caaggcacca ctctcacagt ctcctcagcc aaaacgacac    2820
ccccatctgt ctatccactg gcccctggat ctgctgccca aactaactcc atggtgaccc    2880
tgggatgcct ggtcaagggc tatttccctg agccagtgac agtgacctgg aactctggat    2940
ccctgtccag cggtgtgcac accttcccag ctgtcctgca gtctgacctc tacactctga    3000
gcagctcagt gactgtcccc tccagcacct ggcccagcga gaccgtcacc tgcaacgttg    3060
cccacccggc cagcagcacc aaggtggaca agaaaattgt gcccagggat tgtactagtg    3120
gaggtggagg tagctaaggg agatctcgac ggatcccgg gaattcgccc ctctccctcc    3180
ccccccccta cgttactgg ccgaagccgc ttggaataag gccggtgtgc gtttgtctat    3240
atgttatttt ccaccatatt gccgtctttt ggcaatgtga gggcccggaa acctggccct    3300
gtcttcttga cgagcattcc tagggggtctt tcccctctcg ccaaaggaat gcaaggtctg    3360
ttgaatgtcg tgaaggaagc agttcctctg gaagcttctt gaagacaaac aacgtctgta    3420
gcgacccttt gcaggcagcg gaacccccca cctggcgaca ggtgcctctg cggccaaaag    3480
ccacgtgtat aagatacacc tgcaaaggcg gcacaacccc agtgccacgt tgtgagttgg    3540
atagttgtgg aaagagtcaa atggctctcc tcaagcgtat tcaacaaggg gctgaaggat    3600
gcccagaagg tacccattg tatgggatct gatctgggc tcggtgcac atgctttaca      3660 tgtgtttagt cgaggttaaa aaaacgtcta ggccccccga accacgggga cgtggttttc    3720
ctttgaaaaa cacgatgata atatggcctc ctttgtctct ctgctcctgg taggcatcct    3780
attccatgcc acccaggccg acattgtgct gacacaatct ccagcaatca tgtctgcatc    3840
tccaggggag aaggtcacca tgacctgcag tgccacctca agtgtaagtt acatacactg    3900
gtaccagcag aagtcaggca cctcccccaa aagatggatt tatgacacat ccaaactggc    3960
ttctggagtc cctgctcgct tcagtggcag tgggtctggg acctctcact ctctcacact    4020
cagcagcatg gaggctgaag atgctgccac ttattactgc cagcagtggg gtagttacct    4080
```

```
cacgttcggt gcggggacca agctggagct gaaacgggct gatgctgcac caactgtatc   4140
catcttccca ccatccagtg agcagttaac atctggaggt gcctcagtcg tgtgcttctt   4200
gaacaacttc tacccaaaag acatcaatgt caagtggaag attgatggca gtgaacgaca   4260
aaatggcgtc ctgaacagtt ggactgatca ggacagcaaa gacagcacct acagcatgag   4320
cagcaccctc acgttgacca aggacgagta tgaacgacat aacagctata cctgtgaggc   4380
cactcacaag acatcaactt cacccattgt caagagcttc aacaggaatg agtgttaata   4440
ggggagatct cgacatcgat aatcaacctc tggattacaa atttgtgaa agattgactg    4500 gtattcttaa ctatgttgct ccttttacgc tatgtggata cgctgcttta atgcctttgt   4560
atcatgctat tgcttcccgt atggctttca ttttctcctc cttgtataaa tcctggttgc   4620
tgtctcttta tgaggagttg tggcccgttg tcaggcaacg tggcgtggtg tgcactgtgt   4680
ttgctgacgc aacccccact ggttggggca ttgccaccac ctgtcagctc ctttccggga   4740
ctttcgcttt cccccctccct attgccacgg cggaactcat cgccgcctgc cttgcccgct   4800
gctggacagg ggctcggctg ttgggcactg acaattccgt ggtgttgtcg gggaaatcat   4860
cgtccttttc ttggctgctc gcctgtgttg ccacctggat tctgcgcggg acgtccttct   4920
gctacgtccc ttcggccctc aatccagcgg accttccttc ccgcggcctg ctgccggctc   4980
tgcggcctct tccgcgtctt cgccttcgcc ctcagacgag tcggatctcc ctttgggccg   5040
cctccccgcc tgatcgataa aataaaagat tttatttagt ctccagaaaa agggggaat    5100 gaaagacccc acctgtaggt ttggcaagct agcttaagta acgccatttt gcaaggcatg   5160
gaaaaataca taactgagaa tagagaagtt cagatcaagg tcaggaacag atggaacagc   5220
tgaatatggg ccaaacagga tatctgtggt aagcagttcc tgccccggct cagggccaag   5280
aacagatgga acagctgaat atgggccaaa caggatatct gtggtaagca gttcctgccc   5340
cggctcaggg ccaagaacag atggtcccca gatgcggtcc agccctcagc agtttctaga   5400
gaaccatcag atgtttccag ggtgccccaa ggacctgaaa tgaccctgtg ccttatttga   5460
actaaccaat cagttcgctt ctcgcttctg ttcgcgcgct tctgctcccc gagctcaata   5520
aaagagccca aaccccctca ctcggggcgc cagtcctccg attgactgag tcgcccgggt   5580
acccgtgtat ccaataaacc ctcttgcagt tgcatccgac ttgtggtctc gctgttcctt   5640
gggagggtct cctctgagtg attgactacc cgtcagcggg ggtctttcat t             5691
```

<210> SEQ ID NO 12
<211> LENGTH: 668
<212> TYPE: DNA
<213> ORGANISM: Artificial Sequence
<220> FEATURE:
<223> OTHER INFORMATION: Synthetic

<400> SEQUENCE: 12

```
ggaattcgcc cctctcccctc cccccccccct aacgttactg gccgaagccg cttggaataa     60
ggccggtgtg cgtttgtcta tatgttattt tccaccatat tgccgtcttt tggcaatgtg    120
agggcccgga aacctggccc tgtcttcttg acgagcattc ctaggggtct ttcccctctc    180
gccaaaggaa tgcaaggtct gttgaatgtc gtgaaggaag cagttcctct ggaagcttct    240
tgaagacaaa caacgtctgt agcgaccctt gcaggcagc ggaaccccccc acctggcgac     300 aggtgcctct gcggccaaaa gccacgtgta taagatacac ctgcaaaggc ggcacaaccc    360
cagtgccacg ttgtgagttg gatagttgtg gaaagagtca aatggctctc ctcaagcgta    420
```

```
ttcaacaagg ggctgaagga tgcccagaag gtaccccatt gtatgggatc tgatctgggg    480
cctcggtgca catgctttac atgtgtttag tcgaggttaa aaaaacgtct aggcccccg     540 aaccacgggg acgtggtttt cctttgaaaa acacgatgat aatatggcct tgctcatcct    600
tacctgtctt gtggctgttg ctcttgccgg cgccatggga tatctagatc tcgagctcgc    660
gaaagctt                                                             668
```

<210> SEQ ID NO 13
<211> LENGTH: 6255
<212> TYPE: DNA
<213> ORGANISM: Artificial Sequence
<220> FEATURE:
<223> OTHER INFORMATION: Synthetic

<400> SEQUENCE: 13

```
tttgaaagac cccacccgta ggtggcaagc tagcttaagt aacgccactt tgcaaggcat      60
ggaaaaatac ataactgaga atagaaaagt tcagatcaag gtcaggaaca aagaaacagc     120
tgaataccaa acaggatatc tgtggtaagc ggttcctgcc ccggctcagg gccaagaaca     180
gatgagacag ctgagtgatg ggccaaacag gatatctgtg gtaagcagtt cctgccccgg     240
ctcggggcca agaacagatg gtccccagat gcggtccagc cctcagcagt ttctagtgaa     300
tcatcagatg tttccaggt gccccaagga cctgaaaatg accctgtacc ttatttgaac      360
taaccaatca gttcgcttct cgcttctgtt cgcgcgcttc cgctctccga gctcaataaa     420
agagcccaca cccctcact cggcgcgcca gtcttccgat agactgcgtc gcccgggtac      480
ccgtattccc aataaagcct cttgctgttt gcatccgaat cgtggtctcg ctgttccttg     540
ggagggtctc ctctgagtga ttgactaccc acgacggggg tctttcattt gggggctcgt     600
ccgggatttg gagacccctg cccagggacc accgaccac caccgggagg taagctggcc      660
agcaacttat ctgtgtctgt ccgattgtct agtgtctatg tttgatgtta tgcgcctgcg     720
tctgtactag ttagctaact agctctgtat ctggcggacc cgtggtggaa ctgacgagtt     780
ctgaacaccc ggccgcaacc ctgggagacg tcccagggac tttgggggcc gtttttgtgg     840
cccgacctga ggaagggagt cgatgtggaa tccgaccccg tcaggatatg tggttctggt     900
aggagacgag aacctaaaac agttcccgcc tccgtctgaa ttttttgctttc ggtttggaa     960 ccgaagccgc gcgtcttgtc tgctgcagcg ctgcagcatc gttctgtgtt gtctctgtct    1020
gactgtgttt ctgtatttgt ctgaaaatta gggccagact gttaccactc ccttaagttt    1080
gaccttaggt cactggaaag atgtcgagcg atcgctcac aaccagtcgg tagatgtcaa      1140
gaagagacgt tgggttacct tctgctctgc agaatggcca acctttaacg tcggatggcc    1200
gcgagacggc accttaacc gagacctcat cacccaggtt aagatcaagg tcttttcacc      1260
tggcccgcat ggacacccag accaggtccc ctacatcgtg acctgggaag ccttggcttt    1320
tgacccccct ccctgggtca agcccttttgt acaccctaag cctccgcctc ctcttcctcc    1380
atccgccccg tctctccccc ttgaacctcc tcgttcgacc ccgcctcgat cctcccttta    1440
tccagccctc actccttctc taggcgccgg aattccgatc tgatcaagag acaggatgag    1500
gatcgtttcg catgattgaa caagatggat tgcacgcagg ttctccggcc gcttgggtgg    1560
agaggctatt cggctatgac tgggcacaac agacaatcgg ctgctctgat gccgccgtgt    1620
tccggctgtc agcgcagggg cgcccggttc tttttgtcaa gaccgacctg tccggtgccc    1680
tgaatgaact gcaggacgag gcagcgcggc tatcgtggct ggccacgacg ggcgttcctt    1740
gcgcagctgt gctcgacgtt gtcactgaag cgggaaggga ctggctgcta ttgggcgaag    1800
```

```
tgccggggca ggatctcctg tcatctcacc ttgctcctgc cgagaaagta tccatcatgg    1860
ctgatgcaat gcggcggctg catacgcttg atccggctac ctgcccattc gaccaccaag    1920
cgaaacatcg catcgagcga gcacgtactc ggatggaagc cggtcttgtc gatcaggatg    1980
atctggacga agagcatcag gggctcgcgc cagccgaact gttcgccagg ctcaaggcgc    2040
gcatgcccga cggcgaggat ctcgtcgtga cccatggcga tgcctgcttg ccgaatatca    2100
tggtggaaaa tggccgcttt tctggattca tcgactgtgg ccggctgggt gtggcggacc    2160
gctatcagga catagcgttg gctacccgtg atattgctga agagcttggc ggcgaatggg    2220
ctgaccgctt cctcgtgctt tacggtatcg ccgctcccga ttcgcagcgc atcgccttct    2280
atcgccttct tgacgagttc ttctgagcgg actctgggg ttcgaaatga ccgaccaagc    2340
gacgcccaac ctgccatcac gagatttcga ttccaccgcc gccttctatg aaaggttggg    2400
cttcggaatc gttttccggg acgccggctg gatgatcctc cagcgcgggg atctcatgct    2460
ggagttcttc gcccacccg ggctcgatcc cctcgcgagt tggttcagct gctgcctgag    2520
gctggacgac ctcgcggagt tctaccggca gtgcaaatcc gtcggcatcc aggaaaccag    2580
cagcggctat ccgcgcatcc atgccccga actgcaggag tggggaggca cgatggccgc    2640
tttggtcgag gcggatccgg ccattagcca tattattcat tggttatata gcataaatca    2700
atattggcta ttgccattg catacgttgt atccatatca taatatgtac atttatattg    2760
gctcatgtcc aacattaccg ccatgttgac attgattatt gactagttat taatagtaat    2820
caattacggg gtcattagtt catagcccat atatggagtt ccgcgttaca aacttacgg     2880 taaatggccc gcctggctga ccgcccaacg accccgccc attgacgtca ataatgacgt     2940
atgttcccat agtaacgcca ataggggactt tccattgacg tcaatgggtg gagtatttac    3000
ggtaaactgc ccacttggca gtacatcaag tgtatcatat gccaagtacg ccccctattg    3060
acgtcaatga cggtaaatgg cccgcctggc attatgccca gtacatgacc ttatgggact    3120
ttcctacttg gcagtacatc tacgtattag tcatcgctat taccatggtg atgcggtttt    3180
ggcagtacat caatgggcgt ggatagcggt ttgactcacg gggatttcca agtctccacc    3240
ccattgacgt caatgggagt ttgttttggc accaaaatca acgggacttt ccaaaatgtc    3300
gtaacaactc cgccccattg acgcaaatgg gcggtaggca tgtacggtgg gaggtctata    3360
taagcagagc tcgtttagtg aaccgtcaga tcgcctggag acgccatcca cgctgttttg    3420
acctccatag aagacaccgg gaccgatcca gcctccgcgg ccccaagctt ctcgacggat    3480
ccccgggaat tcaggccatc gatcccgccg ccaccatgga atggagctgg gtctttctct    3540
tcttcctgtc agtaactaca ggtgtccact ccgacatcca gatgacccag tctccagcct    3600
ccctatctgc atctgtggga gaaactgtca ctatcacatg tcgagcaagt gggaatattc    3660
acaattattt agcatggtat cagcagaaac agggaaaatc tcctcagctc ctggtctata    3720
atgcaaaaac cttagcagat ggtgtgccat caaggttcag tggcagtgga tcaggaacac    3780
aatattctct caagatcaac agcctgcagc ctgaagattt tggagttat tactgtcaac     3840 attttggag tactccgtgg acgttcggtg gaggcaccaa gctggaaatc aaacgggctg     3900
atgctgcacc aactgtatcc atcttcccac catccagtga gcagttaaca tctggaggtg    3960
cctcagtcgt gtgcttcttg aacaacttct acccaaaaga catcaatgtc aagtggaaga    4020
ttgatggcag tgaacgacaa aatggcgtcc tgaacagttg gactgatcag gacagcaaag    4080
acagcaccta cagcatgagc agcaccctca cattgaccaa ggacgagtat gaacgacata    4140
```

-continued

```
acagctatac ctgtgaggcc actcacaaga catcaacttc acccattgtc aagagcttca    4200
acaggaatga gtgttgaaag catcgatttc ccctgaattc gcccctctcc ctccccccc     4260
cctaacgtta ctggccgaag ccgcttggaa taaggccggt gtgcgtttgt ctatatgtta    4320
ttttccacca tattgccgtc ttttggcaat gtgagggccc ggaaacctgg ccctgtcttc    4380
ttgacgagca ttcctagggg tctttcccct ctcgccaaag gaatgcaagg tctgttgaat    4440
gtcgtgaagg aagcagttcc tctggaagct tcttgaagac aaacaacgtc tgtagcgacc    4500
ctttgcaggc agcggaaccc cccacctggc gacaggtgcc tctgcggcca aaagccacgt    4560
gtataagata cacctgcaaa ggcggcacaa ccccagtgcc acgttgtgag ttggatagtt    4620
gtggaaagag tcaaatggct ctcctcaagc gtattcaaca aggggctgaa ggatgcccag    4680
aaggtacccc attgtatggg atctgatctg gggcctcggt gcacatgctt acatgtgtt     4740
tagtcgaggt taaaaaaacg tctaggcccc ccgaaccacg gggacgtggt tttcctttga    4800
aaaacacgat gataatatgg cctcctttgt ctctctgctc ctggtaggca tcctattcca    4860
tgccacccag gccgaggttc agcttcagca gtctgggggca gagcttgtga agccaggggc   4920
ctcagtcaag ttgtcctgca cagcttctgg cttcaacatt aaagacacct ttatgcactg    4980
ggtgaagcag aggcctgaac agggcctgga gtggattgga aggattgatc ctgcgaatgg    5040
gaatactgaa tatgacccga agttccaggg caaggccact ataacagcag acacatcctc    5100
caacacagtc aacctgcagc tcagcagcct gacatctgag gacactgccg tctattactg    5160
tgctagtgga ggggaactgg ggtttcctta ctggggccaa gggactctgg tcactgtctc    5220
tgcagccaaa acgacacccc catctgtcta tccactggcc cctggatctg ctgcccaaac    5280
taactccatg gtgaccctgg gatgcctggt caagggctat ttccctgagc cagtgacagt    5340
gacctggaac tctggatccc tgtccagcgg tgtgcacacc ttcccagctg tcctgcagtc    5400
tgacctctac actctgagca gctcagtgac tgtcccctcc agcacctggc cagcgagac     5460
cgtcacctgc aacgttgccc acccggccag cagcaccaag gtggacaaga aaattgtgcc    5520
cagggattgt actagtggag gtggaggtag ccaccatcac catcaccatt aatctagagt    5580
taagcggccg tcgagatcta ggcctcctag gtcgacatcg ataaaataaa agattttatt    5640
tagtctccag aaaaaggggg gaatgaaaga ccccacctgt aggtttggca agctagctta    5700
agtaacgcca ttttgcaagg catggaaaaa tacataactg agaatagaga agttcagatc    5760
aaggtcagga acagatggaa cagctgaata tgggccaaac aggatatctg tggtaagcag    5820
ttcctgcccc ggctcagggc caagaacaga tggaacagct gaatatgggc caaacaggat    5880
atctgtggta agcagttcct gccccggctc agggccaaga acagatggtc ccagatgcg     5940
gtccagcct cagcagtttc tagagaacca tcagatgttt ccagggtgcc caaggacct     6000
gaaatgaccc tgtgccttat ttgaactaac caatcagttc gcttctcgct tctgttcgcg    6060
cgcttctgct ccccgagctc aataaaagag cccacaaccc ctcactcggg gcgccagtcc    6120
tccgattgac tgagtcgccc gggtacccgt gtatccaata aaccctcttg cagttgcatc    6180
cgacttgtgg tctcgctgtt ccttgggagg gtctcctctg agtgattgac tacccgtcag    6240
cgggggtctt tcatt                                                    6255
```

<210> SEQ ID NO 14
<211> LENGTH: 43
<212> TYPE: DNA
<213> ORGANISM: Artificial Sequence
<220> FEATURE:
<223> OTHER INFORMATION: Synthetic

<400> SEQUENCE: 14
ctttgaaaaa cacgatgata atatggcctc ctttgtctct ctg                    43

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
ttcgcgagct cgagatctag atatcccatg                                   30

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
ctacaggtgt ccacgtcgac atccagctga cccag                             35

<210> SEQ ID NO 17
<211> LENGTH: 34
<212> TYPE: DNA
<213> ORGANISM: Artificial Sequence
<220> FEATURE:
<223> OTHER INFORMATION: Synthetic

<400> SEQUENCE: 17
ctgcagaata gatctctaac actctcccct gttg                              34

<210> SEQ ID NO 18
<211> LENGTH: 51
<212> TYPE: DNA
<213> ORGANISM: Artificial Sequence
<220> FEATURE:
<223> OTHER INFORMATION: Synthetic

<400> SEQUENCE: 18
cagtgtgatc tcgagaattc aggacctcac catgggatgg agctgtatca t           51

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
aggctgtatt ggtggattcg tct                                          23

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
agcttctcga gttaacagat ctaggcctcc taggtcgaca t                      41

<210> SEQ ID NO 21

<211> LENGTH: 39
<212> TYPE: DNA
<213> ORGANISM: Artificial Sequence
<220> FEATURE:
<223> OTHER INFORMATION: Synthetic

<400> SEQUENCE: 21
cgatgtcgac ctaggaggcc tagatctgtt aactcgaga        39

<210> SEQ ID NO 22
<211> LENGTH: 64
<212> TYPE: DNA
<213> ORGANISM: Artificial Sequence
<220> FEATURE:
<223> OTHER INFORMATION: Synthetic

<400> SEQUENCE: 22
cgaggctctg cacaaccact acacgcagaa gagcctctcc ctgtctcccg ggaaatgaaa        60
gccg        64

<210> SEQ ID NO 23
<211> LENGTH: 72
<212> TYPE: DNA
<213> ORGANISM: Artificial Sequence
<220> FEATURE:
<223> OTHER INFORMATION: Synthetic

<400> SEQUENCE: 23
aattcggctt tcatttcccg ggagacaggg agaggctctt ctgcgtgtag tggttgtgca        60
gagcctcgtg ca        72

<210> SEQ ID NO 24
<211> LENGTH: 41
<212> TYPE: DNA
<213> ORGANISM: Artificial Sequence
<220> FEATURE:
<223> OTHER INFORMATION: Synthetic

<400> SEQUENCE: 24
aaagcatatg ttctgggcct tgttacatgg ctggattggt t        41

<210> SEQ ID NO 25
<211> LENGTH: 54
<212> TYPE: DNA
<213> ORGANISM: Artificial Sequence
<220> FEATURE:
<223> OTHER INFORMATION: Synthetic

<400> SEQUENCE: 25
tgaattcggc gcccccaaga acctgaaatg gaagcatcac tcagtttcat atat        54

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26
ctacaggtgt ccacgtcgac atccagctga cccag        35

<210> SEQ ID NO 27
<211> LENGTH: 34
<212> TYPE: DNA
<213> ORGANISM: Artificial Sequence

```
<220> FEATURE:
<223> OTHER INFORMATION: Synthetic

<400> SEQUENCE: 27
ctgcagaata gatctctaac actctcccct gttg                                    34

<210> SEQ ID NO 28
<211> LENGTH: 51
<212> TYPE: DNA
<213> ORGANISM: Artificial Sequence
<220> FEATURE:
<223> OTHER INFORMATION: Synthetic

<400> SEQUENCE: 28
cagtgtgatc tcgagaattc aggacctcac catgggatgg agctgtatca t                 51

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
gtgtcttcgg gtctcaggct gt                                                 22

<210> SEQ ID NO 30
<211> LENGTH: 41
<212> TYPE: DNA
<213> ORGANISM: Artificial Sequence
<220> FEATURE:
<223> OTHER INFORMATION: Synthetic

<400> SEQUENCE: 30
agcttctcga gttaacagat ctaggcctcc taggtcgaca t                            41

<210> SEQ ID NO 31
<211> LENGTH: 39
<212> TYPE: DNA
<213> ORGANISM: Artificial Sequence
<220> FEATURE:
<223> OTHER INFORMATION: Synthetic

<400> SEQUENCE: 31
cgatgtcgac ctaggaggcc tagatctgtt aactcgaga                               39

<210> SEQ ID NO 32
<211> LENGTH: 64
<212> TYPE: DNA
<213> ORGANISM: Artificial Sequence
<220> FEATURE:
<223> OTHER INFORMATION: Synthetic

<400> SEQUENCE: 32
cgaggctctg cacaaccact acacgcagaa gagcctctcc ctgtctcccg ggaaatgaaa        60
gccg                                                                    64

<210> SEQ ID NO 33
<211> LENGTH: 72
<212> TYPE: DNA
<213> ORGANISM: Artificial Sequence
<220> FEATURE:
<223> OTHER INFORMATION: Synthetic

<400> SEQUENCE: 33
```

```
aattcggctt tcatttcccg ggagacaggg agaggctctt ctgcgtgtag tggttgtgca    60
gagcctcgtg ca                                                         72

<210> SEQ ID NO 34
<211> LENGTH: 9511
<212> TYPE: DNA
<213> ORGANISM: Artificial Sequence
<220> FEATURE:
<223> OTHER INFORMATION: Synthetic

<400> SEQUENCE: 34
gaattaattc ataccagatc accgaaaact gtcctccaaa tgtgtccccc tcacactccc    60
aaattcgcgg gcttctgcct cttagaccac tctaccctat tccccacact caccggagcc   120
aaagccgcgg cccttccgtt tctttgcttt tgaaagaccc cacccgtagg tggcaagcta   180
gcttaagtaa cgccactttg caaggcatgg aaaatacat aactgagaat agaaaagttc    240
agatcaaggt caggaacaaa gaaacagctg aataccaaac aggatatctg tggtaagcgg   300
ttcctgcccc ggctcagggc caagaacaga tgagacagct gagtgatggg ccaaacagga   360
tatctgtggt aagcagttcc tgccccggct cggggccaag aacagatggt ccccagatgc   420
ggtccagccc tcagcagttt ctagtgaatc atcagatgtt ccagggtgc cccaaggacc    480 tgaaaatgac cctgtacctt atttgaacta accaatcagt tcgcttctcg cttctgttcg   540
cgcgcttccg ctctccgagc tcaataaaag agcccacaac ccctcactcg gcgcgccagt   600
cttccgatag actgcgtcgc ccgggtaccc gtattcccaa taaagcctct tgctgtttgc   660
atccgaatcg tggtctcgct gttccttggg agggtctcct ctgagtgatt gactacccac   720 gacggggtc tttcatttgg gggctcgtcc gggatttgga daccoctgcc cagggaccac    780 cgacccacca ccgggaggta agctggccag caacttatct gtgtctgtcc gattgtctag   840
tgtctatgtt tgatgttatg cgcctgcgtc tgtactagtt agctaactag ctctgtatct   900
ggcggacccg tggtggaact gacgagttct gaacacccgg ccgcaaccct gggagacgtc   960
ccagggactt tgggggccgt ttttgtggcc cgacctgagg aagggagtcg atgtggaatc  1020
cgaccccgtc aggatatgtg gttctggtag gagacgagaa cctaaaacag ttcccgcctc  1080
cgtctgaatt tttgctttcg gtttggaacc gaagccgcgc gtcttgtctg ctgcagcgct  1140
gcagcatcgt tctgtgttgt ctctgtctga ctgtgtttct gtatttgtct gaaaattagg  1200
gccagactgt taccactccc ttaagtttga ccttaggtca ctggaaagat gtcgagcgga  1260
tcgctcacaa ccagtcggta gatgtcaaga agagacgttg ggttaccttc tgctctgcag  1320
aatggccaac ctttaacgtc ggatggccgc gagacggcac ctttaaccga gacctcatca  1380
cccaggttaa gatcaaggtc ttttcacctg gcccgcatgg acacccagac caggtccccc  1440
acatcgtgac ctgggaagcc ttggcttttg accccctcc ctgggtcaag ccctttgtac   1500
accctaagcc tccgcctcct cttcctccat ccgccccgtc tctccccctt gaacctcctc  1560
gttcgacccc gcctcgatcc tccctttatc cagccctcac tccttctcta ggcgccggaa  1620
ttccgatctg atcaagagac aggatgaggg agcttgtata tccattttcg gatctgatca  1680
gcacgtgttg acaattaatc atcggcatag tatatcggca tagtataata cgacaaggtg  1740
aggaactaaa ccatggccaa gcctttgtct caagaagaat ccaccctcat tgaaagagca  1800
acggctacaa tcaacagcat ccccatctct gaagactaca cgtcgccag cgcagctctc  1860 tctagcgacg gccgcatctt cactggtgtc aatgtatatc attttactgg gggaccttgt  1920
gcagaactcg tggtgctggg cactgctgct gctgcggcag ctggcaacct gacttgtatc  1980
```

```
gtcgcgatcg gaaatgagaa caggggcatc ttgagcccct gcggacggtg tcgacaggtg    2040
cttctcgatc tgcatcctgg gatcaaagcg atagtgaagg acagtgatgg acagccgacg    2100
gcagttggga ttcgtgaatt gctgccctct ggttatgtgt gggagggcta agcacttcgt    2160
ggccgaggag caggactgac acgtgctacg agatttcgat tccaccgccg ccttctatga    2220
aaggttgggc ttcggaatcg ttttccggga cgccggctgg atgatcctcc agcgcgggga    2280
tctcatgctg gagttcttcg cccacccccaa cttgtttatt gcagcttata atggttacaa    2340
ataaagcaat agcatcacaa atttcacaaa taaagcattt ttttcactgc attctagttg    2400
tggtttgtcc aaactcatca atgtatctta tcatgtctgt acgagttggt tcagctgctg    2460
cctgaggctg gacgacctcg cggagttcta ccggcagtgc aaatccgtcg gcatccagga    2520
aaccagcagc ggctatccgc gcatccatgc ccccgaactg caggagtggg gaggcacgat    2580
ggccgctttg gtcgaggcgg atccggccat tagccatatt attcattggt tatatagcat    2640
aaatcaatat tggctattgg ccattgcata cgttgtatcc atatcataat atgtacattt    2700
atattggctc atgtccaaca ttaccgccat gttgacattg attattgact agttattaat    2760
agtaatcaat tacggggtca ttagttcata gcccatatat ggagttccgc gttacataac    2820
ttacggtaaa tggcccgcct ggctgaccgc ccaacgaccc ccgcccattg acgtcaataa    2880
tgacgtatgt tcccatagta acgccaatag ggactttcca ttgacgtcaa tgggtggagt    2940
atttacggta aactgcccac ttggcagtac atcaagtgta tcatatgcca agtacgcccc    3000
ctattgacgt caatgacggt aaatggcccg cctggcatta tgcccagtac atgaccttat    3060
gggactttcc tacttggcag tacatctacg tattagtcat cgctattacc atggtgatgc    3120
ggttttggca gtacatcaat gggcgtggat agcggtttga ctcacgggga tttccaagtc    3180
tccaccccat tgacgtcaat gggagtttgt tttggcacca aaatcaacgg gactttccaa    3240
aatgtcgtaa caactccgcc ccattgacgc aaatgggcgg taggcatgta cggtgggagg    3300
tctatataag cagagctcgt ttagtgaacc gtcagatcgc ctggagacgc catccacgct    3360
gttttgacct ccatagaaga caccgggacc gatccagcct ccgcggcccc aagcttctcg    3420
agttaacaga tctaggctgg cacgacaggt ttcccgactg gaaagcgggc agtgagcgca    3480
acgcaattaa tgtgagttag ctcactcatt aggcacccca ggctttacac tttatgcttc    3540
cggctcgtat gttgtgtgga attgtgagcg ataacaatt tcacacagga aacagctatg    3600
accatgatta cgccaagctt ggctgcaggt cgacggatcc actagtaacg gccgccagtg    3660
tgctggaatt caccatgggg caacccggga acggcagcgc cttcttgctg cacccaatg    3720 gaagccatgc gccggaccac gacgtcacgc agcaaaggga cgaggtgtgg gtggtgggca    3780
tgggcatcgt catgtctctc atcgtcctgg ccatcgtgtt tggcaatgtg ctggtcatca    3840
cagccattgc caagttcgag cgtctgcaga cggtcaccaa ctacttcatc acaagcttgg    3900
cctgtgctga tctggtcatg gggctagcag tggtgccctt tggggccgcc catattctca    3960
tgaaaatgtg gactttggc aacttctggt gcgagttctg gacttccatt gatgtgctgt    4020
gcgtcacggc atcgattgag accctgtgcg tgatcgcagt cgaccgctac tttgccatta    4080
ctagtccttt caagtaccag agcctgctga ccaagaataa ggcccgggtg atcattctga    4140
tggtgtggat tgtgtcaggc cttacctcct tcttgcccat tcagatgcac tggtacaggg    4200
ccacccacca ggaagccatc aactgctatg ccaatgagac ctgctgtgac ttcttcacga    4260
accaagccta tgccattgcc tcttccatcg tgtccttcta cgttcccctg gtgatcatgg    4320
```

-continued

```
tcttcgtcta ctccagggtc tttcaggagg ccaaaaggca gctccagaag attgacaaat    4380
ctgagggccg cttccatgtc cagaaccttg gccaggtgga gcaggatggg cggacggggc    4440
atggactccg cagatcttcc aagttctgct tgaaggagca caaagccctc aagacgttag    4500
gcatcatcat gggcactttc accctctgct ggctgcccct cttcatcgtt aacattgtgc    4560
atgtgatcca ggataacctc atccgtaagg aagtttacat cctcctaaat tggataggct    4620
atgtcaattc tggtttcaat cccttatct actgccggag cccagatttc aggattgcct    4680
tccaggagct tctgtgcctg cgcaggtctt ctttgaaggc ctatggcaat ggctactcca    4740
gcaacggcaa cacaggggag cagagtggat atcacgtgga acaggagaaa gaaataaaac    4800
tgctgtgtga agacctccca ggcacggaag actttgtggg ccatcaaggt actgtgccta    4860
gcgataacat tgattcacaa gggaggaatt gtagtacaaa tgactcactg ctctcgagaa    4920
tcgagggccg gcaccaccat catcaccacg tcgaccccgg ggactacaag gatgacgatg    4980
acaagtaagc tttatccatc acactggcgg ccgctcgagc atgcatctag cggccgctcg    5040
aggccggcaa ggccggatcc ccgggaattc gcccctctcc ctcccccccc cctaacgtta    5100
ctggccgaag ccgcttggaa taaggccggt gtgcgtttgt ctatatgtta ttttccacca    5160
tattgccgtc ttttggcaat gtgagggccc ggaaacctgg ccctgtcttc ttgacgagca    5220
ttcctagggg tctttcccct ctcgccaaag gaatgcaagg tctgttgaat gtcgtgaagg    5280
aagcagttcc tctggaagct tcttgaagac aaacaacgtc tgtagcgacc ctttgcaggc    5340
agcggaaccc cccacctggc gacaggtgcc tctgcggcca aaagccacgt gtataagata    5400
cacctgcaaa ggcggcacaa ccccagtgcc acgttgtgag ttggatagtt gtggaaagag    5460
tcaaatggct ctcctcaagc gtattcaaca aggggctgaa ggatgcccag aaggtacccc    5520
attgtatggg atctgatctg gggcctcggt gcacatgctt tacatgtgtt tagtcgaggt    5580
taaaaaaacg tctaggcccc ccgaaccacg gggacgtggt tttcctttga aaaacacgat    5640
gataatatgg cctcctttgt ctctctgctc ctggtaggca tcctattcca tgccacccag    5700
gccgagctca cccagtctcc agactccctg gctgtgtctc tgggcgagag ggccaccatc    5760
aactgcaagt ccagccagag tgttttgtac agctccaaca ataagaacta tttagcttgg    5820
tatcagcaga aaccaggaca gcctcctaag ctgctcattt actgggcatc tacccgggaa    5880
tccggggtcc ctgaccgatt cagtggcagc gggtctggga cagatttcac tctcaccatc    5940
agcagcctgc aggctgaaga tgtggcagtt tattactgtc agcaatatta tagtactcag    6000
acgttcggcc aagggaccaa ggtggaaatc aaacgaactg tggctgcacc atctgtcttc    6060
atcttcccgc catctgatga gcagttgaaa tctggaactg cctctgttgt gtgcctgctg    6120
aataacttct atcccagaga ggccaaagta cagtggaagg tggataacgc cctccaatcg    6180
ggtaactccc aggagagtgt cacagagcag gacagcaagg acagcaccta cagcctcagc    6240
agcaccctga cgctgagcaa agcagactac gagaaacaca aactctacgc ctgcgaagtc    6300
acccatcagg gcctgagatc gcccgtcaca aagagcttca caaggggag agtgttagtt    6360 ctagataatt aattaggagg agatctcgag ctcgcgaaag cttggcactg gccgtcgttt    6420
tacaacgtcg tgactgggaa aaccctggcg ttacccaact taatcgcctt gcagcacatc    6480
cccctttcgc cagcctccta ggtcgacatc gataaaataa aagatttat ttagtctcca    6540 gaaaaagggg ggaatgaaag accccacctg taggtttggc aagctagctt aagtaacgcc    6600
attttgcaag gcatggaaaa atacataact gagaatagag aagttcagat caaggtcagg    6660
aacagatgga acagctgaat atgggccaaa caggatatct gtggtaagca gttcctgccc    6720
```

```
cggctcaggg ccaagaacag atggaacagc tgaatatggg ccaaacagga tatctgtggt    6780
aagcagttcc tgccccggct cagggccaag aacagatggt ccccagatgc ggtccagccc    6840
tcagcagttt ctagagaacc atcagatgtt tccagggtgc cccaaggacc tgaaatgacc    6900
ctgtgcctta tttgaactaa ccaatcagtt cgcttctcgc ttctgttcgc gcgcttctgc    6960
tccccgagct caataaaaga gcccacaacc cctcactcgg ggcgccagtc ctccgattga    7020
ctgagtcgcc cgggtacccg tgtatccaat aaaccctctt gcagttgcat ccgacttgtg    7080
gtctcgctgt tccttgggag ggtctcctct gagtgattga ctacccgtca gcggggtct    7140
ttcatttggg ggctcgtccg ggatcgggag acccctgccc agggaccacc gacccaccac    7200
cgggaggtaa gctggctgcc tcgcgcgttt cggtgatgac ggtgaaaacc tctgacacat    7260
gcagctcccg gagacggtca cagcttgtct gtaagcggat gccgggagca gacaagcccg    7320
tcagggcgcg tcagcgggtg ttggcgggtg tcggggcgca gccatgaccc agtcacgtag    7380
cgatagcgga gtgtatactg gcttaactat gcggcatcag agcagattgt actgagagtg    7440
caccatatgc ggtgtgaaat accgcacaga tgcgtaagga aaaataccg catcaggcgc    7500
tcttccgctt cctcgctcac tgactcgctg cgctcggtcg ttcggctgcg gcgagcggta    7560
tcagctcact caaaggcggt aatacggtta tccacagaat cagggggataa cgcaggaaag    7620
aacatgtgag caaaaggcca gcaaaaggcc aggaaccgta aaaaggccgc gttgctggcg    7680
ttttccata ggctccgccc ccctgacgag catcacaaaa atcgacgctc aagtcagagg    7740
tggcgaaacc cgacaggact ataaagatac caggcgtttc cccctggaag ctccctcgtg    7800
cgctctcctg ttccgaccct gccgcttacc ggatacctgt ccgcctttct cccttcggga    7860
agcgtggcgc tttctcatag ctcacgctgt aggtatctca gttcggtgta ggtcgttcgc    7920
tccaagctgg gctgtgtgca cgaaccccc gttcagcccg accgctgcgc cttatccggt    7980
aactatcgtc ttgagtccaa cccggtaaga cgacttatc gccactggc agcagccact    8040
ggtaacagga ttagcagagc gaggtatgta ggcggtgcta cagagttctt gaagtggtgg    8100
cctaactacg gctacactag aaggacagta tttggtatct gcgctctgct gaagccagtt    8160
accttcggaa aaagagttgg tagctcttga tccggcaaac aaaccaccgc tggtagcggt    8220
ggtttttttg tttgcaagca gcagattacg cgcagaaaaa aaggatctca agaagatcct    8280
ttgatctttt ctacggggtc tgacgctcag tggaacgaaa actcacgtta agggattttg    8340
gtcatgagat tatcaaaaag gatcttcacc tagatccttt taaattaaaa atgaagtttt    8400
aaatcaatct aaagtatata tgagtaaact tggtctgaca gttaccaatg cttaatcagt    8460
gaggcaccta tctcagcgat ctgtctattt cgttcatcca tagttgcctg actccccgtc    8520
gtgtagataa ctacgatacg ggagggctta ccatctggcc ccagtgctgc aatgataccg    8580
cgagacccac gctcaccggc tccagattta tcagcaataa accagccagc cggaagggcc    8640
gagcgcagaa gtggtcctgc aactttatcc gcctccatcc agtctattaa ttgttgccgg    8700
gaagctagag taagtagttc gccagttaat agtttgcgca acgttgttgc cattgctgca    8760
ggcatcgtgg tgtcacgctc gtcgtttggt atggcttcat tcagctccgg ttcccaacga    8820
tcaaggcgag ttacatgatc ccccatgttg tgcaaaaaag cggttagctc cttcggtcct    8880
ccgatcgttg tcagaagtaa gttggccgca gtgttatcac tcatggttat ggcagcactg    8940
cataattctc ttactgtcat gccatccgta agatgctttt ctgtgactgg tgagtactca    9000
accaagtcat tctgagaata gtgtatgcgg cgaccgagtt gctcttgccc ggcgtcaaca    9060
```

```
cgggataata ccgcgccaca tagcagaact ttaaaagtgc tcatcattgg aaaacgttct    9120
tcggggcgaa aactctcaag gatcttaccg ctgttgagat ccagttcgat gtaacccact    9180
cgtgcaccca actgatcttc agcatctttt actttcacca gcgtttctgg gtgagcaaaa    9240
acaggaaggc aaaatgccgc aaaaaaggga ataagggcga cacggaaatg ttgaatactc    9300
atactcttcc tttttcaata ttattgaagc atttatcagg gttattgtct catgagcgga    9360
tacatatttg aatgtattta gaaaaataaa caaatagggg ttccgcgcac atttccccga    9420
aaagtgccac ctgacgtcta agaaaccatt attatcatga cattaaccta taaaaatagg    9480
cgtatcacga ggccctttcg tcttcaagaa t                                  9511

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
gatccactag taacggccgc cagaattcgc                                      30

<210> SEQ ID NO 36
<211> LENGTH: 43
<212> TYPE: DNA
<213> ORGANISM: Artificial Sequence
<220> FEATURE:
<223> OTHER INFORMATION: Synthetic

<400> SEQUENCE: 36
cagagagaca aaggaggcca tattatcatc gtgtttttca aag                       43
```